(12) United States Patent
Minn et al.

(10) Patent No.: US 7,479,471 B2
(45) Date of Patent: Jan. 20, 2009

(54) 2-AMINO-4-BICYCLYLAMINO-6H-1,3,5-TRIAZINES, PROCESSES FOR THEIR PREPARATION AND THEIR USE AS HERBICIDES AND PLANT GROWTH REGULATORS

(75) Inventors: Klemens Minn, Hattersheim (DE); Hartmut Ahrens, Frankfut (DE); Hansjörg Dietrich, Hofheim (DE); Lothar Willms, Hofheim (DE); Thomas Auler, Bad Soden (DE); Hermann Bieringer, Eppstein (DE); Hubert Menne, Hofheim (DE)

(73) Assignee: Bayer CropScience GmbH, Frankfurt (DE)

( * ) Notice: Subject to any disclaimer, the term of this patent is extended or adjusted under 35 U.S.C. 154(b) by 26 days.

(21) Appl. No.: 10/368,856

(22) Filed: Feb. 18, 2003

(65) Prior Publication Data
US 2004/0002424 A1    Jan. 1, 2004

(30) Foreign Application Priority Data
Feb. 20, 2002    (DE)    ................ 102 07 037

(51) Int. Cl.
*C07D 251/48*    (2006.01)
*C07D 403/12*    (2006.01)
*C07D 403/14*    (2006.01)
*C07D 403/04*    (2006.01)
*A01N 43/68*    (2006.01)

(52) U.S. Cl. ............ 504/230; 504/232; 544/208; 544/209

(58) Field of Classification Search ........... 544/208, 544/209; 504/232, 230
See application file for complete search history.

(56) References Cited

U.S. PATENT DOCUMENTS

| 3,816,419 A | 6/1974 | Cross et al. ............ 544/208 |
| 3,932,167 A | 1/1976 | Cross et al. ............ 544/208 |
| 3,953,506 A | 4/1976 | Spicer et al. ............ 504/232 |
| 3,953,606 A | 4/1976 | Spicer et al. ............ 424/322 |
| 4,156,670 A | 5/1979 | Asato ............ 504/232 |
| 6,069,114 A | 5/2000 | Lorenz et al. ............ 504/232 |

FOREIGN PATENT DOCUMENTS

| CA | 2 373 665 | 11/2000 |
| DE | 25 05 301 | 8/1975 |
| DE | 199 21 883 A1 | 11/2000 |
| EP | 0 492 615 A1 | 7/1992 |
| EP | 0 509 544 A2 | 10/1992 |
| EP | 0 864 567 A | 9/1998 |
| JP | 08183781 | 7/1996 |
| WO | WO 88/02368 | 4/1988 |
| WO | WO 90/09378 | 8/1990 |
| WO | WO 94/24086 | 10/1994 |
| WO | WO 97/19936 | 6/1997 |
| WO | WO 97/31904 | 9/1997 |
| WO | WO-01/25220 A1 * | 4/2001 |

* cited by examiner

*Primary Examiner*—Venkataraman Balasubramanian
(74) *Attorney, Agent, or Firm*—Frommer Lawrence & Haug LLP

(57) ABSTRACT

The compounds of the formula (I) and salts thereof

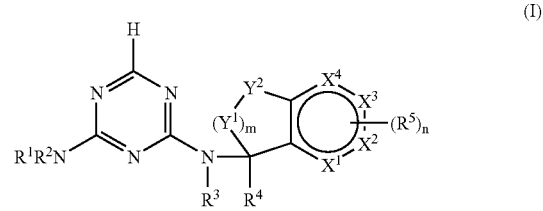

(I)

in which
$R^1$ to $R^5$, $X^1$ to $X^4$, $Y^1$, $Y^2$ and n and m are as defined in formula (I) according to claim 1 are suitable for use as herbicides and plant growth regulators and can be prepared by the process claimed in claim 6, via in some cases novel intermediates (see claim 11).

19 Claims, No Drawings

2-AMINO-4-BICYCLYLAMINO-6H-1,3,5-TRIAZINES, PROCESSES FOR THEIR PREPARATION AND THEIR USE AS HERBICIDES AND PLANT GROWTH REGULATORS

The invention relates to the technical field of herbicides and plant growth regulators, in particular herbicides for controlling broad-leaved weeds and weed grasses in crops of useful plants and unwanted growth of plants in general.

It is known that 2-amino-4-cyclohexylamino-6-perhaloalkyl-1,3,5-triazines (see, for example, U.S. Pat. No. 3,816,419 and U.S. Pat. No. 3,932,167) or 2-amino-4-alkylamino-6-haloalkyl-1,3,5-triazines (WO-A-90/09378 (EP-A-411153), WO-A-88/02368 (EP-A-283522), WO-A-94/24086, EP-A-509544, EP-A-492,615) and also 2-amino-4-bicyclylamino-1,3,5-triazines (WO 97/31904 (DE-A-19607-450), WO-A-97/19936) have herbicidal and plant-growth-regulating properties.

However, when derivatives of this type are used as selective herbicides for controlling harmful plants or as plant growth regulators in various crops of useful plants, it is frequently required to use excessive application rates, or there is unwanted damage to the crop plants. Moreover, the use of the active compounds is in many cases uneconomical owing to relatively high manufacturing costs. Surprisingly, novel bicyclic substituted 2,4-diamino-1,3,5-triazines have now been found which can be used in an advantageous manner as herbicides and plant growth regulators. In addition to a good activity profile and compatibility with crop plants, the compounds of this group are characterized by low-cost preparation processes and access to the triazine moiety, since, in the case of the substances described herein, the triazine can be prepared from inexpensive and readily accessible precursors, and the use of expensive intermediates which are difficult to obtain can be dispensed with.

The present invention provides compounds of the formula (I) and salts thereof

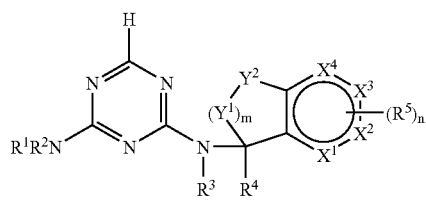

(I)

in which $R^1$ and $R^2$ are each independently of one another hydrogen, a group of the formula NR'R", where R' and R" are each independently of one another H, $(C_1-C_6)$alkyl, $(C_2-C_6)$alkenyl, $(C_2-C_6)$alkynyl, $(C_3-C_6)$cycloalkyl or $(C_5-C_6)$cycloalkenyl, or an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, preferably 1 to 12 carbon atoms, in particular 1 to 8 carbon atoms, or $R^1$ and $R^2$ together with the nitrogen atom of the group $NR^1R^2$ are a saturated or unsaturated, nonaromatic heterocyclic radical having 3 to 9 ring atoms and 1 to 4 hetero ring atoms, where the further hetero ring atoms optionally present in addition to the nitrogen atom are selected from the group consisting of N, O and S and the radical is unsubstituted or substituted, where each of the carbon-containing radicals $R^1$ and $R^2$ including substituents has 1 to 20 carbon atoms, preferably 1 to 12 carbon atoms, in particular 1 to 10 carbon atoms, $R^3$ is hydrogen, amino, $(C_1-C_4)$alkylamino, di$(C_1-C_4)$alkylamino, $(C_1-C_6)$alkyl, $(C_1-C_6)$alkoxy, $(C_2-C_6)$alkenyl, $(C_2-C_6)$alkynyl, $(C_3-C_6)$cycloalkyl, $(C_5-C_6)$cycloalkenyl, phenyl or heterocyclyl, where each of the 10 last-mentioned radicals independently of the others is unsubstituted or substituted and the radical in question including substituents has 1 to 12 carbon atoms, in particular 1 to 10 carbon atoms, or an acyl radical of the formula -B*-A*, where A* is hydrogen or an acyclic or cyclic hydrocarbon radical having 1 to 10 carbon atoms, preferably 1 to 6 carbon atoms, which is unsubstituted or substituted, and B* is a divalent group of the formula —CO—, —CO—O—, —CO—$NR^1$—, —S(O)$_p$— or —S(O)$_p$—O—, where p=0, 1 or 2 and $R^1$ is hydrogen, alkyl having 1 to 6 carbon atoms, phenyl, benzyl, cycloalkyl having 3 to 6 carbon atoms or alkanoyl having 1 to 6 carbon atoms, where -B*-A* including substituents has 1 to 12 carbon atoms, preferably 1 to 10 carbon atoms, $R^4$ is a radical of the formula -$Z^1$-$R^6$, where $Z^1$ and $R^6$ are as defined below, $R^5$ are each independently of one another halogen, cyano, isocyanato, nitro, a radical of the formula -$Z^2$-$R^7$, where $Z^2$ and $R^7$ are as defined below, or two adjacent radicals $R^5$ together are a fused-on cycle having 4 to 6 ring atoms which is carbocyclic or contains 1 to 3 hetero ring atoms from the group consisting of O, S and N and which is unsubstituted or substituted by one or more radicals from the group consisting of halogen, $(C_1-C_4)$alkyl and oxo, $R^6$, $R^7$, $R^8$, $R^9$ are each independently of one another hydrogen, except that $R^7$ is not hydrogen if $Z^2$ is a direct bond, or an acyclic hydrocarbon radical having 1 to 20 carbon atoms, preferably 1 to 10 carbon atoms, or a cyclic hydrocarbon radical, preferably a monocyclic hydrocarbon radical, having preferably 3 to 8 carbon atoms, in particular 3 to 6 carbon atoms, or a heterocyclic radical, having preferably 3 to 9 ring atoms and 1 to 3 hetero ring atoms from the group consisting of N, O and S, where each of the three last-mentioned radicals is unsubstituted or substituted and, including substituents, has preferably up to 30 carbon atoms, in particular up to 20 carbon atoms, or $R^8$ and $R^9$ together with the carbon atom of a group $CR^8R^9$ (for $Y^1$ or $Y^2$) or two radicals $R^8$ or $R^9$ from two groups $Y^1$ and/or $Y^2$ together with the attached atoms of the groups $Y^1$ and/or $Y^2$ are in each case a carbocyclic radical having 3 to 8 carbon atoms, in particular 3 to 6 carbon atoms, or a heterocyclic radical, having preferably 3 to 9 ring atoms and 1 to 3 hetero ring atoms from the group consisting of N, O and S, where each of the two last-mentioned radicals is unsubstituted or substituted and, including substituents, has preferably up to 16 carbon atoms, in particular up to 12 carbon atoms, $X^1$, $X^2$, $X^3$, $X^4$ are each independently of one another a carbon atom which is substituted by a hydrogen atom or one of the substituents $R^5$ defined above, or a nitrogen atom, or two adjacent symbols $X^1$, $X^2$, $X^3$ and $X^4$ are in each case together a divalent group of the formula —O—, —S—, —NH— or —NR—, where R is as defined for $R^3$ and is preferably hydrogen or $(C_1-C_6)$alkyl, provided the groups $X^1$, $X^2$, $X^3$, $X^4$ together with the attached $C_2$ unit of the fused-on ring form a carbocyclic or heterocyclic aromatic five- or six-membered ring, $(Y^1)_m$ are m divalent groups $Y^1$, where each group $Y^1$ independently of the other radicals $Y^1$ is a group of the formula —O—, —CO—, —C(=NR*)—, —S(O)$_q$—, —NR*— or —N(O)—, where q=0, 1 or 2 and R* is as defined for $R^3$ and is preferably hydrogen, $(C_1-C_6)$alkyl, benzyl or phenyl, in particular hydrogen, $(C_1-C_6)$alkyl or phenyl, or a group of the formula $CR^8R^9$, where $R^8$ and $R^9$ are as defined above, and $Y^2$ is a group as defined for $Y^1$ or a direct bond, where two adjacent groups of the symbol pairs $Y^1$ and $Y^1$ or of the symbol pairs $Y^1$ and $Y^2$ are groups with no heteroatoms having the same meaning, and where the groups $(Y^1)_m$ and $Y^2$ together with the attached $C_2$ unit of the aromatic ring and the carbon atom attached to $R^4$ form a fused-on carbocyclic or heterocyclic nonaromatic four- to eight-membered ring, $Z^1$ and the groups $Z^2$ are each independently of one another a direct bond or a divalent group of the formula —O—, —S(O)$_p$—, —S(O)$_p$—O—, —O—S(O)$_p$—, —CO—, —O—CO—, —CO—O—, —NR'—, —O—NR'—, —NR'—O—, —NR'—CO—, —CO—NR'—, where p=0, 1 or 2 and R' is hydrogen, alkyl having 1 to 6 carbon atoms, phenyl, benzyl, $(C_3-C_6)$cycloalkyl or alkanoyl having 1 to 6 carbon atoms, m is 0, 1, 2, 3 or 4, in particular 1 or 2, and n is 0, 1, 2, 3 or 4, in particular 0 or 1, especially 1 or 2.

The compounds of the formula (I) can form salts by addition of a suitable inorganic or organic acid, such as, for example, HCl, HBr, $H_2SO_4$ or $HNO_3$, but also oxalic acid or sulfonic acids, to a basic group, such as, for example, amino or alkylamino. Suitable substituents which are present in deprotonated form, such as, for example, sulfonic acids or carboxylic acids, can form internal salts with groups which for their part can be protonated, such as amino groups. Salts can also be formed by replacing the hydrogen in suitable substituents, such as, for example, sulfonic acids or carboxylic acids, by an agriculturally suitable cation. These salts are, for example, metal salts, in particular alkali metal salts or alkaline earth metal salts, in particular sodium salts and potassium salts, or else ammonium salts, salts with organic amines or quaternary ammonium salts.

In formula (I) and all subsequent formulae, the following definitions apply:

In the divalent groups, such as B*, $Z^1$ and $Z^2$, which can also symbolize bridges having a plurality of atoms, such as —CO—NR—, a composed radical in the notation -B*-A* or -$Z^1$-$R^6$ denotes the groups —CO—NR'-A* and —CO—NR'—$R^6$, respectively, and not the groups —NR'—CO-A* and —NR'—CO—$R^6$, respectively.

In the divalent groups —$(Y^1)_m$—, the attachment is defined such that the free binding site on the left is attached to the carbon atom which is substituted by $R^4$; correspondingly, the free binding site on the left of the next group $Y^1$ is attached to the free bond on the right of the first group Y.

A group of the formula —S(O)$_p$— denotes a sulfur atom having two free bonds and, doubly attached, p oxygen atoms, i.e. if p=0, 1 or 2, a group of the formula —S—, —S(=O)— (or short —SO—, sulfinyl) and —S(=O)$_2$— (or short —SO$_2$—, sulfonyl), respectively, and not additionally also —S—O— (sulfenyloxy) or —SO—O— (sulfinyloxy).

Heteroatomic groups are groups having one or more atoms and strongly functionalized character, which comprise one or more atoms differing from carbon atoms (heteroatoms), but may also contain carbon atoms. In the case of $Y^1$, these are groups of the formulae —O—, —CO—, —C(=NR*)—, —S(O)$_q$—, —NR*— and —N(O)—, but not groups of the formula $CR^8R^9$.

The terms alkyl, alkoxy, haloalkyl, haloalkoxy, alkylamino and alkylthio and the terms for the corresponding unsaturated and/or substituted radicals comprise in each case both relevant radicals having a straight-chain carbon radical and those having a branched (non-cyclic) carbon skeleton.

The term "$(C_1-C_4)$alkyl" is a short notation for alkyl having 1 to 4 carbon atoms, i.e. includes the radicals methyl, ethyl, 1-propyl, 2-propyl, 1-butyl, 2-butyl, 2-methylpropyl and tert-butyl. General alkyl radicals having a wider stated range of carbon atoms, for example "$(C_1-C_6)$alkyl", correspondingly embrace also straight-chain or branched alkyl radicals having a larger number of carbon atoms, i.e. in the example also the alkyl radicals having 5 and 6 carbon atoms.

Unless specifically indicated, the lower carbon skeletons, for example those having 1 to 6 carbon atoms, in particular 1 to 4 carbon atoms, and in the case of unsaturated groups having 2 to 6 carbon atoms, in particular 2 to 4 carbon atoms, are preferred in the hydrocarbon radicals, such as alkyl, alkenyl and alkynyl radicals, and also in the composite radicals. Alkyl radicals, including in the composite meanings such as alkoxy, haloalkyl, etc., are, for example, methyl, ethyl, n- or isopropyl, n-, iso-, tert- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meanings of the possible unsaturated radicals which correspond to the alkyl radicals; alkenyl is, for example, vinyl, allyl, 1-methyl-2-propenyl, 2-methyl-2-propenyl, 2-butenyl, pentenyl, 2-methylpentenyl or hexenyl, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl includes in particular also straight-chain or branched hydrocarbon radicals having more than one double bond, such as 1,3-butadienyl and 1,4-pentadienyl, but also allenyl or cumulenyl radicals having one or more cumulated double bonds, such as, for example, allenyl (1,2-propadienyl), 1,2-butadienyl and 1,2,3-pentatrienyl.

Alkynyl is, for example, propargyl, but-2-yn-1-yl, but-3-yn-1-yl, 1methylbut-3-yn-1-yl.

Alkynyl includes in particular also straight-chain or branched hydrocarbon radicals having more than one triple bond or else having one or more triple bonds and one or more double bonds, such as, for example, 1,3-butatrienyl or 3-penten-1-yn-1-yl.

Alkylidene, for example also in the form $(C_1-C_{10})$alkylidene, denotes the radical of a straight-chain or branched alkane which is attached via a double bond, where the position of the binding site is not yet fixed. Naturally, in the case of a branched alkane, the only positions possible are those in which two hydrogen atoms can be replaced by the double bond; possible radicals, are, for example, =$CH_2$, =CH—$CH_3$, =C($CH_3$)—$CH_3$, =C($CH_3$)—$C_2H_5$ or =C($C_2H_5$)—$C_2H_5$.

Cycloalkyl is a carbocyclic saturated ring system having preferably 3-8 carbon atoms, for example cyclopropyl, cyclobutyl, cyclopentyl or cyclohexyl. In the case of substituted cycloalkyl, this includes cyclic systems with substituents, where the substituents are bonded to the cycloalkyl radical by a double bond, for example an alkylidene group such as methylidene. In the case of substituted cycloalkyl, this also includes polycyclic aliphatic systems, such as, for example, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, adamantan-1-yl and adamantan-2-yl.

Cycloalkenyl is a carbocyclic, nonaromatic, partially unsaturated ring system having preferably 4-8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, what has been said for substituted cycloalkyl applies analogously.

Halogen is, for example, fluorine, chlorine, bromine or iodine. Haloalkyl, -alkenyl and -alkynyl are alkyl, alkenyl and alkynyl, respectively, which are partially or fully substituted by identical or different halogen atoms, preferably from the group consisting of fluorine, chlorine and bromine, in particular from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies analogously to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic; unless defined otherwise, it preferably contains one or more, in particular 1, 2 or 3, heteroatoms in the heterocyclic ring, preferably from the group consisting of N, O and S; it is preferably an aliphatic heterocyclyl radical having 3 to 7 ring atoms or a heteroaromatic radical having 5 or 6 ring atoms. The heterocyclic radical can, for example, be a heteroaromatic radical or ring (heteroaryl), such as, for example, a mono-, bi- or polycyclic aromatic system in which at least 1 ring contains one or more heteroatoms. It is preferably a heteroaromatic ring which contains one heteroatom from the group consisting of N, O and S, for example pyridyl, pyrrolyl, thienyl or furyl; furthermore preferably, it is a corresponding heteroaromatic ring having 2 or 3 heteroatoms, for example pyrimidinyl, pyridazinyl, pyrazinyl, triazinyl, thiazolyl, thiadiazolyl, oxazolyl, isoxazolyl, pyrazolyl, imidazolyl and triazolyl. Furthermore preferably, it is a partially or fully hydrogenated heterocyclic radical having one heteroatom from the group consisting of N, O and S, for example oxiranyl, oxetanyl, oxolanyl (=tetrahydrofuryl), oxanyl, pyrrolinyl, pyrrolidyl or piperidyl, It is furthermore preferably a partially or fully hydrogenated heterocyclic radical having 2 heteroatoms from the group consisting of N, O and S, for example piperazinyl, dioxolanyl, oxazolinyl, isoxazolinyl, oxazolidinyl, isoxazolidinyl and morpholinyl.

Possible substituents for a substituted heterocyclic radical are the substituents mentioned further below, and additionally also oxo. The oxo group can also be present at those hetero ring atoms where various oxidation numbers are possible, for examples in the case of N and S.

Preferred examples of heterocyclyl are heterocyclic radicals having 3 to 6 ring atoms from the group consisting of pyridyl, thienyl, furyl, pyrrolyl, oxiranyl, 2-oxetanyl, 3-oxetanyl, oxolanyl (=tetrahydrofuryl), pyrrolidyl, piperidyl, in particular oxiranyl, 2-oxetanyl, 3-oxetanyl or oxolanyl, or heterocyclic radicals having two or three heteroatoms, for example pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

If a parent structure is substituted "by one or more radicals" from a list of radicals (=group) or a generically defined group of radicals, this includes in each case the simultaneous substitution by a plurality of identical and/or structurally different radicals.

Substituted radicals, such as substituted alkyl, alkenyl, alkynyl, aryl, phenyl, benzyl, heterocyclyl and heteroaryl radicals, are, for example, a substituted radical which is derived from the unsubstituted parent structure, the substituents being, for example, one or more, preferably 1, 2 or 3, radicals selected from the group consisting of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, alkylsulfonyl and, in case of cyclic radicals, also alkyl, haloalkyl, alkylthioalkyl, alkoxyalkyl, optionally substituted mono- and dialkylaminoalkyl and hydroxyalkyl; the term "substituted radicals", such as substituted alkyl etc. includes as substituents, in addition to the saturated hydrocarbon-containing radicals mentioned, the corresponding unsaturated aliphatic and aromatic radicals, such as unsubstituted or substituted alkenyl, alkynyl, alkenyloxy, alkynyloxy, phenyl, phenoxy etc. In the case of substituted cyclic radicals having aliphatic moieties in the ring, this also includes cyclic systems having substituents which are attached to the ring via a double bond, for example those which are substituted by an alkylidene group such as methylidene or ethylidene.

The substituents mentioned by way of example ("first substituent level") can, if they contain hydrocarbon-containing moieties, be, if appropriate, substituted further in these moieties ("second substituent level"), for example by one of the substituents defined for the first substituent level. Corresponding further substituent levels are possible. The term "substituted radical" preferably embraces only one or two substituent levels.

Preferred substituents for the substituent levels are, for example:

amino, hydroxyl, halogen, nitro, cyano, mercapto, carboxyl, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

Among the radicals with carbon atoms, preference is given to those having 1 to 6 carbon atoms, preferably 1 to 4 carbon atoms, in particular 1 or 2 carbon atoms. In general, preference is given to substituents selected from the group consisting of halogen, for example fluorine and chlorine, $(C_1-C_4)$ alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Substituted amino, such as mono- or disubstituted amino, is a radical from the group of the substituted amino radicals which are N-substituted, for example, by one or two identical or different radicals selected from the group consisting of alkyl, alkoxy, acyl and aryl; preferably mono- and dialkylamino, mono- and diarylamino, acylamino, N-alkyl-N-arylamino, N-alkyl-N-acylamino and also N-heterocycles; preference is given here to alkyl radicals having 1 to 4 carbon atoms; aryl is preferably phenyl or substituted phenyl; for acyl, the definition given further below applies, preferably $(C_1-C_4)$alkanoyl. This applies correspondingly to substituted hydroxylamino or hydrazino.

Unsubstituted or substituted phenyl is preferably phenyl which is unsubstituted or mono- or polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Acyl is a radical of an organic acid which is formally formed by removing a hydroxyl group from the acid function, where the organic radical in the acid can also be attached to the acid function via a heteroatom. Examples of acyl are the radical —CO—R of a carboxylic acid HO—CO—R and radicals of acids derived therefrom, such as thiocarboxylic acid, unsubstituted or N-substituted iminocarboxylic acids or the radical of carbonic monoesters, N-substituted carbamic acid, sulfonic acids, sulfinic acids, N-substituted sulfonamide acids, phosphonic acids or phosphinic acids.

Acyl is, for example, formyl, alkylcarbonyl, such as [$(C_1-C_4)$alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals can in each case be further substituted in the alkyl or phenyl moiety, for example in the alkyl moiety by one or more radicals selected from the group consisting of halogen, alkoxy, phenyl and phenoxy; examples of substituents in the phenyl moiety are the substituents which have already been mentioned further above generally for substituted phenyl.

Acyl is preferably an acyl radical in the more restricted sense, i.e. a radical of an organic acid where the acid group is directly attached to the carbon atom of an organic radical, for example, formyl, alkylcarbonyl, such as acetyl or [$(C_1-C_4)$alkyl]carbonyl, phenylcarbonyl, alkylsulfonyl, alkylsulfinyl and other radicals of organic acids.

The compounds of the formula (I) also embrace all tautomers which, by hydrogen shift, are in equilibrium with the compounds of the formula (I) named.

The invention also provides all stereoisomers which are embraced by the formula (I) and mixtures thereof. Such compounds of the formula (I) contain one or more asymmetric carbon atoms or else double bonds, which are not specifically mentioned in the general formula (I). The possible stereoisomers, which are defined by their specific spatial form, such as enantiomers, diastereomers, Z and E isomers, are all embraced by the formula (I) and can be obtained by customary methods from mixtures of the stereoisomers or else be prepared by stereoselective reactions in combination with the use of stereochemically pure starting materials. This applies correspondingly to the other general formulae mentioned below.

The carbon atom in formula (I), for example, by which the bicycle is attached to one of the amino groups of the diaminotriazine is a center of chirality which can be present in the R or S configuration (Cahn-Ingold-Prelog nomenclature). Accordingly, the invention also provides, in particular, the herbicidally active stereoisomers which are purified or enriched with respect to the enantiomeric excess (% ee) with respect to the center of chirality mentioned (enantiomers in the case of one center of chirality; or else, if a plurality of centers of chiralty is present, enantiomers/diastereomers).

In particular for reasons of better herbicidal activity, better selectivity and/or easier preparation, the novel compounds of the formula (I) mentioned or their salts of particular interest are those in which individual radicals have one of the preferred meanings already mentioned or mentioned hereinbelow, or, in particular, those in which one or more of the preferred meanings already mentioned or mentioned hereinbelow are combined.

Preference is also given to compounds of the general formula (I) according to the invention and their salts in which one or more radicals, groups or symbols $R^1$, $R^2$, $R^3$, $R^4$, $R^5$, $Y^1$, $Y^2$, $X^1$, $X^2$, $X^3$, $X^4$, $Y^1$, $Y^2$, n and m are as defined in one of the specific examples mentioned further below (working examples, examples in tables), or are defined according to the generic definition corresponding to the definition mentioned by way of example (ethoxy, for example, belongs to alkoxy or preferably $(C_1-C_6)$alkoxy, etc.).

Hereinbelow, compounds of the formula (I) according to the invention and their salts are in short also referred to as "compounds (I) according to the invention" or even shorter as "compounds (I)".

Independently of the respective other meanings of the radicals and symbols from the group $R^1$, $R^2$, $R^3$, $R^4$, $R^5$, $R^6$, $R^7$, $R^8$, $R^9$, $X^1$, $X^2$, $X^3$, $X^4$, $Y^1$, $Y^2$, n and m, including the general radicals of the corresponding submeanings, and preferably in combination with preferred meanings of one or more of these radicals, compounds (I) according to the invention of particular interest are those in which the radicals in question have the preferred meanings listed below.

$R^1$ and $R^2$ are preferably each independently of one another hydrogen, amino, alkylamino or dialkylamino having in each case 1 to 4 carbon atoms in the alkyl radical or $(C_3-C_6)$cycloalkylamino, $(C_5-C_6)$cycloalkenylamino, an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms, preferably 3 to 6 ring atoms, and 1 to 3 hetero ring atoms from the group consisting of N, O and S, where each of the six last-mentioned radicals is unsubstituted or substituted by one or more radicals from the group consisting of halogen, hydroxyl, amino, nitro, formyl, aminocarbonyl, carboxyl, sulfonyl, cyano, thiocyanato, $(C_1-C_6)$alkoxy, $(C_2-C_6)$alkenyloxy, $(C_2-C_6)$alkynyloxy, $(C_1-C_6)$alkoxy-poly(alkyleneoxy), hydroxy-poly(alkyleneoxy), $(C_1-C_6)$alkylthio, mono- and di[$(C_1-C_6)$alkyl]amino, [$(C_1-C_6)$alkyl]carbonyl, [$(C_2-C_6)$alkenyl]carbonyl, [$(C_2-C_6)$alkynyl]carbonyl, [$(C_1-C_6)$alkoxy]carbonyl, [$(C_2-C_6)$alkenyloxy]carbonyl, [$(C_2-C_6)$alkynyloxy]carbonyl, mono- and di[$(C_1-C_6)$alkyl]aminocarbonyl, phenyl, phenoxy, $(C_3-C_6)$cycloalkyl, phenylcarbonyl, phenoxycarbonyl, heterocyclyl, $(C_1-C_4)$alkylsulfonyl and, in the case of cyclic radicals, also $(C_1-C_4)$alkyl, where each of the 24 last-mentioned substituents is unsubstituted or substituted by one or more radicals from the group consisting of halogen, CN, SCN, $NO_2$, $(C_1-C_4)$alkoxy, $(C_1-C_4)$alkylthio, $(C_1-C_4)$haloalkoxy, formyl, $(C_1-C_4)$alkylcarbonyl, [$(C_1-C_4)$haloalkyl]carbonyl, [$(C_1-C_4)$alkoxy]carbonyl, [$(C_1-C_4)$haloalkoxy]carbonyl and, in the case of cyclic radicals, also $(C_1-C_4)$alkyl and $(C_1-C_4)$haloalkyl, or an acyl radical of an organic acid from the group consisting of formyl, aminocarbonyl, mono- and di[$(C_1-C_4)$alkyl]aminocarbonyl, [$(C_1-C_6)$alkyl]carbonyl, [$(C_2-C_6)$alkenyl]carbonyl, [$(C_2-C_6)$alkynyl]carbonyl, [$(C_1-C_6)$alkoxy]carbonyl, [$(C_2-C_6)$alkenyloxy]carbonyl, phenylcarbonyl, ($C_1$-$C_6$)alkylsulfonyl, where each of the 9 last-mentioned radicals is unsubstituted in the aliphatic moiety or in the phenyl ring or substituted by one or more radicals from the group consisting of halogen, CN, SCN, $NO_2$, ($C_1$-$C_4$)alkoxy, ($C_1$-$C_4$)haloalkoxy, optionally substituted and preferably unsubstituted phenyl and, in the case of cyclic radicals, also ($C_1$-$C_6$)alkyl and ($C_1$-$C_6$)haloalkyl, where heterocyclyl, unless defined in more detail, and including in composite radicals, has in each case 3 to 9 ring atoms, preferably 3 to 6 ring atoms, and 1 to 3 hetero ring atoms from the group consisting of N, O and S, or $R^1$ and $R^2$ together with the nitrogen atom of the group $NR^1R^2$ are a saturated or unsaturated, nonaromatic heterocyclic radical having 3 to 6 ring atoms and 1 to 4 hetero ring atoms, where the further hetero ring atoms optionally present in addition to the nitrogen atom are selected from the group consisting of N, O and S and the radical is unsubstituted or substituted by one or more radicals from the group consisting of halogen, CN, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkoxycarbonyl and oxo.

$R^1$ and $R^2$ are more preferably each independently of one another hydrogen, amino, mono- or di[($C_1$-$C_4$)alkyl]amino or ($C_3$-$C_6$)cycloalkylamino, ($C_5$-$C_6$)cycloalkenylamino, an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms, preferably 3 to 6 ring atoms, and 1 to 3 hetero ring atoms from the group consisting of N, O and S, where each of the six last-mentioned radicals is unsubstituted or substituted by one or more radicals from the group consisting of halogen, hydroxyl, amino, nitro, formyl, aminocarbonyl, carboxyl, sulfonyl, cyano, thiocyanato, ($C_1$-$C_4$)alkoxy, ($C_2$-$C_4$)alkenyloxy, ($C_2$-$C_4$)alkynyloxy, ($C_1$-$C_4$)alkoxy-poly(alkyleneoxy), hydroxy-poly(alkyleneoxy), ($C_1$-$C_4$)alkylthio, mono- and di[($C_1$-$C_4$)alkyl]amino, [($C_1$-$C_4$)alkyl]carbonyl, [($C_2$-$C_4$)alkenyl]carbonyl, [($C_2$-$C_4$)alkynyl]carbonyl, [($C_1$-$C_4$)alkoxy]carbonyl, [($C_2$-$C_4$)alkenyloxy]carbonyl, [($C_2$-$C_4$)alkynyloxy]carbonyl, mono- and di[($C_1$-$C_4$)alkyl]aminocarbonyl, phenyl, phenoxy, ($C_3$-$C_6$)cycloalkyl, phenylcarbonyl, phenoxycarbonyl, heterocyclyl, ($C_1$-$C_4$)alkylsulfonyl and, in the case of cyclic radicals, also ($C_1$-$C_4$)alkyl, where each of the 24 last-mentioned substituents is unsubstituted or substituted by one or more radicals from the group consisting of halogen, CN, SCN, $NO_2$, ($C_1$-$C_4$)alkoxy, ($C_1$-$C_4$)haloalkoxy, formyl, ($C_1$-$C_4$)alkylcarbonyl, [($C_1$-$C_4$)haloalkyl]carbonyl, [($C_1$-$C_4$)alkoxy]carbonyl, [($C_1$-$C_4$)haloalkoxy]carbonyl and, in the case of cyclic radicals, also ($C_1$-$C_4$)alkyl and ($C_1$-$C_4$)haloalkyl, or an acyl radical of an organic acid from the group consisting of formyl, aminocarbonyl, mono- or di[($C_1$-$C_4$)alkyl]aminocarbonyl, [($C_1$-$C_4$)alkyl]carbonyl, [($C_2$-$C_4$)alkenyl]carbonyl, [($C_2$-$C_4$)alkynyl]carbonyl, [($C_1$-$C_4$)alkoxy]carbonyl, [($C_2$-$C_4$)alkenyloxy]carbonyl, phenylcarbonyl, ($C_1$-$C_4$)alkylsulfonyl, where each of the 9 last-mentioned radicals is unsubstituted in the aliphatic moiety or in the phenyl ring or substituted by one or more radicals from the group consisting of halogen, CN, SCN, $NO_2$, ($C_1$-$C_4$)alkoxy, ($C_1$-$C_4$)haloalkoxy, optionally substituted and preferably unsubstituted phenyl and, in the case of cyclic radicals, also ($C_1$-$C_4$)alkyl and ($C_1$-$C_4$)haloalkyl, where heterocyclyl, unless defined in more detail, and including in composite radicals, has in each case 3 to 9 ring atoms, preferably 3 to 6 ring atoms, and 1 to 3 hetero ring atoms from the group consisting of N, O and S, or $R^1$ and $R^2$ together with the nitrogen atom of the group $NR^1R^2$ are a saturated or unsaturated, nonaromatic heterocyclic radical having 3 to 6 ring atoms and 1 to 4 hetero ring atoms, in particular 1 or 2 hetero ring atoms where the further hetero ring atoms optionally present in addition to the nitrogen atom are selected from the group consisting of N, O and S and the radical is unsubstituted or substituted by one or more radicals from the group consisting of halogen, CN, ($C_1$-$C_4$)alkyl, ($C_1$-$C_4$)haloalkyl, ($C_1$-$C_4$)alkoxy, ($C_1$-$C_4$)alkoxycarbonyl and oxo, $R^1$ and $R^2$ are furthermore preferably each independently of one another hydrogen, amino, alkylamino or dialkylamino having in each case 1 to 4 carbon atoms in the alkyl radical, or ($C_3$-$C_6$)cycloalkylamino, ($C_5$-$C_6$)cycloalkenylamino, an (acyclic or cyclic) hydrocarbon radical or hydrocarbonoxy radical having in each case 1 to 10 carbon atoms, preferably 1 to 6 carbon atoms, or a heterocyclyl radical, heterocyclyloxy radical, heterocyclylthio radical or heterocyclylamino radical having in each case 3 to 9 ring atoms, preferably 3 to 6 ring atoms, and 1 to 3 hetero ring atoms from the group consisting of N, O and S, where each of the six last-mentioned radicals is unsubstituted or substituted by one or more radicals from the group consisting of halogen, hydroxyl, amino, nitro, formyl, carboxyl, sulfonyl, cyano, thiocyanato, ($C_1$-$C_4$)alkoxy, ($C_1$-$C_4$)alkoxy-($C_1$-$C_4$)alkoxy, hydroxy-($C_1$-$C_4$)alkoxy, ($C_1$-$C_4$)alkoxy-poly(alkyleneoxy), hydroxy-poly(alkyleneoxy), ($C_1$-$C_4$)haloalkoxy, ($C_1$-$C_4$)alkylthio, ($C_1$-$C_4$)haloalkylthio, mono ($C_1$-$C_4$)alkylamino, di($C_1$-$C_4$)alkylamino, [($C_1$-$C_4$)alkyl]carbonyl, [($C_1$-$C_4$)alkoxy]carbonyl, aminocarbonyl, mono ($C_1$-$C_4$)alkylaminocarbonyl, di($C_1$-$C_4$)alkylaminocarbonyl, phenyl, phenoxy, ($C_3$-$C_6$)cycloalkyl, phenylcarbonyl, phenoxycarbonyl, heterocyclyl, where each of the 6 last-mentioned radicals is unsubstituted or substituted by one or more radicals from the group consisting of halogen, CN, SCN, $NO_2$, ($C_1$-$C_4$)alkyl, ($C_1$-$C_4$)haloalkyl, ($C_1$-$C_4$)alkoxy and ($C_1$-$C_4$)haloalkoxy, and ($C_1$-$C_4$)alkylsulfonyl and ($C_1$-$C_4$)haloalkylsulfonyl and, in the case of cyclic: radicals, also ($C_1$-$C_4$)alkyl and ($C_1$-$C_4$)haloalkyl, or an acyl radical of an organic acid from the group consisting of formyl, [($C_1$-$C_4$)alkyl]carbonyl, [($C_1$-$C_4$)haloalkyl]carbonyl, [($C_1$-$C_4$)alkoxy-($C_1$-$C_4$)alkyl]carbonyl, [($C_2$-$C_4$)alkenyl]carbonyl, [($C_2$-$C_4$)haloalkenyl]carbonyl, [($C_1$-$C_4$)alkoxy]carbonyl, [($C_1$-$C_4$)haloalkoxy]carbonyl, [($C_1$-$C_4$)alkoxy-($C_1$-$C_4$)alkoxy]carbonyl, [($C_2$-$C_4$)alkenyloxy]carbonyl, [($C_2$-$C_4$)haloalkenyloxy]carbonyl, [($C_1$-$C_4$)alkynyloxy]carbonyl, phenylcarbonyl and benzylcarbonyl, where each of the two last-mentioned radicals is unsubstituted in the phenyl ring or substituted by one or more radicals from the group consisting of halogen, CN, SCN, $NO_2$, ($C_1$-$C_4$)alkyl, ($C_1$-$C_4$)haloalkyl, ($C_1$-$C_4$)alkoxy, ($C_1$-$C_4$)alkylthio and ($C_1$-$C_4$)haloalkoxy, and ($C_1$-$C_4$)alkylsulfonyl, ($C_1$-$C_4$)haloalkylsulfonyl and [($C_1$-$C_4$)alkoxy-($C_1$-$C_4$)alkoxy]sulfonyl, where heterocyclyl is as defined elsewhere.

Moreover, preferably, $R^1$, $R^2$ independently of one another are hydrogen, amino, formyl, ($C_1$-$C_4$)alkyl, cyano-($C_1$-$C_4$)alkyl, ($C_1$-$C_4$)alkylamino, di[($C_1$-$C_4$)alkyl]amino, ($C_1$-$C_4$)haloalkyl, mono-, di- or polyhydroxy-($C_1$-$C_4$)alkyl, hydroxy-poly[($C_2$-$C_4$)alkyleneoxy]-($C_1$-$C_4$)alkyl, mono-, di- or poly($C_1$-$C_4$)alkoxy-($C_1$-$C_4$)alkyl, ($C_1$-$C_4$)alkoxy-poly[($C_2$-$C_4$)alkyleneoxy]-$(C_1-C_4)$alkyl, $(C_1-C_4)$haloalkoxy-$(C_1-C_4)$alkyl, $(C_2-C_6)$alkenyl, $(C_2-C_6)$haloalkenyl, $(C_2-C_6)$alkynyl, $(C_2-C_6)$haloalkynyl or aminocarbonyl, or $(C_1-C_4)$alkylamino-$(C_1-C_4)$alkyl, di[$(C_1-C_4)$alkyl]amino-$(C_1-C_4)$alkyl, $(C_1-C_4)$alkylaminocarbonyl, di$(C_1-C_4)$alkylaminocarbonyl, $(C_1-C_5)$alkanoyl, [$(C_2-C_4)$alkenyl]carbonyl, [$(C_1-C_4)$alkoxy]carbonyl, $(C_2-C_4)$alkenyloxycarbonyl, aminocarbonyl-$(C_1-C_4)$alkyl, $(C_1-C_4)$alkylaminocarbonyl-$(C_1-C_4)$alkyl, di[$(C_1-C_4)$alkyl]aminocarbonyl-$(C_1-C_4)$alkyl, $(C_1-C_4)$alkoxycarbonyl-$(C_1-C_4)$alkyl, $(C_1-C_5)$alkanoyl-$(C_1-C_4)$alkyl, [$(C_2-C_4)$alkenyl]carbonyl-$(C_1-C_4)$alkyl, [$(C_1-C_4)$alkoxy]carbonyl-$(C_1-C_4)$alkyl or $(C_2-C_4)$alkenyloxycarbonyl-$(C_1-C_4)$alkyl, where each of the 16 last-mentioned radicals is unsubstituted or substituted by one or more radicals from the group consisting of halogen, CN, $(C_1-C_4)$alkoxy and $(C_1-C_4)$haloalkoxy, or $(C_3-C_6)$cycloalkyl, $(C_3-C_6)$cycloalkylamino-$(C_1-C_4)$alkyl, phenyl, phenoxy, phenylcarbonyl, phenoxycarbonyl, phenylcarbonyl-$(C_1-C_4)$alkyl, phenoxy-$(C_1-C_4)$alkyl, phenyl-$(C_1-C_4)$alkyl, heterocyclyl, heterocyclyl-$(C_1-C_4)$alkyl, heterocyclylamino, heterocyclyloxy or heterocyclylthio or one of the 14 last-mentioned radicals which is substituted in the acyclic moiety or, preferably, in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl and $(C_1-C_4)$alkoxy, where heterocyclyl in the radicals contains in each case 3 to 9 ring atoms and 1 to 3 hetero ring atoms from the group consisting of N, O and S, or $R^1$ and $R^2$ together with the nitrogen atom of the group $NR^1R^2$ are a heterocyclic radical having 3 to 6 ring atoms and 1 or 2 hetero ring atoms, where in addition to the nitrogen atom the further hetero ring atom which may be present is selected from the group consisting of N, O and S and where the radical is unsubstituted or substituted by one or more radicals from the group consisting of halogen, $(C_1-C_4)$alkyl and oxo.

Furthermore, preferably, $R^1$, $R^2$ independently of one another are hydrogen, amino, formyl, $(C_1-C_4)$alkyl, $(C_1-C_4)$alkylamino, di[$(C_1-C_4)$alkyl]amino, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, $(C_2-C_6)$alkynyl, halo-$(C_2-C_6)$alkynyl, $(C_1-C_4)$alkylamino-$(C_1-C_4)$alkyl or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl or one of the 10 last-mentioned radicals which is susbstituted in the acyclic moiety or, preferably, in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, formyl, $(C_1-C_4)$alkylcarbonyl, $(C_1-C_4)$alkoxycarbonyl and $(C_1-C_4)$alkoxy, where heterocyclyl in the radicals preferably contains in each case 3 to 7 ring atoms and 1 to 3 hetero ring atoms from the group consisting of N, O and S.

With particular preference, the group $NR^1R^2$ is amino, hydrazino, mono- or dialkylamino having 1 to 4 carbon atoms in the alkyl radicals, $(C_1-C_5)$alkanoylamino, N-$(C_1-C_5)$alkanoyl-N-$(C_1-C_4)$alkylamino, [$(C_1-C_4)$haloalkyl]carbonylamino, N-[$(C_1-C_4)$haloalkyl]carbonyl-N-$(C_1-C_4)$alkylamino, [$(C_1-C_4)$alkoxy-$(C_1-C_4)$alkylcarbonyl]amino, N-[$(C_1-C_4)$alkoxy-$(C_1-C_4)$alkylcarbonyl]-N-[$(C_1-C_4)$alkyl]amino, phenylamino, benzylamino, benzoylamino, morpholino, piperidino, piperidin-1-ylamino;

in particular amino, hydrazino, methylamino, ethylamino, dimethylamino, acetylamino, propionylamino, chloroacetylamino, (2-chloroethyl)carbonylamino, trifluoromethylcarbonylamino or trichloromethylcarbonylamino; especially amino.

Of particular interest are also compounds (I) in which $R^3$ is hydrogen, amino, $(C_1-C_6)$alkyl, $(C_1-C_6)$alkoxy, $(C_2-C_6)$alkenyl, $(C_2-C_6)$alkynyl, $(C_3-C_6)$cycloalkyl, $(C_5-C_6)$cycloalkenyl, phenyl or heterocyclyl, where each of the eight last-mentioned radicals is unsubstituted or substituted by one or more radicals from the group consisting of halogen, hydroxyl, amino, nitro, formyl, carboxyl, cyano, thiocyanato, $(C_1-C_4)$alkoxy, $(C_1-C_4)$alkoxy-$(C_1-C_4)$alkoxy, hydroxy-$(C_1-C_4)$alkoxy, $(C_1-C_4)$alkoxy-poly(alkyleneoxy), hydroxy-poly(alkyleneoxy), $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, $(C_3-C_6)$cycloalkyl, phenylcarbonyl, phenoxycarbonyl, heterocyclyl, where each of the 6 last-mentioned radicals is unsubstituted or substituted by one or more radicals from the group consisting of halogen, CN, SCN, $NO_2$, $(C_1-C_4)$alkyl, $(C_1-C_4)$haloalkyl, $(C_1-C_4)$alkoxy and $(C_1-C_4)$haloalkoxy, and $(C_1-C_4)$alkylsulfonyl and $(C_1-C_4)$haloalkylsulfonyl and, in the case of cyclic radicals, also $(C_1-C_4)$alkyl and $(C_1-C_4)$haloalkyl, or an acyl radical of the formula -B*-A*, where A* is hydrogen or $(C_1-C_6)$alkyl, $(C_2-C_6)$alkenyl, $(C_2-C_6)$alkynyl, $(C_3-C_6)$cycloalkyl, $(C_5-C_6)$cycloalkenyl or phenyl, where each of the six last-mentioned radicals is unsubstituted or substituted by one or more radicals from the group consisting of halogen, hydroxyl, amino, nitro, formyl, carboxyl, cyano, thiocyanato, $(C_1-C_4)$alkoxy, $(C_1-C_4)$haloalkoxy, $(C_1-C_4)$alkylthio, mono$(C_1-C_4)$alkylamino, di$(C_1-C_4)$alkylamino, phenyl and $(C_3-C_6)$cycloalkyl, where each of the 2 last-mentioned radicals is unsubstituted or substituted by one or more radicals from the group consisting of halogen, CN, SCN, $NO_2$, $(C_1-C_4)$alkyl, $(C_1-C_4)$haloalkyl, $(C_1-C_4)$alkoxy and $(C_1-C_4)$haloalkoxy, and, in the case of cyclic radicals, also $(C_1-C_4)$alkyl and $(C_1-C_4)$haloalkyl, and B* is a divalent group of the formula —CO—, —CO—O—, —CO—NR'—, —S(O)$_p$— or —S(O)$_p$—O—, where p=0, 1 or 2 and R' is hydrogen, alkyl having 1 to 6 carbon atoms, phenyl, benzyl, cycloalkyl having 3 to 6 carbon atoms or alkanoyl having 1 to 4 carbon atoms, where -B*-A* including substituents has 1 to 12, preferably 1 to 10, carbon atoms and heterocyclyl is defined generally as for $R^1$ and $R^2$.

Also preferably, $R^3$ is hydrogen, amino, formyl, $(C_1-C_4)$alkyl, cyano-$(C_1-C_4)$alkyl, $(C_1-C_4)$haloalkyl, mono-, di- or polyhydroxy-$(C_1-C_4)$alkyl, hydroxy-poly[$(C_2-C_4)$alkyleneoxy]-$(C_1-C_4)$alkyl, mono-, di- or poly$(C_1-C_4)$alkoxy-$(C_1-C_4)$alkyl, $(C_1-C_4)$alkoxy-poly[$(C_2-C_4)$alkyleneoxy]-$(C_1-C_4)$alkyl, $(C_1-C_4)$haloalkoxy-$(C_1-C_4)$alkyl, $(C_2-C_6)$alkenyl, $(C_2-C_6)$haloalkenyl, $(C_2-C_6)$alkynyl, $(C_2-C_6)$haloalkynyl or aminocarbonyl or $(C_1-C_4)$alkylamino-$(C_1-C_4)$alkyl, di[$(C_1-C_4)$alkyl]amino-$(C_1-C_4)$alkyl, $(C_1-C_4)$alkylaminocarbonyl, di$(C_1-C_4)$alkylaminocarbonyl, $(C_1-C_5)$alkanoyl, [$(C_2-C_4)$alkenyl]carbonyl, [$(C_1-C_4)$alkoxy]carbonyl, $(C_2-C_4)$alkenyloxycarbonyl, aminocarbonyl-$(C_1-C_4)$ alkyl, $(C_1-C_4)$alkylaminocarbonyl-$(C_1-C_4)$alkyl, di[$(C_1-C_4)$alkyl]aminocarbonyl-$(C_1-C_4)$alkyl, $(C_1-C_4)$ alkoxycarbonyl-$(C_1-C_4)$alkyl, $(C_1-C_5)$alkanoyl-$(C_1-C_4)$ alkyl, [$(C_2-C_4)$alkenyl]carbonyl-$(C_1-C_4)$alkyl, [$(C_1-C_4)$ alkoxy]carbonyl-$(C_1-C_4)$alkyl or $(C_2-C_4)$ alkenyloxycarbonyl-$(C_1-C_4)$alkyl, where each of the 16 last-mentioned radicals is unsubstituted or substituted by one or more radicals from the group consisting of halogen, CN, $(C_1-C_4)$alkoxy and $(C_1-C_4)$haloalkoxy, or $(C_3-C_6)$cycloalkyl, $(C_3-C_6)$cycloalkylamino-$(C_1-C_4)$ alkyl, phenyl, phenylcarbonyl, phenoxycarbonyl, phenyl-carbonyl-$(C_1-C_4)$alkyl, phenoxy-$(C_1-C_4)$alkyl, phenyl-$(C_1-C_4)$alkyl, heterocyclyl, heterocyclyl-$(C_1-C_4)$alkyl or one of the 10 last-mentioned radicals which is substituted in the acylic moiety or, preferably, in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl and $(C_1-C_4)$ alkoxy, where hetercyclyl in the radicals contains in each case 3 to 9 ring atoms and 1 to 3 hetero ring atoms from the group consisting of N, O and S.

Here, preference is given to compounds (I) in which $R^3$ is hydrogen, $(C_1-C_6)$alkyl, $(C_3-C_6)$cycloalkyl or phenyl, where each of the three last-mentioned radicals is unsubstituted or substituted by one or more radicals from the group consisting of halogen, hydroxyl, amino, formyl, cyano, thiocyanato, $(C_1-C_4)$alkoxy, $(C_1-C_4)$haloalkoxy, $(C_1-C_4)$alkylthio, mono$(C_1-C_4)$alkylamino, di$(C_1-C_4)$ alkylamino and phenyl, which is unsubstituted or substituted by one or more radicals from the group consisting of halogen, $NO_2$, $(C_1-C_4)$alkyl, $(C_1-C_4)$haloalkyl, $(C_1-C_4)$ alkoxy and $(C_1-C_4)$haloalkoxy, and, in the case of cyclic radicals, also $(C_1-C_4)$alkyl and $(C_1-C_4)$haloalkyl, or an acyl radical of the formula -B*-A*, in which A* is hydrogen or $(C_1-C_6)$alkyl or phenyl, where each of the two last-mentioned radicals is unsubstituted or substituted by one or more radicals from the group consisting of halogen, $(C_1-C_4)$alkoxy, $(C_1-C_4)$haloalkoxy, phenyl and $(C_3-C_6)$cycloalkyl, where each of the 2 last-mentioned radicals is unsubstituted or substituted by one or more radicals from the group consisting of halogen, $(C_1-C_4)$alkyl, $(C_1-C_4)$haloalkyl, $(C_1-C_4)$alkoxy and $(C_1-C_4)$haloalkoxy and, in the case of cyclic radicals, also $(C_1-C_4)$alkyl and $(C_1-C_4)$haloalkyl, and B* is a divalent group of the formula —CO—, —CO—O—, —S(O)$_p$—, where p=0, 1 or 2 and R' is hydrogen or alkyl having 1 to 4 carbon atoms, where -B*-A* including substituents has 1 to 12, preferably 1 to 10, carbon atoms.

Examples of preferred acyl radicals of the formula -B*-A* are $(C_1-C_5)$alkanoyl, [$(C_1-C_4)$haloalkyl]carbonyl, [$(C_2-C_4)$alkenyl]carbonyl, [$(C_2-C_4)$haloalkenyl]carbonyl, $(C_1-C_4)$ alkoxy-$(C_1-C_4)$alkylcarbonyl, [$(C_1-C_4)$alkoxy]carbonyl, [$(C_1-C_4)$haloalkoxy]carbonyl, [$(C_2-C_4)$haloalkenyloxy]carbonyl, [$(C_1-C_4)$haloalkoxy]carbonyl, phenylcarbonyl, phenoxycarbonyl, benzylcarbonyl or benzyloxycarbonyl, where each of the 4 last-mentioned radicals is unsubstituted in the phenyl ring or substituted by one or more radicals from the group consisting of halogen, CN, SCN, $NO_2$, $(C_1-C_4)$alkyl, $(C_1-C_4)$haloalkyl, $(C_1-C_4)$alkoxy and $(C_1-C_4)$haloalkoxy, or $(C_1-C_4)$alkylsulfonyl or $(C_1-C_4)$haloalkylsulfonyl.

With particular preference, $R^3$ is hydrogen, amino, formyl, $(C_1-C_4)$alkyl, cyano-$(C_1-C_4)$ alkyl, $(C_1-C_4)$alkoxy-$(C_1-C_4)$alkyl, $(C_2-C_6)$alkenyl, halo-$(C_2-C_6)$alkenyl, $(C_2-C_6)$alkynyl or phenyl, $(C_1-C_4)$alkyl-carbonyl, $(C_1-C_4)$alkoxycarbonyl, aminocarbonyl, phenoxy-$(C_1-C_4)$alkyl, phenyl-$(C_1-C_4)$alkyl or one of the 6 last-mentioned radicals which is substituted in the acyclic moiety or, preferably, in the cyclic moiety by one or more radicals from the group consisting of halogen, $(C_1-C_4)$ alkyl and $(C_1-C_4)$alkoxy;

in particular hydrogen, methyl, ethyl, acetyl, methoxyacetyl, formyl, methoxymethyl, methoxyethyl, benzyl, 4-chlorobenzyl, benzoyl, phenyl or 4-chlorophenyl; especially hydrogen.

Of particular interest are also compounds (I) in which $R^4$ is a radical of the formula -$Z^1$-$R^6$, where $Z^1$ and $R^5$ are as defined below, $R^5$ are each independently of one another halogen, CN, SCN, $NO_2$, a radical of the formula -$Z^2$-$R^7$, where $Z^2$ and $R^7$ are as defined below, or two adjacent radicals $R^5$ together are a fused-on cycle having 4 to 6 ring atoms which is carbocyclic or contains 1 to 3 hetero ring atoms from the group consisting of O, S and N and which is unsubstituted or substituted by one or more radicals from the group consisting of halogen, $(C_1-C_4)$alkyl and oxo, and $R^6$ and $R^7$, $R^8$, $R^9$ are each independently of one another hydrogen, except that $R^7$ is not hydrogen if $Z^2$ is a direct bond, or an acyclic hydrocarbon radical having 1 to 10 carbon atoms, preferably $(C_1-C_4)$alkyl, $(C_2-C_6)$alkenyl or $(C_2-C_6)$alkynyl, or a cyclic hydrocarbon radical having 3 to 6 carbon atoms, preferably $(C_3-C_6)$cycloalkyl or $(C_5-C_6)$ cycloalkenyl, or a heterocyclic radical, which preferably has 3 to 6 ring atoms and 1 to 3 hetero ring atoms from the group consisting of N, O and S, where each of the last-mentioned carbon-containing radicals is unsubstituted or substituted by one or more radicals from the group consisting of halogen, hydroxyl, amino, nitro, formyl, aminocarbonyl, carboxyl, sulfonyl, cyano, thiocyanato, $(C_1-C_6)$ alkoxy, $(C_2-C_6)$alkenyloxy, $(C_2-C_6)$alkynyloxy, $(C_1-C_6)$ alkoxy-poly(alkyleneoxy), hydroxy-poly(alkyleneoxy), $(C_1-C_6)$alkylthio, mono- and di[$(C_1-C_6)$alkyl]amino, [$(C_1-C_6)$alkyl]carbonyl, [$(C_2-C_6)$alkenyl]carbonyl, [$(C_2-C_6)$ alkynyl]carbonyl, [$(C_1-C_6)$alkoxy]carbonyl, [$(C_2-C_6)$alkenyloxy]carbonyl, [$(C_2-C_6)$alkynyloxy]carbonyl, mono- and di[$(C_1-C_6)$alkyl]aminocarbonyl, phenyl, phenoxy, $(C_3-C_6)$cycloalkyl, phenylcarbonyl, phenoxycarbonyl, heterocyclyl, $(C_1-C_4)$alkylsulfonyl and, in the case of cyclic radicals, also $(C_1-C_4)$alkyl, where each of the 24 last-mentioned substituents is unsubstituted or substituted by one or more radicals from the group consisting of halogen, CN, SCN, $NO_2$, $(C_1-C_4)$ alkoxy, $(C_1-C_4)$alkylthio, $(C_1-C_4)$haloalkoxy, formyl, $(C_1-C_4)$alkylcarbonyl, [$(C_1-C_4)$haloalkyl]carbonyl, [$(C_1-C_4)$alkoxy]carbonyl, [$(C_1-C_4)$haloalkoxy]carbonyl and, in the case of cyclic radicals, also $(C_1-C_4)$alkyl and $(C_1-C_4)$haloalkyl, and, preferably, $R^6$ and $R^7$, $R^8$, $R^9$ are each independently of one another hydrogen, except that $R^7$ is not hydrogen if $Z^2$ is a direct bond, or an acyclic hydrocarbon radical having 1 to 10 carbon atoms, preferably $(C_1-C_4)$alkyl, $(C_2-C_6)$alkenyl or $(C_2-C_6)$alkynyl, or a cyclic hydrocarbon radical having 3 to 6 carbon atoms, preferably $(C_3-C_6)$cycloalkyl or $(C_5-C_6)$ cycloalkenyl, or a heterocyclic radical, which preferably has 3 to 6 ring atoms and 1 to 3 hetero ring atoms from the group consisting of N, O and S, where each of the last mentioned hydrocarbon-containing radicals is unsubstituted or substituted by one or more radicals from the group consisting of halogen, hydroxyl, amino, nitro, formyl, carboxyl, sulfonyl, cyano, thiocyanato, $(C_1-C_4)$alkoxy, $(C_1-C_4)$alkoxy-$(C_1-C_4)$alkoxy, hydroxy-$(C_1-C_4)$alkoxy, $(C_1-C_4)$alkoxy-poly(alkyleneoxy), hydroxy-poly (alkyleneoxy), $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, $(C_3-C_6)$cycloalkyl, phenylcarbonyl, phenoxycarbonyl, heterocyclyl, where each of the 6 last-mentioned radicals is unsubstituted or substituted by one or more radicals from the group consisting of halogen, CN, SCN, $NO_2$, $(C_1-C_4)$alkyl, $(C_1-C_4)$haloalkyl, $(C_1-C_4)$alkoxy and $(C_1-C_4)$haloalkoxy, and $(C_1-C_4)$alkylsulfonyl and $(C_1-C_4)$haloalkylsulfonyl and, in the case of cyclic radicals, also $(C_1-C_4)$alkyl and $(C_1-C_4)$haloalkyl, and in each case $Z^1$ and the groups $Z^2$ are each independently of one another a direct bond or a divalent group of the formula —O—, —S(O)$_p$—, —S(O)$_p$—O—, —O—S(O)$_p$—, —CO—, —O—CO—, —CO—O—, —NR'—, —O—NR'—, —NR'—O—, —NR'—CO—, —CO—NR'—, where p=0, 1 or 2 and R' is hydrogen, alkyl having 1 to 6 carbon atoms, phenyl, benzyl, cycloalkyl having 3 to 6 carbon atoms or alkanoyl having 1 to 6 carbon atoms, and, preferably, $Z^1$ and the groups $Z^2$ are each independently of one another a direct bond or a divalent group of the formula —O—, —S—, —SO$_2$—, —CO—, —O—CO—, —CO—O—, —NR'—, —NR'—CO—, —CO—NR'—, where R' is hydrogen, $(C_1-C_4)$alkyl or alkanoyl having 1 to 4 carbon atoms, where heterocyclyl in the radicals has in each case 3 to 9, preferably 3 to 6, ring atoms and 1 to 3 hetero ring atoms from the group consisting of N, O and S.

Moreover, preferably, $R^4$ is hydrogen, formyl, carboxyl, cyano, thiocyanato, aminocarbonyl, $(C_1-C_4)$alkyl, cyano-$(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 6 ring members where the cyclic groups in the 3 last-mentioned radicals are unsubstituted or substituted by one or more, preferably up to three, radicals from the group consisting of $(C_1-C_4)$alkyl, halogen and cyano, or phenyl, phenoxy, phenylcarbonyl, phenylcarbonyl-$(C_1-C_4)$alkyl, phenoxycarbonyl, $(C_1-C_4)$alkylcarbonyl, $(C_1-C_4)$alkoxycarbonyl, $(C_1-C_4)$alkylaminocarbonyl, $(C_1-C_4)$alkoxycarbonyl-$(C_1-C_4)$alkyl, $(C_1-C_4)$alkylaminocarbonyl-$(C_1-C_4)$alkyl, phenoxy-$(C_1-C_4)$alkyl, phenyl-$(C_1-C_4)$alkyl, heterocyclyl, heterocyclylamino, heterocyclyloxy, heterocyclylthio, $(C_1-C_5)$alkanoylamino, N-[$(C_1-C_5)$alkanoyl]-N-[$(C_1-C_4)$alkyl]amino, [$(C_2-C_4)$alkenyl]carbonylamino, [$(C_2-C_4)$alkynyl]carbonylamino, [$(C_1-C_4)$alkoxy]carbonylamino, [$(C_2-C_4)$alkenyloxy]carbonylamino, [$(C_2-C_4)$alkynyloxy]carbonylamino, phenylcarbonylamino, phenoxycarbonylamino, $(C_1-C_4)$alkylsulfonyl, $(C_2-C_4)$alkenylsulfonyl or one of the 27 last-mentioned radicals which is substituted in the acyclic moiety or, preferably, in the cyclic moiety by one or more radicals from the group consisting of halogen, nitro, cyano, $(C_1-C_4)$alkoxy, $(C_1-C_4)$alkylthio, $(C_1-C_4)$haloalkoxy, formyl, $(C_1-C_4)$alkylcarbonyl, $(C_1-C_4)$alkoxycarbonyl, $(C_1-C_4)$alkoxy and, in the case of cyclic moieties, also $(C_1-C_4)$alkyl and $(C_1-C_4)$haloalkyl, where heterocyclyl in the radicals has in each case 3 to 9 ring atoms and 1 to 3 hetero ring atoms from the group consisting of N, O and S.

Furthermore, preferably, $R^4$ is hydrogen, $(C_1-C_4)$alkyl, cyano-$(C_1-C_4)$alkyl, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, halo-$(C_2-C_6)$alkenyl, $(C_2-C_6)$alkynyl, $(C_1-C_4)$alkylamino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members, where the cyclic groups in the 3 last-mentioned radicals are unsubstituted or substituted by one or more, preferably up to three, radicals from the group consisting of $(C_1-C_4)$alkyl, halogen and cyano, or phenyl, phenoxy-$(C_1-C_4)$alkyl, phenyl-$(C_1-C_4)$alkyl, heterocyclyl, or one of the 4 last-mentioned radicals which is substituted in the acyclic moiety or, preferably, in the cyclic moiety by one or more radicals from the group consisting of halogen, nitro, cyano, $(C_1-C_4)$alkoxy, $(C_1-C_4)$alkylthio, $(C_1-C_4)$haloalkoxy, $(C_1-C_4)$alkylcarbonyl, $(C_1-C_4)$alkoxycarbonyl, $(C_1-C_4)$alkoxy and, in the case of cyclic moieties, also $(C_1-C_4)$alkyl and $(C_1-C_4)$haloalkyl, where heterocyclyl in the radicals contains in each case 3 to 9 ring atoms and 1 to 3 hetero ring atoms from the group consisting of N, O and S;

in particular $R^4$=hydrogen or $(C_1-C_4)$alkyl.

Of particular interest are furthermore compounds (I) in which $R^5$, if n=1, and the radicals $R^5$ in each case independently of one another, if n is greater than 1, is/are halogen, hydroxyl, amino, nitro, formyl, carboxyl, cyano, thiocyanato, aminocarbonyl, $(C_1-C_4)$alkyl, cyano-$(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 6 ring members, where the cyclic groups in the 3 last-mentioned radicals are unsubstituted or substituted by one or more radicals, preferably up to three radicals, from the group consisting of $(C_1-C_4)$alkyl, halogen and cyano, or phenyl, phenoxy, phenylcarbonyl, phenylcarbonyloxy, phenylcarbonyl-$(C_1-C_4)$alkyl, phenoxycarbonyl, $(C_1-C_4)$alkylcarbonyl, $(C_1-C_4)$alkoxycarbonyl, $(C_1-C_4)$alkylaminocarbonyl, $(C_1-C_4)$alkoxycarbonyl-$(C_1-C_4)$alkyl, $(C_1-C_4)$alkylaminocarbonyl-$(C_1-C_4)$alkyl, phenoxy-$(C_1-C_4)$alkyl, phenyl-$(C_1-C_4)$alkyl, heterocyclyl, heterocyclylamino, heterocyclyloxy, heterocyclylthio, $(C_1-C_5)$alkanoylamino, N-[$(C_1-C_5)$alkanoyl]-N-[$(C_1-C_4)$alkyl]amino, [$(C_2-C_4)$alkenyl]carbonylamino, [$(C_2-C_4)$alkynyl]carbonylamino, [$(C_1-C_4)$alkoxy]carbonylamino, [$(C_2-C_4)$alkenyloxy]carbonylamino, [$(C_2-C_4)$alkynyloxy]carbonylamino, phenylcarbonylamino, phenoxycarbonylamino, $(C_1-C_4)$alkylsulfonyl, $(C_2-C_4)$alkenylsulfonyl or one of the 28 last-mentioned radicals which is substituted in the acyclic moiety or, preferably, in the cyclic moiety by one or more radicals from the group consisting of halogen, nitro, cyano, $(C_1-C_4)$alkoxy, $(C_1-C_4)$alkylthio, $(C_1-C_4)$haloalkoxy, formyl, $(C_1-C_4)$alkylcarbonyl, $(C_1-C_4)$alkoxycarbonyl, $(C_1-C_4)$alkoxy and, in the case of cyclic moieties, also $(C_1-C_4)$alkyl and $(C_1-C_4)$haloalkyl, where heterocyclyl in the radicals contains in each case 3 to 9 ring atoms and 1 to 3 hetero ring atoms from the group consisting of N, O and S, or two adjacent radicals $R^5$ together are a fused-on cycle having 4 to 6 ring atoms which is carbocyclic or contains 1 to 3 hetero ring atoms from the group consisting of O, S and N and which is unsubstituted or substituted by one or more radicals from the group consisting of halogen, $(C_1-C_4)$alkyl and oxo.

Furthermore, preferably, $R^5$, if n=1, and the radicals $R^5$ in each case independently of one another, if n is greater than 1, is/are halogen, hydroxyl, amino, nitro, formyl, carboxyl, cyano, thiocyanato, aminocarbonyl, $(C_1-C_4)$alkyl, cyano-$(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, $(C_2-C_6)$alkenyl, $(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members where the cyclic groups in the 3 last-mentioned radicals are unsubstituted or substituted by one or more radicals, preferably up to three radicals, from the group consisting of $(C_1-C_4)$alkyl, halogen and cyano, or phenyl, phenoxy, phenylcarbonyl, phenylcarbonyloxy, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, $(C_1-C_4)$alkylaminocarbonyl, phenoxy-$(C_1-C_4)$alkyl, phenyl-$(C_1-C_4)$alkyl, heterocyclyl, heterocyclylamino, heterocyclyloxy, heterocyclylthio, $(C_1-C_5)$alkanoylamino, N-[$(C_1-C_5)$alkanoyl]-N-[$(C_1-C_4)$alkyl]amino, phenylcarbonylamino, phenoxycarbonylamino, $(C_1-C_4)$alkylsulfonyl, $(C_2-C_4)$alkenylsulfonyl or one of the 22 last-mentioned radicals which is substituted in the acyclic moiety or, preferably, in the cyclic moiety by one or more radicals from the group consisting of halogen, nitro, cyano, $(C_1-C_4)$alkoxy, $(C_1-C_4)$alkylthio, $(C_1-C_4)$alkylcarbonyl, $(C_1-C_4)$alkoxycarbonyl, $(C_1-C_4)$alkoxy and, in the case of cyclic moieties, also $(C_1-C_4)$alkyl and $(C_1-C_4)$haloalkyl, where heterocyclyl in the radicals contains in each case 3 to 6 ring atoms and 1 to 3 hetero ring atoms from the group consisting of N, O and S, or two adjacent radicals $R^5$ together are a fused-on cycle having 4 to 6 ring atoms which is carbocyclic or contains 1 to 3 hetero ring atoms from the group consisting of O, S and N and which is unsubstituted or substituted by one or more radicals from the group consisting of halogen, $(C_1-C_4)$alkyl and oxo.

Furthermore, preferably, $R^5$, if n=1, and the radicals $R^5$ in each case independently of one another, if n is greater than 1, is/are halogen, hydroxyl, amino, nitro, formyl, cyano, aminocarbonyl, $(C_1-C_4)$monoalkylaminocarbonyl, $(C_1-C_4)$dialkylaminocarbonyl, $(C_1-C_4)$alkyl, cyano-$(C_1-C_4)$alkyl, $(C_1-C_4)$alkoxy, $(C_1-C_4)$alkylamino, halo-$(C_1-C_4)$alkyl, hydroxy-$(C_1-C_4)$alkyl, $(C_1-C_4)$alkoxy-$(C_1-C_4)$alkyl, $(C_2-C_4)$alkenyl, $(C_2-C_4)$alkynyl, $(C_1-C_4)$alkylamino-$(C_1-C_4)$alkyl, di[$(C_1-C_4)$alkyl]amino-$(C_1-C_4)$alkyl, or

[$(C_1-C_4)$alkyl]carbonyl, [$(C_1-C_4)$haloalkyl]carbonyl, [$(C_1-C_4)$alkoxy-$(C_1-C_4)$alkyl]carbonyl, formylamino, [$(C_1-C_4)$alkyl]carbonylamino, [$(C_1-C_4)$haloalkyl]carbonylamino, phenyl, phenoxy, phenylcarbonyl, phenylcarbonylamino, heterocyclyl or one of the 5 last-mentioned radicals which is substituted by one or more radicals from the group consisting of halogen, $(C_1-C_4)$alkyl, $(C_1-C_4)$haloalkyl, $(C_1-C_4)$alkoxy, $(C_1-C_4)$haloalkoxy and $(C_1-C_4)$alkylthio, in particular $R^5$=halogen, preferably F, Cl or Br, hydroxyl, formyl, cyano, $(C_1-C_4)$alkyl, for example methyl, ethyl or isopropyl, or $(C_1-C_4)$alkoxy, for example methoxy, ethoxy or isopropoxy, or $(C_1-C_4)$alkylamino, $(C_1-C_4)$haloalkyl, $(C_2-C_4)$alkenyl, $(C_2-C_4)$alkynyl, [$(C_1-C_4)$alkyl]carbonyl, for example acetyl, [$(C_1-C_4)$haloalkyl]carbonyl, for example trifluoroacetyl, or formylamino, [$(C_1-C_4)$alkyl]carbonylamino or benzoylamino.

The particularly preferred meanings of $R^6$ and $R^7$ result correspondingly from the preferred meanings for $R^4$ and $R^5$.

Of particular interest are also compounds (I) in which $R^8$ and $R^9$ are each independently of one another hydrogen, formyl, carboxyl, cyano, thiocyanato, aminocarbonyl, $(C_1-C_4)$alkyl, cyano-$(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 6 ring members, where the cyclic groups in the 3 last-mentioned radicals are unsubstituted or substituted by one or more, preferably up to three radicals from the group consisting of $(C_1-C_4)$alkyl, halogen and cyano, or phenyl, phenoxy, phenylcarbonyl, phenylcarbonyl-$(C_1-C_4)$alkyl, phenoxycarbonyl, $(C_1-C_4)$alkylcarbonyl, $(C_1-C_4)$alkoxycarbonyl, $(C_1-C_4)$alkylaminocarbonyl, $(C_1-C_4)$alkoxycarbonyl-$(C_1-C_4)$alkyl, $(C_1-C_4)$alkylaminocarbonyl-$(C_1-C_4)$alkyl, phenoxy-$(C_1-C_4)$alkyl, phenyl-$(C_1-C_4)$alkyl, heterocyclyl, heterocyclylamino, heterocyclyloxy, heterocyclylthio, $(C_1-C_5)$alkanoylamino, N-[$(C_1-C_5)$alkanoyl]-N-[$(C_1-C_4)$alkyl]amino, [$(C_2-C_4)$alkenyl]carbonylamino, [$(C_2-C_4)$alkynyl]carbonylamino, [$(C_1-C_4)$alkoxy]carbonylamino, [$(C_2-C_4)$alkenyloxy]carbonylamino, [$(C_2-C_4)$alkynyloxy]carbonylamino, phenylcarbonylamino, phenoxycarbonylamino, $(C_1-C_4)$alkylsulfonyl, $(C_2-C_4)$alkenylsulfonyl or one of the 27 last-mentioned radicals which is substituted in the acyclic moiety or, preferably, in the cyclic moiety by one or more radicals from the group consisting of halogen, nitro, cyano, $(C_1-C_4)$alkoxy, $(C_1-C_4)$alkylthio, $(C_1-C_4)$haloalkoxy, formyl, $(C_1-C_4)$alkylcarbonyl, $(C_1-C_4)$alkoxycarbonyl, $(C_1-C_4)$alkoxy and, in the case of cyclic moieties, also $(C_1-C_4)$alkyl and $(C_1-C_4)$haloalkyl, where heterocyclyl in the radicals has preferably in each case 3 to 9 ring atoms and 1 to 3 hetero ring atoms from the group consisting of N, O and S.

Furthermore, preferably, $R^8$ and $R^9$ are each independently of one another hydrogen, $(C_1-C_4)$alkyl, cyano-$(C_1-C_4)$alkyl, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_2-C_6)$alkenyl, halo-$(C_2-C_6)$alkenyl, $(C_2-C_6)$alkynyl, $(C_1-C_4)$alkylamino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 9 ring members, where the cyclic groups in the 3 last-mentioned radicals are unsubstituted or substituted by one or more, preferably up to three, radicals from the group consisting of $(C_1-C_4)$alkyl, halogen and cyano, or phenyl, phenoxy-$(C_1-C_4)$alkyl, phenyl-$(C_1-C_4)$alkyl, heterocyclyl, or one of the 4 last-mentioned radicals which is substituted in the acyclic moiety or, preferably, in the cyclic moiety by one or more radicals from the group consisting of halogen, nitro, cyano, $(C_1-C_4)$alkoxy, $(C_1-C_4)$alkylthio, ($C_1$-$C_4$)haloalkoxy, ($C_1$-$C_4$)alkylcarbonyl, ($C_1$-$C_4$)alkoxycarbonyl, ($C_1$-$C_4$)alkoxy and, in the case of cyclic moieties, also ($C_1$-$C_4$)alkyl and ($C_1$-$C_4$)haloalkyl, where heterocyclyl in the radicals contains preferably in each case 3 to 9 ring atoms and 1 to 3 hetero ring atoms from the group consisting of N, O and S; in particular, $R^8$ and $R^9$ are, independently of one another, hydrogen or ($C_1$-$C_4$)alkyl.

Of particular interest are also compounds (I) in which
$X^1$, $X^2$, $X^3$, $X^4$ are each independently of one another a carbon atom which is substituted by a hydrogen atom or one of the substituents $R^5$ defined above, or a nitrogen atom, or two adjacent symbols $X^1$, $X^2$, $X^3$ and $X^4$ are in each case together a divalent group of the formula —O—, —S—, —NH— or —NR—, where R is as defined for $R^3$, and is preferably hydrogen or ($C_1$-$C_4$)alkyl provided the groups $X^1$, $X^2$, $X^3$, $X^4$ together with the attached $C_2$ unit of the fused-on ring form a carbocyclic or heterocyclic aromatic five- or six-membered ring, $(Y^1)_m$ are m divalent groups $Y^1$, where each group $Y^1$ independently of the other radicals $Y^1$ is a group of the formula —O—, —CO—, —C(=NR*)—, —S(O)$_q$—, —NR*— or —N(O)—, where q=0, 1 or 2 and R* is as defined for $R^3$ and preferably hydrogen, ($C_1$-$C_4$)alkyl, benzyl or phenyl, in particular hydrogen, ($C_1$-$C_4$)alkyl or phenyl, or a group of the formula $CR^8R^9$ already defined above, and $Y^1$ is preferably a group of the formula $CR^8R^9$, in particular $CH_2$, $CH(CH_3)$, $CH(C_2H_5)$, $CH(CH_3)_2$ or $CH(C_6H_5)$ and m=0, 1, 2 or 3, in particular m=1 or 2, and
$(Y^1)_m$ is preferaby $CH_2$, $CH_2CH_2$, $CH_2CH_2CH_2$, $CH(CH_3)$, $CH(CH_3)CH_2$, $CH_2CH(CH_3)$, $CH(CH_3)_2CH_2$, $CH(C_2H_5)CH_2$, or $CH_2CH(C_6H_5)$, $Y^2$ is a group as defined for $Y^1$ or a direct bond, preferably a direct bond or a group of the formula —O—, —S—, $CH_2$, $CH(CH_3)$ or ($C_1$-$C_4$)alkylamino, for example $N(CH_3)$, $N(C_2H_5)$, N(n-$C_3H_7$) or N(i-$C_3H_7$), or $N(CH_2C_6H_5)$ or $N(C_6H_5)$, where two adjacent groups of the symbol pairs $Y^1$ and $Y^1$ or of the symbol pairs $Y^1$ and $Y^2$ are groups without heteroatoms of the same meaning, and where the groups $(Y^1)_m$ and $Y^2$ together with the attached $C_2$ unit of the aromatic ring and the carbon atom attached to $R^4$ form a fused-on carbocyclic or heterocyclic nonaromatic, four- to eight-membered ring.

If one pair of adjacent symbols X together is a divalent group of the formula —O—, —S—, —NH— or —NR— mentioned, the double bonds in the heteroaromatic radical are fixed. In this case, the formula (I) embraces the substructures (I-A) and (I-B):

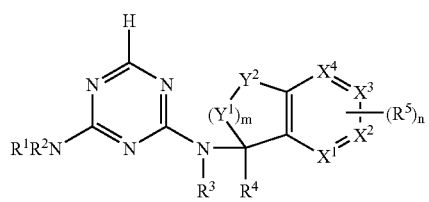
(I-A)

-continued

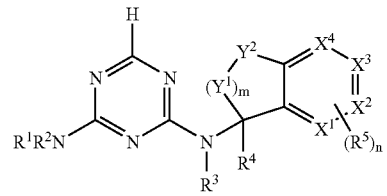
(I-B)

Suitable bases for aromatic carbocyclic or heterocyclic rings in the bicyclic system are, for example, the following:

benzene, pyridine, pyrimidine, pyrazine, pyridazine, pyrrole, pyrazole, imidazole, furan, thiazole, oxazole, isoxazole, thiophene, thiazole.

Preference is also given to compounds of the formula (I) and salts thereof in which one or more or all of the radicals and symbols from the group consisting of $R^1$, $R^2$, $R^3$, $R^4$, $R^5$, $R^6$, $R^7$, $R^8$, $R^9$, $X^1$, $X^2$, $X^3$, $X^4$, $Y^1$, $Y^2$, n and m have in each case one of the abovementioned preferred or particularly preferred meanings and, in particular, also meanings as they occur in the radicals of the examples in the tables further below.

The present invention also provides a process for preparing the compounds of the general formula (I) or salts thereof, which comprises a) reacting a compound of the formula (II)

in which $R^{13}$ is a functional group from the group of the carboxylic esters, carboxylic orthoesters, carbonyl chlorides, carboxamides and carboxylic anhydrides with a biguamide of the formula (III) or an acid addition salt thereof

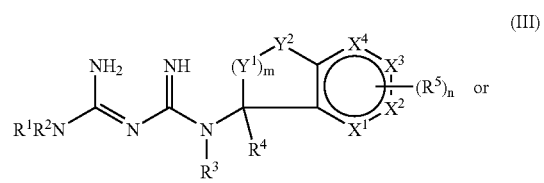
(III)

b) reacting a compound of the formula (IV)

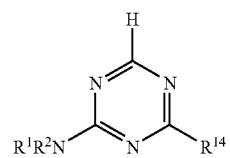
(IV)

in which $R^{14}$ is an exchangeable radical or a leaving group, for example chlorine, trichloromethyl, ($C_1$-$C_4$)alkylsulfonyl or unsubstituted or substituted phenyl-($C_1$-$C_4$)alkylsulfonyl or ($C_1$-$C_4$)alkylphenylsulfonyl, with a suitable amine of the formula (V) or an acid addition salt thereof

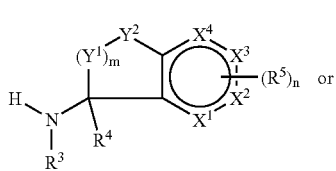

(V)

c) reacting a diamino-1,3,5-triazine of the formula (VI) with an isocyanate of the formula (VII)

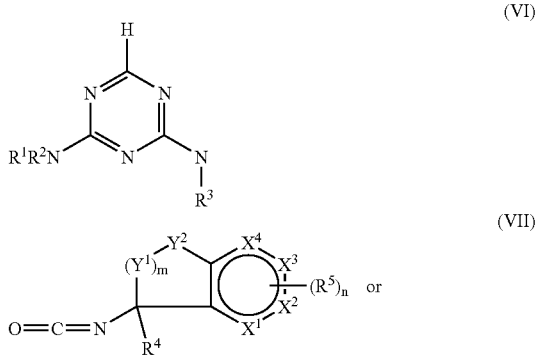

d) removing, in a triazine of the structure (VII), the radical $R^{15}$, which is a leaving group or a radical that can be removed, using suitable processes, such as, for example, by hydrogenation of a radical which can be removed by hydrogenation or a leaving group $R^{15}$, if this is, for example, chlorine or a radical attached via sulfur,

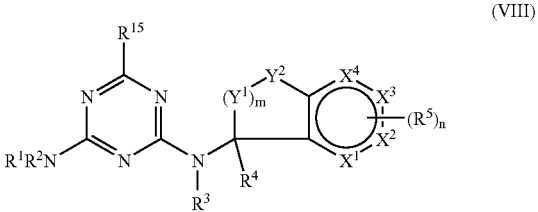

where in the formulae (II), (III), (IV), (V), (VI), (VII) and (VIII) the radicals $R^1$, $R^2$, $R^3$, $R^4$, $R^5$, $X^1$, $X^2$, $X^3$, $X^4$, $Y^1$ and $Y^2$ and the symbols m and n are as defined in formula (I).

The reaction of the compounds of the formula (II) and (III) is preferably carried out in a base-catalyzed manner in an inert organic solvent, such as, for example, tetrahydrofuran (THF), dioxane, acetonitrile, dimethylformamide (DMF), methanol and ethanol, at temperatures between −10° C. and the boiling point of the solvent, preferably from 20° C. to 60° C.; if acid addition salts of the formula (III) are used, these are generally released in situ with the aid of a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases, such as triethylamine or 1,8-diazabicyclo[5.4.0]undec-7-ene (DBU). The base in question is employed, for example, in a range of from 0.1 to 5 molar equivalents, based on the compound of the formula (III). The compounds of the formula (II) can be employed, for example, in equimolar amounts or in an excess of up to 10 molar equivalents, based on the compound of the formula (III). Analogous processes are known from the literature (compare: Shapiro, S. L.; Pamino, V. A.; Geiger, K.; Kobrin, S.; Freedman, L.; J Am Chem Soc, 1957, 79, 5664).

The reaction of the compounds of the formulae (IV) and (V) is preferably carried out with base catalysis in an inert organic solvent, such as, for example, THF, dioxane, acetonitrile, DMF, methanol and ethanol, at temperatures between −10° C. and the boiling point of the solvent or solvent mixture in question, preferably at from 20° C. to 150° C., in particular from 200° C. to 60° C. (if a reaction is initated at this temperature), where the compound (V), if employed as acid addition salt, is, if appropriate, released in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases, such as triethylamine or 1,8-diazabicyclo[5.4.0]undec-7-ene (DBU). The base in question is generally employed in a range of from 1 to 3 molar equivalents, based on the compound of the formula (IV); the compound of the formula (IV) can be employed, for example, in an amount equimolar to that of the compound of the formula (V) or in an excess of up to 2 molar equivalents. Analogous processes are known from the literature (cf. Comprehensive Heterocyclic Chemistry, A. R. Katritzky, C. W. Rees, Pergamon Press, Oxford, N.Y., 1984, Vol. 3; Part 2B; ISBN 0-08-030703-5, p. 482).

The reaction of the diamino-1,3,5-triazines of the formula (VI) with isocyanates of the formula (VII) is preferably carried out in a base-catalyzed manner in an inert organic solvent, such as, for example, tetrahydrofuran (THF), dioxane, acetonitrile, dimethylformamide (DMF), at temperatures between −10° C. and the boiling point of the solvent, preferably from 20° C. to 60° C. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases, such as triethylamine or 1,8-diazabicyclo[5.4.0]undec-7-ene (DBU). The base in question is employed, for example, in a range of from 0.5 to 3 molar equivalents, based on the compound of the formula (VI). The compound of the formula (VII) can be employed, for example, in an equimolar amount or in a slight excess, based on the compound of the formula (VI). In principle, the corresponding processes for acyclic and aromatic derivatives are known from the literature (cf. B. Singh; Heterocycles, 1993, 34, pp. 929-935).

The radical $R^{15}$ of the diamino-1,3,5-triazines of the formula (VIII) is preferably removed by an optionally acid-catalyzed hydrogenation with the aid of a suitable hydrogenation catalyst, such as, for example, Raney nickel or noble metal catalysts, such as palladium or platinum, on a suitable support, such as, for example, activated carbon, in an inert organic solvent, such as, for example, tetrahydrofuran (THF), dioxane, suitable alcohols, such as ethanol, acetic acid, or else mixtures thereof, at temperatures between −10° C. and the boiling point of the solvent, preferably from 20° C. to 60° C., where hydrogen is, in an apparatus suitable for this purpose, introduced into the reaction mixture or the reaction mixture is exposed to a hydrogen atmosphere under elevated pressure. Corresponding processes are known from the literature (Hirt, R.; Nidecker, H.; Berchtold, R.; Helv. Chim. Acta.; 1950, 33, 1365).

The starting materials of the formulae (II), (III), (IV), (V), (VI), (VII) and (VIII) are either commercially available or can be prepared by or analogously to processes known from the literature. The compounds can also be prepared, for example, by one of the processes described below.

If appropriate, the compounds of the formula (III) can be prepared by reacting cyanoguanidine with amines of the formula (V) or salts thereof. To this end, it is possible, for example, to heat both components in an inert solvent such as dichlorobenzene to 100 to 190° C., and the resulting biguanidines can then be isolated as salts by filtration with suction. Corresponding processes are described, for example, in S. L. Shapiro, V. A. Pamino, L. Freedmann; JACS 81, (1959), p. 3728 or H. M. Eisa, A. S. Tantawy, M. M. El-Kerdawy; Pharmazie 46, (1991) pp. 182 ff. If appropriate, the reactions can be catalyzed by addition of metal salts such as copper(II) sulfate, zinc(II) chloride or iron(II) chloride (T. Suyama, T. Soga, K. Miauchi; NIPPON KAGAKU KAISHI (1989), (5), pp. 884-887), and in most cases the reaction can then be carried out at lower temperatures in the range from 50° C. to the reflux temperature of the solvents in question. If appropriate, the reaction can also be carried out in a plurality of solvents such as THIF, dioxane, alcohols or ethers.

The amines which correspond to the formula (V) can also be prepared, for example, by hydrogenation of the corresponding oximes which for their part can be prepared from the corresponding ketones. A. B. Seen, S. B. Singh; J. Ind. Chem. Soc.; 43 (1966), p. 521, for example, describe a corresponding process where the conversion of sodium to sodium ethoxide is utilized as a source of hydrogen. Furthermore, Sarges et al.; J. Med. Chem.; 16, (1973), pp. 1003, 1008 describe a process for converting a ketone into the oxime which is then hydrogenated with palladium catalysis to give the corresponding amine hydrochloride. Hydrogenations with Raney nickel (cf.: D. Barbry, D. Couturier, N. Abdellatifi, D. Lesieur, C. Lespagnol; J. Heterocycl. Chem.; 28, (1991), p. 449) or hydrogenations with borohydride compounds (A. K. Gosh, S. P. McKee, W. M. Sanders; Tetrahedron Lett. 32, (1991), pp. 711-714) and other processes have also been described for corresponding bicyclic derivatives and can be used for synthesizing amines of the formula (V).

The compound of the formula (IV), or a direct precursor thereof, can be prepared, for example, as follows:

1. By reaction of a compound of the formula (II) with an amidinothiourea derivative of the formula (IX)

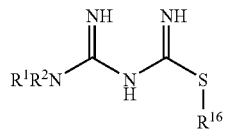

(IX)

where $R^{16}$ is $(C_1-C_4)$alkyl or phenyl-$(C_1-C_4)$alkyl and $R^1$ and $R^2$ are as defined in formula (I), giving compounds of the formula (IV) in which $R^{14}=-SR^{16}$.

2. By reaction of an amidine of the formula (X) or an acid addition salt thereof

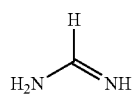

(X)

with an N-cyanodithioiminocarbonate of the formula (XI)

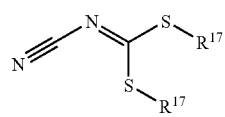

(XI)

where $R^{17}$ is $(C_1-C_4)$alkyl or phenyl-$(C_1-C_4)$alkyl, giving compounds of the formula (IV) in which $R^{14}=-S-R^{17}$.

3. By reaction of an alkali metal dicyanamide with a carboxylic acid derivative of the formula (II) mentioned above, giving compounds of the formula (VI) in which $R^{14}=NH_2$.

If appropriate, it is also possible, analogously to the processes listed above under 1.-3., to prepare intermediates of the formula (XII)

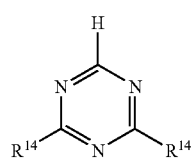

(XII)

having 2 exchangeable groups $R^{14}$ (cf. formula (IV)) and to substitute the exchangeable groups successively with suitable amines or ammonia to give, analogously to generally known procedures, compounds of the formula (I). It is also possible to modify commercially available compounds or compounds of the formula (XII) which can be prepared by other processes in a corresponding manner. If appropriate, intermediates of the formula (IV) or (XII), obtained analogously to the processes above under 1.-3., where $R^{14}$ is $(C_1-C_4)$alkylthio or phenyl-$(C_1-C_4)$alkylthio, can be converted by chlorination or oxidation into more reactive derivatives of the formulae (IV) and (XII), respectively.

The reaction of the carboxylic acid derivatives of the formula (II) with the amidinothiourea derivatives of the formula (VIII) is preferably carried out in a base-catalyzed manner in an organic solvent, such as, for example, acetone, THF, dioxane, acetonitrile, DMF, methanol, ethanol, at temperatures of from -10° C. to the boiling point of the solvent, preferably at from 0° C. to 20° C. However, the reaction can also be carried out in water or in aqueous solvent mixtures which contain one or more of the abovementioned organic solvents. If (VI) is used as acid addition salt, it can, if appropriate, be released in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases, such as triethylamine or 1,8-diazabicyclo [5.4.0]undec-7-ene (DBU). The base in question is employed in a range of from 1 to 10 molar equivalents, based on the compound of the formula (VII). Compounds of the formulae (II) and (VIII) can be employed, for example, in equimolar amounts or in an excess of up to 2 molar equivalents of compound of the formula (II). Analogous processes are known from the literature (cf.: H. Eilingsfeld, H. Scheuermann, Chem. Ber.; 1967, 100, 1874).

The reaction of the amidines of the formula (IX) with the N-cyanodithioimino-carbonates of the formula (X) is preferably carried out in a base-catalyzed manner in an inert organic solvent, such as, for example, acetonitrile, DMF, dimethylacetamide (DMA), N-methylpyrrolidone (NMP), methanol and ethanol, at temperatures of from −10° C. to the boiling point of the solvent, preferably from 20° C. to 80° C. If (VII) is used as acid addition salt, it can, if appropriate, be released in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases, such as triethylamine or 1,8-diazabicyclo [5.4.0]undec-7-ene (DBU). The base in question is employed in a range of from 1 to 3 molar equivalents, based on the compound of the formula (X). Compounds of the formulae (IX) and (X) can generally be employed in equimolar amounts or in an excess of 2 molar equivalents of the compound of the formula (II). Analogous processes are known from the literature (cf.: T. A. Riley, W. J. Henney, N. K. Dailey, B. E. Wilson, R. K. Robins; J. Heterocyclic Chem.; 1986, 23 (6), 1706-1714).

Intermediates of the formula (XII) where $R^{14}$=chlorine can be prepared by reacting an alkali metal dicyanamide with a carboxylic acid derivative of the formula (II), where $R^{13}$ is preferably the functional group carbonyl chloride or carboxamide. The reaction of the reaction components is carried out, for example, with acid catalysis in an inert organic solvent, such as, for example, toluene, chlorobenzene or a chlorinated hydrocarbon, at temperatures between −10° C. and the boiling point of the solvent, preferably at from 20° C. to 80° C., where the intermediates formed can be chlorinated in situ using a suitable chlorinating agent, such as, for example, phosphorus oxychloride. Suitable acids are, for example, hydrohalic acids, such as HCl, or else Lewis acids, such as, for example, $AlCl_3$ or $BF_3$ (cf. U.S. Pat. No. 5,095,113, DuPont and literature cited therein).

Intermediates of the formula (IV) or (XII), in which $R^{14}$= $(C_1$-$C_4)$alkylmercapto or unsubstituted phenyl-$(C_1$-$C_4)$alkylmercapto can be converted in an inert organic solvent, such as, for example, toluene, chlorobenzene or a chlorinated hydrocarbon or another solvent, at temperatures between −40° C. and the boiling point of the solvent, preferably at from 20° C. to 80° C., with a suitable chlorinating agent, such as, for example, elemental chlorine or phosphorus oxychloride, into more reactive chlorotriazines of the formula (IV) or (X), respectively, where $R^{14}$=Cl (cf. J. K. Chakrabarti, D. E. Tupper; Tetrahedron 1975, 31(16), 1879-1882).

Intermediates of the formula (IV) or (XI I), where $R^{14}$= $(C_1$-$C_4)$alkylmercapto or unsubstituted or substituted phenyl-$(C_1$-$C_4)$alkylmercapto or $(C_1$-$C_4)$alkylphenylthio can be oxidized in a suitable solvent, such as, for example, a chlorinated hydrocarbon, acetic acid, water, an alcohol, acetone or a mixture thereof, at temperatures between 0° C. and the boiling point of the solvent, preferably at from 20° C. to 80° C., using a suitable oxidizing agent, such as, for example, m-chloroperbenzoic acid, hydrogen peroxide, potassium peroxomonosulfate (cf.: T. A. Riley, W. J. Henney, N. K. Dailey, B. E. Wilson, R. K. Robins; J. Heterocyclic Chem.; 1986, 23 (6), 1706-1714).

Compounds of the formula (IV) are also obtained by selective nucleophilic substitution of an exchangeable group in compounds of the formula (XII) where $R^{14}$ is, for example, halogen, perhalomethyl, $(C_1$-$C_4)$alkylsulfinyl, $(C_1$-$C_4)$alkylsulfonyl or another leaving group known from the literature, in a suitable solvent, such as, for example, THF, dioxane, an alcohol, DMF or acetonitrile or a mixture thereof, at temperatures between −10° C. and the boiling point of the solvent, preferably at from 10° C. to 25° C., if appropriate under basic conditions. Suitable bases are alkali metal hydroxides, alkali metal hydrides, alkali metal carbonates, alkali metal alkoxides, alkaline earth metal hydroxides, alkaline earth metal hydrides, alkaline earth metal carbonates or organic bases, such as triethylamine or 1,8-diazabicyclo[5.4.0]undec-7-ene (DBU). The base in question is employed in a range of from 1 to 3 molar equivalents, based on the compound of the formula (XII); the nucleophile is generally employed in equimolar amounts or in an excess of up to 2 molar equivalents and may for its part, if appropriate, also be used as base. Analogous processes are known from the literature (cf.: V. I. Kaelarev, Dibi Ammar, A. F. Lunin; Ximinya Geterosikl. Soedin., 1985, N11, 1557-1563).

A collection of compounds (I) which can be synthesized by the abovementioned processes can additionally be prepared in parallelized fashion, which can be effected manually, partly automated or fully automated. In this context, it is possible to automate the procedure of the reaction, work-up or purification of the products or intermediates. In total, this is to be understood as meaning a procedure which is described, for example, by S. H. DeWitt in "Annual Reports in Combinatorial Chemistry and Molecular Diversity: Automated Synthesis", Volume 1, published by Escom, 1997, pages 69 to 77.

For carrying out the reaction and work-up in parallelized fashion, a series of commercially available apparatuses can be used as they are available from, for example, Stem Corporation, Woodrolfe Road, Tollesbury, Essex, CM9 8SE, England or H+P Labortechnik GmbH, Bruckmannring 28, 85764 Oberschleißheim, Germany. To carry out the parallelized purification of compounds (I) or of intermediates obtained during the preparation, there are available, inter alia, chromatographic equipment, for example from ISCO, Inc., 4700 Superior Street, Lincoln, Nebr. 68504, USA. The equipment mentioned makes possible a modular procedure, where the individual steps are automated, but manual operations have to be carried out between the steps. This can be circumvented by employing partly or fully integrated automation systems, in which the automation modules in question are operated by, for example, robots. Such automation systems can be obtained from, for example, Zymark Corporation, Zymark Center, Hopkinton, Mass. 01748, USA.

In addition to the above-described methods, compounds (I) can be prepared in full or partly by solid-phase supported methods. To this end, individual intermediates or all intermediates of the synthesis or of a synthesis adapted to the procedure in question are bound to a synthesis resin. Solid-phase supported synthetic methods are described extensively in the specialist literature, for example: Barry A. Bunin in "The Combinatorial Index", published by Academic Press, 1998.

The use of solid-phase supported synthesis methods permits a series of protocols known from the literature which, in turn, can be carried out manually or in an automated fashion. For example, the "teabag method" (Houghten, U.S. Pat. No. 4,631,211; Houghten et al., Proc. Natl. Acad. Sci., 1985, 82, 5131-5135) can be partly automated with products of IRORI, 11149 North Torrey Pines Road, La Jolla, Calif. 92037, USA. Solid-phase supported parallel synthesis can be automated successfully for example using equipment by Argonaut Technologies, Inc., 887 Industrial Road, San Carlos, Calif. 94070, USA or MultiSynTech GmbH, Wullener Feld 4, 58454 Witten, Germany.

The preparation in accordance with the processes described herein yields compounds (I) in the form of substance collections or substance libraries. Subject matter of the present invention are therefore also libraries of the compounds (I) which contain at least two compounds (I), and of their precursors.

Suitable for preparing the acid addition salts of the compounds of the formula (I) are the following acids: hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, maleic acid, succinic acid, fumaric acid, tartaric acid, citric acid, salicylic acid, sorbic acid or lactic acid, and also sulfonic acids, such as p-toluenesulfonic acid or 1,5-naphthalenedisulfonic acid. The acid addition compounds of the formula (I) can be obtained in a simple manner using the customary methods for forming salts, for example by dissolving a compound of the formula (I) in a suitable organic solvent, such as, for example, methanol, acetone, methylene chloride or petroleum, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Suitable bases for preparing the salts according to the invention are, for example, alkali metal carbonates, such as potassium carbonate, alkali metal and alkaline earth metal hydroxides, for example NaOH or KOH, alkali metal and alkaline earth metal hydrides, for example NaH, alkali metal and alkali earth metal alkoxides, for example sodium methoxide, potassium tert-butoxide, or ammonia or ethanolamine.

The solvents referred to in the process variants above as "inert solvents" are in each case solvents which are inert under the reaction conditions in question but which do not have to be inert under any reaction conditions.

The compounds of the formula (I) according to the invention and their salts have an excellent herbicidal activity against a broad spectrum of economically important mono- and dicotyledonous harmful plants. The active substances also act efficiently on perennial weeds which produce shoots from rhizomes, root stocks or other perennial organs and are difficult to control. In this context, it is unimportant whether the substances are applied before sowing, preemergence or postemergence. Specifically, some representatives of the mono- and dicotyledonous weed flora which can be controlled by the compounds according to the invention may be mentioned by way of example, without a restriction to certain species being intended to take place as a result of the mention.

Amongst the monocotyledonous weed species, those on which the active substances act efficiently are, for example,

*Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagiftaria, Scirpus, Setaria, Sphenoclea* and *Cyperus* species from the annual group and, amongst the perennial species, *Agropyron, Cynodon, Imperata* and *Sorghum* and also perennial *Cyperus* species.

In the case of dicotyledonous weed species, the spectrum of action extends to species such as, for example,

*Galium, Viola, Veronica, Lamium, Stellaria, Amaranthus, Sinapis, Ipomoea, Matricaria, Abutilon* and *Sida* amongst the annuals and *Convolvulus, Cirsium, Rumex* and *Artemisia* in the case of the perennial weeds.

Herbicidal action is also achieved in the case of dicotyledonous harmful plants such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

Harmful plants occurring under the specific cultivation conditions of rice, such as, for example, *Sagittaria, Alisma, Eleocharis, Scirpus* and *Cyperus*, are also outstandingly well controlled by the active substances according to the invention.

If the compounds according to the invention are applied to the soil surface before germination, then the weed seedlings are either prevented completely from emerging or the weeds grow until they have reached the cotyledon stage, but then their growth stops and they finally die completely after three to four weeks have elapsed.

When the active substances are applied postemergence to the green parts of the plants, growth stops equally drastically a very short time after treatment and the weed plants remain at the stage of growth at the time of application, or they die completely after a certain time, so that in this manner competition by the weeds, which is harmful to the crop plants, is eliminated at a very early stage and in a sustained manner.

Although the compounds according to the invention have an excellent herbicidal activity against mono- and dicotyledonous weeds, crop plants of economically important crops such as, for example, wheat, barley, rye, rice, corn, sugar beet, sugar cane, cotton and soybeans, are damaged only to an insignificant extent or not at all. For these reasons, the present compounds are very highly suitable for the selective control of undesired plant growth in stands of agriculturally useful plants.

Owing to the broad activity against unwanted vegetation, the compounds of the formula (I) or their salts can also be used in tree stands, in viticulture and in nut-producing crops. Also possible is the use on industrial terrain to prevent plants from growing, on free industrial areas or, for example, on roads or railroad tracks.

In addition, the substances according to the invention have outstanding growth-regulatory properties in crop plants. They engage in the plants' metabolism in a regulatory fashion and can thus be employed for influencing plant constituents in a targeted fashion and for facilitating harvesting, such as, for example, by triggering desiccation and stunted growth. Moreover, they are also suitable for generally controlling and inhibiting undesired vegetative growth without simultaneously killing the plants. Inhibiting vegetative growth plays an important role in many monocotyledonous and dicotyledonous crops since lodging can be reduced, or prevented completely, hereby.

On account of their herbicidal and plant growth-regulatory properties, the active substances can also be employed for the control of harmful plants in crops of known genetically modified plants or genetically modified plants yet to be developed. As a rule, the transgenic plants are distinguished by particularly advantageous properties, for example by resistances to certain pesticides, especially certain herbicides, resistances to plant diseases or pathogens of plant diseases such as certain insects or microorganisms such as fungi, bacteria or viruses. Other particular properties relate, for example, to the harvested material with respect to quantity, quality, storability, composition and specific constituents. Thus, transgenic plants having an increased starch content or where the quality of the starch is altered or those having a different fatty acid composition of the harvested material are known.

The compounds of the formula (I) according to the invention or their salts are preferably used in economically important transgenic crops of useful and ornamental plants, e.g. of cereals such as wheat, barley, rye, oats, *sorghum* and millet, rice, cassava and corn or alternatively crops of sugar beet, cotton, soybeans, oilseed rape, potatoes, tomatoes, peas and other types of vegetables.

The compounds of the formula (I) can preferably be employed as herbicides in useful plant crops which are resistant, or have been made resistant by recombinant methods, to the phytotoxic effects of the herbicides.

Traditional ways of generating novel plants which have modified characteristics in comparison with existing plants consist, for example, in traditional breeding methods and the generation of mutants. Alternatively, novel plants with modified characteristics can be generated using recombinant procedures (see, for example, EP-A-0221044, EP-A-0131624). For example, a number of cases have been described of
  recombinant modifications of crop plants for the purpose of modifying the starch synthesized in the plants (e.g. WO 92/11376, WO 92/14827, WO 91/19806),
  transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659),
  transgenic crop plants, for example cotton, with the capability of producing *Bacillus thuringiensis* toxins (Bt toxins) which make the plants resistant to certain pests (EP-A-0142924, EP-A-0193259),
  transgenic crop plants having a modified fatty acid composition (WO 91/13972).

Numerous molecular biology techniques using which novel transgenic plants having modified properties can be produced are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], V C H Weinheim, 2nd Edition, 1996 or Christou, "Trends in Plant Science" 1 (1996) 423-431).

For recombinant manipulations of this type, nucleic acid molecules can be introduced into plasmids which allow mutagenesis or a sequence modification by means of recombination of DNA sequences. With the aid of the abovementioned standard procedures, it is possible, for example, to perform base exchanges, to remove subsequences or to add natural or synthetic sequences. For the connection of the DNA fragments to one another, adaptors or linkers can be attached to the fragments. For example, plant cells having a reduced activity of a gene product can be produced by the expression of at least one corresponding antisense RNA, a sense RNA to achieve a cosuppression effect or the expression of at least one appropriately constructed ribozyme which specifically cleaves transcripts of the abovementioned gene product.

For this, it is possible to use, on the one hand, DNA molecules which comprise the entire coding sequence of a gene product including flanking sequences which may be present, and also DNA molecules which only comprise parts of the coding sequence, where these parts must be long enough in order to bring about an antisense effect in the cells. The use of DNA sequences which have a high degree of homology to the coding sequences of a gene product, but are not completely identical, is also possible.

When nucleic acid molecules are expressed in plants, the synthesized protein can be localized in any desired compartment of the plant cell. However, in order to achieve localization in a certain compartment, it is possible, for example, to link the coding region with DNA sequences which ensure localization in a certain compartment. Sequences of this type are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to give intact plants according to known techniques. In principle, the transgenic plants can be plants of any desired plant species, i.e. both monocotyledonous and dicotyledonous plants.

Transgenic plants are thus obtainable which have modified properties as a result of overexpression, suppression or inhibition of homologous (=natural) genes or gene sequences or expression of heterologous (=foreign) genes or gene sequences.

The compounds (I) according to the invention can preferably be employed in transgenic crops which are resistant to herbicides from the group consisting of the sulfonylureas, imidazolinones, glufosinate-ammonium or glyphosate-isopropylammonium and analogous active substances.

When the active substances according to the invention are used in transgenic crops, in addition to the effects against harmful plants to be observed in other crops, effects often occur which are specific for application in the particular transgenic crop, for example a modified or specifically widened spectrum of weeds which can be controlled, altered application rates which can be employed for application, preferably good combining ability with the herbicides to which the transgenic crop is resistant, and an effect on growth and yield of the transgenic crop plants.

The invention therefore also relates to the use of the compounds (I) according to the invention as herbicides for controlling harmful plants in transgenic crop plants.

The compounds according to the invention can be used in the customary preparations in the form of wettable powders, emulsifiable concentrates, sprayable solutions, dusting agents or granules. The invention therefore also relates to herbicidal and plant growth-regulating compositions which contain compounds of the formula (I).

The compounds of the formula (i) can be formulated in various ways, depending on what biological and/or chemico-physical parameters are prespecified. Examples of suitable formulation possibilities are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions on an oil or water basis, oil-miscible solutions, capsule suspensions (CS), dusting agents (DP), dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hauser Verlag Munich, 4th Edition 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries which are necessary, such as inert materials, surfactants, solvents and other additives, are also known and are described, for example, in: Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Edition 1986.

On the basis of these formulations, combinations with other pesticidally active substances such as, for example, insecticides, acaricides, herbicides, fungicides, and also with safeners, fertilizers and/or growth regulators can also be prepared, e.g. in the form of a finished formulation or as a tank mix.

Wettable powders are preparations which are uniformly dispersible in water and which, besides the active compound, also contain surfactants of ionic and/or nonionic type (wetting agents, dispersants), e.g. polyethoxylated alkylphenols, polyethoxylated fatty alcohols, polyoxethylated fatty amines, fatty alcohol polyglycol ether sulfates, alkanesulfonates, alkylbenzenesulfonates, sodium lignosulfonates, sodium 2,2'-dinaphthylmethane-6,6'-disulfonate, sodium dibutylnaphthalene-sulfonate or alternatively sodium oleoylmethyltaurate in addition to a diluent or inert substance. For preparation of the wettable powders, the herbicidal active substances are finely ground, for example, in customary equipment such as hammer mills, blowing mills and air-jet mills and simultaneously or subsequently mixed with the formulation auxiliaries.

Emulsifiable concentrates are prepared by dissolving the active substance in an organic solvent, e.g. butanol, cyclohexanone, dimethylformamide, xylene or alternatively relatively high-boiling aromatics or hydrocarbons or mixtures of the organic solvents with addition of one or more surfactants of ionic and/or nonionic type (emulsifiers). Examples of emulsifiers which can be used are: alkylarylsulfonic acid calcium salts such as calcium dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters such as, for example, sorbitan fatty acid esters or polyoxyethylene sorbitan esters such as, for example, polyoxyethylene sorbitan fatty acid esters. Dusting agents are obtained by grinding the active substance with finely divided solid substances, e.g. talc, natural clays, such as kaolin, bentonite and pyrophyllite, or diatomaceous earth.

Suspension concentrates can be water- or oil-based. They can be prepared, for example, by wet grinding by means of commercially available bead mills and, if appropriate, addition of surfactants, such as have already been mentioned, for example, above in the case of the other formulation types.

Emulsions, e.g. oil-in-water emulsions (EW), can be prepared, for example, by means of stirrers, colloid mills and/or static mixers using aqueous organic solvents and, if appropriate, surfactants, such as have already been mentioned, for example, above in the case of the other formulation types.

Granules can either be prepared by spraying the active substance onto adsorptive, granulated inert material or by applying active substance concentrates to the surface of carriers such as sand, kaolinites or of granulated inert material by means of binders, e.g. polyvinyl alcohol, sodium polyacrylate or alternatively mineral oils. Suitable active substances can also be granulated in the manner customary for the preparation of fertilizer granules—if desired as a mixture with fertilizers.

As a rule, water-dispersible granules are prepared by the customary processes such as spray-drying, fluidized bed granulation, disk granulation, mixing using high-speed mixers and extrusion without solid inert material. For the preparation of disk, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details on the formulation of plant protection materials see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations contain 0.1 to 99% by weight, in particular 0.1 to 95% by weight, of active substance of the formula (I).

In wettable powders, the active substance concentration is, for example, approximately 10 to 90% by weight, the remainder to 100% by weight consists of customary formulation constituents. In the case of emulsifiable concentrates, the active substance concentration can be approximately 1 to 90, preferably 5 to 80, % by weight. Formulations in the form of dusts contain 1 to 30% by weight of active substance, preferably usually 5 to 20% by weight of active substance, sprayable solutions contain approximately 0.05 to 80, preferably 2 to 50, % by weight of active substance. In the case of water-dispersible granules, the active substance content depends partly on whether the active compound is liquid or solid and which granulation auxiliaries, fillers etc. are used. In the case of water-dispersible granules, the content of active substance is, for example, between 1 and 95% by weight, preferably between 10 and 80% by weight.

In addition, the active substance formulations mentioned optionally contain the binders, wetting agents, dispersants, emulsifiers, penetrants, preservatives, antifreeze agents, solvents, fillers, carriers, colorants, antifoams, evaporation inhibitors and the pH and viscosity regulators which are customary in each case. The compounds of the formula (I) or their salts can be employed as such or in the form of their preparations (formulations) as combinations with other pesticidally active substances, such as, for example, insecticides, acaricides, nematicides, herbicides, fungicides, safeners, fertilizers and/or growth regulators, for example as a premix or as tank mixes.

Co-components which may be employed for the active substances according to the invention in mixed formulations or in tank mix are, for example, known active compounds which are described, for example, in Weed Research 26, 441-445 (1986), or "The Pesticide Manual", 12th Edition, The British Crop Protection Council and the Royal Soc. of Chemistry, 2000/2001 and literature cited therein. Known herbicides or plant growth regulators which can be combined with the compounds of the formula (I), are, for example, the following active substances; below, the compounds are either designated by the common name according to the International Organization for Standardization (ISO) or using the chemical name, if appropriate together with a customary code number:

acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amidochlor, amidosulfuron; amitrol; AMS, i.e. ammonium sulfamate; anilofos; asulam; atrazin; azafenidin, azimsulfurone (DPX-A8947); aziprotryn; barban; BAS 516H, i.e. 5-fluoro-2-phenyl-4H-3,1-benzoxazin-4-one; beflubutamid, benazolin(-ethyl); benfluralin; benfuresate; bensulfuron(-methyl); bensulide; bentazone; benzobicyclon, benzofenap; benzofluor; benzoylprop(-ethyl); benzthiazuron; bialaphos; bifenox; bispyribac(-sodium), bromacil; bromobutide; bromofenoxim; bromoxynil; bromuron; buminafos; busoxinone;

butachlor; butafenacil, butamifos; butenachlor; buthidazole; butralin; butroxydim, butylate; cafenstrole (CH-900); carbetamide; carfentrazone(-ethyl) (ICI-A0051); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinmethylin; cinosulfuron; clethodim; cinidon(-methyl), clefoxydim, clodinafop and its ester derivatives (for example clodinafop-propargyl); clomazone; clomeprop; cloproxydim; clopyralid; clopyrasulfuron(-methyl), cloransulam(-methyl); cumyluron (JC 940); cyanazine; cycloate; cyclosulfamuron (AC 104); cycloxydim; cycluron; cyhalofop and its ester derivatives (for example the butyl ester, DEH-112); cyperquat; cyprazine; cyprazole; daimuron; 2,4-D, 2,4-DB; 2,4-DB, dalapon; desmedipham; desmetryn; di-allate; dicamba; dichlobenil; dichlorprop; diclofop and its esters such as diclofop-methyl; diclosulam, diethatyl(-ethyl); difenoxuron; difenzoquat; diflufenican; diflufenzopyr, dimefuron; dimepiperate, dimethachlor; dimethametryn; dimethenamid (SAN-582H); dimethazone, dimexyflam, dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl]ethanesulfonamide; ethoxyfen and its esters (for example the ethyl ester, HN-252); fenoprop; fenoxan, fenoxaprop and fenoxaprop-P and their esters, for example fenoxaprop-P-ethyl and fenoxaprop-ethyl; fenoxydim, fentrazamide, fenuron; flamprop(-methyl or -isopropyl or -isopropyl-L); flazasulfuron; floazulate, florasulam, fluazifop and fluazifop-P and their esters, for example fluazifop-butyl and fluazifop-P-butyl; flucarbazone (-sodium), fluchloralin; flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupyrsulfuron(-methyl or -sodium), flurenol(-butyl), fluridone; flurochloridone; fluroxypyr(-meptyl); flurprimidol, flurtamone; fluthiacet(-methyl), fluthiamide, fomesafen, foramsulfuron, fosamine; furyloxyfen; glufosinate(-ammonium); glyphosate (-isopropylammonium); halosafen; halosulfuron(-methyl) and its esters (for example the methyl ester, NC-319); haloxyfop and its esters; haloxyfop-P (=R-haloxyfop) and its esters; hexazinone; imazamethabenz(-methyl); imazapyr; imazaquin and salts such as the ammonium salt; imazamethapyr, imazamox, imazapic, imazethamethapyr; imazethapyr; imazosulfuron; indanofan, iodosulfuron-methyl-sodium salts, ioxynil; isocarbamid; isopropalin; isoproturon; isouron; isoxaben; isoxachlortole, isoxaflutole, isoxapyrifop; karbutilate; lactofen; lenacil; linuron; MCPA; MCPB; mecoprop; mefenacet; mefluidid; mesosulfuron-methyl, mesotrione, metamitron; metazachlor; methabenzthiazuron; metham; methazole; methoxyphenone; methyldymron; metabenzuron, methobenzuron; metobromuron; (alpha-)metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methyl-ethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron, oxaziclomefone, oxyfluorfen; paraquat; pebulate; pelargonic acid, pendimethalin; pentoxazone, perfluidone; phenisopham; phenmedipham; picloram; picolinafen, piperophos; piributicarb; pirifenop-butyl; pretilachlor; primisulfuron(-methyl); procarbazone-(sodium), procyazine; prodiamine; profluralin; proglinazine(-ethyl); prometon; prometryn; propachlor; propanil; propaquizafop and its esters; propazine; propham; propisochlor; propyzamide; prosulfalin; prosulfocarb; prosulfuron (CGA-152005); prynachlor; pyraflufen(-ethyl), pyrazolinate; pyrazon; pyrazosulfuron(-ethyl); pyrazoxyfen; pyribenzoxim, pyributicarb, pyridafol, pyridate; pyrimidobac(-methyl), pyrithiobac (-sodium) (KIH-2031); pyroxofop and its esters (for example the propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyi]oxy]propanoic acid and its methyl ester; sulcotrione, sulfentrazon (FMC-97285, F-6285); sulfazuron; sulfometuron(-methyl); sulfosate (ICI-A0224); sulfosulfuron, TCA; tebutam (GCP-5544); tebuthiuron; tepraloxydim, terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenyichlor (NSK-850); thiafluamide, thiazafluron; thiazopyr (Mon-13200); thidiazimin (SN-24085); thifensulfuron(-methyl); thiobencarb; tiocarbazil; tralkoxydim; tri-allate; triasulfuron; triaziflam, triazofenamide; tribenuron(-methyl); triclopyr; tridiphane; trietazine; trifluralin; triflusulfuron and its esters (for example the methyl ester, DPX-66037); trimeturon; tritosulfuron, tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

Controlling harmful plants selectively is of particular interest in crops of useful plants and ornamentals. Even though the compounds (I) according to the invention already exhibit very good to sufficient selectivity in many crops, it is possible, in principle, that symptoms of phytotoxicity occur on the cultivated plants in some crops and especially also in the case of mixtures with other herbicides which are less selective. In this respect, combinations of compounds (I) according to the invention which are of particular interest are those which contain the compounds (I) or their combinations with other herbicides or pesticides and safeners. The safeners, which are employed in such an amount that they act as antidote, reduce the phytotoxic side effects of the herbicides/pesticides employed, for example in economically important crops such as cereals (wheat, barley, rye, corn, rice, *sorghum* and millet), sugar beet, sugar cane, oilseed rape, cotton and soybeans, preferably cereals.

The following groups of compounds are examples of suitable safeners for the compounds (I) and their combinations with further pesticides:

a) compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (S1-1) ("mefenpyr-diethyl", "The Pesticide Manual", 12th edition, 2000, No. 492, pp. 594-595) and related compounds as are described in WO 91/07874;
b) dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds as are described in EP-A-333 131 and EP-A-269 806;
c) compounds of the triazolecarboxylic acids type, preferably compounds such as fenchlorazole (and its ethyl ester), i.e. ethyl 1-(2,4-dichlorophenyl)-5-trichloromethyl-(1H)-1,2,4-triazole-3-carboxylate (S1-6), and related compounds (see EP-A-174 562 and EP-A-346 620);
d) compounds of the 5-benzyl- or 5-phenyl-2-isoxazoline-3-carboxylic acid type or the 5,5-diphenyl-2-isoxazoline-3-carboxylic acid type, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds as they are described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as are described in the German Patent Application (WO-A-95/07897);
e) compounds of the 8-quinolinoxyacetic acid type (S2), preferably 1-methylhex-1-yl (5-chloro-8-quinolinoxy)acetate (common name "cloquintocet-mexyl") (S2-1) (see "The Pesticide Manual", 12th Edition, 2000, No. 195, pp. 263-264)
1,3-dimethylbut-1-yl (5-chloro-8-quinolinoxy)acetate (S2-2),
4-allyloxybutyl (5-chloro-8-quinolinoxy)acetate (S2-3),
1-allyloxyprop-2-yl (5-chloro-8-quinolinoxy)acetate (S2-4), ethyl (5-chloro-8-quinolinoxy)acetate (S2-5),
methyl (5-chloro-8-quinolinoxy)acetate (S2-6),
allyl (5-chloro-8-quinolinoxy)acetate (S2-7),
2-(2-propylideneiminooxy)-1-ethyl (5-chloro-8-quinolinoxy)acetate (S2-8),
2-oxoprop-1-yl (5-chloro-8-quinolinoxy)acetate (S2-9),
and related compounds as are described in EP-A-86 750, EP-A-94 349 and EP-A-191 736 or EP-A-0 492 366;
f) compounds of the (5-chloro-8-quinolinoxy)malonic acid type, preferably compounds such as diethyl (5-chloro-8-quinolinoxy)malonate, diallyl (5-chloro-8-quinolinoxy)malonate, methylethyl (5-chloro-8-quinolinoxy)malonate and related compounds as are described in EP-A-0 582 198;
g) active substances of the phenoxyacetic or phenoxypropionic acid derivatives type or of the aromatic carboxylic acids type, such as, for example, 2,4-dichlorophenoxyacetic acid (and its esters) (2,4-D), 4-chloro-2-methylphenoxypropionic ester (mecoprop), MCPA or 3,6-dichloro-2-methoxybenzoic acid (and its esters) (dicamba);
h) active substances of the pyrimidines type which are employed in rice as soil-acting safeners, such as, for example, "fenclorim" ("The Pesticide Manual", 12th edition, 2000, No. 325, pp. 386-387) (=4,6-dichloro-2-phenylpyrimidine), which is also known as safener for pretilachlor in seeded rice;
i) active substances of the dichloroacetamides type, which are frequently employed as pre-emergence safeners (soil-acting safeners), such as, for example,
"dichlormid" ("The Pesticide Manual", 12th edition, 2000, No. 225, pp. 270-271) (=N,N-diallyl-2,2-dichloroacetamide),
"R-29148" (=3-dichloroacetyl-2,2,5-trimethyl-1,3-oxazolidine, by Stauffer),
"benoxacor" ("The Pesticide Manual", 12th edition, 2000, No. 65, pp. 74-75) (=4-dichloroacetyl-3,4-dihydro-3-methyl-2H-1,4-benzoxazine),
"PPG-1292" (=N-allyl-N-[(1,3-dioxolan-2-yl)methyl] dichloroacetamide by PPG Industries),
"DK-24" (=N-allyl-N-[(allylaminocarbonyl)methyl] dichloroacetamide by Sagro-Chem),
"AD-67" or "MON 4660" (=3-dichloroacetyl-1-oxa-3-azaspiro[4,5]decane by Nitrokemia and Monsanto, respectively),
"diclonon" or "BAS145138" or "LAB145138" (=3-dichloroacetyl-2,5,5-trimethyl-1,3-diazabicyclo[4.3.0] nonane by BASF) and
"furilazol" or "MON 13900" (see "The Pesticide Manual", 12th edition, 2000, No. 401, pp. 482-483) (=(RS)-3-dichloroacetyl-5-(2-furyl)-2,2-dimethyloxazolidine);
j) active substances of the dichloroacetone derivatives type, such as, for example,
"MG 191" (CAS Reg. No. 96420-72-3) (=2-dichloromethyl-2-methyl-1,3-dioxolane by Nitrokemia), which is known as safener for corn;
k) active substances of the oxyimino compounds type, which are known as seed treatment products, such as, for example,
"oxabetrinil" ("The Pesticide Manual", 12th edition, 2000, No. 577, p. 689) (=(Z)-1,3-dioxolan-2-ylmethoxyimino (phenyl)acetonitrile), which is known as seed-treatment safener for *sorghum* and millet against metolachlor damage,
"fluxofenim" ("The Pesticide Manual", 12th edition, 2000, No. 389, pp.467-468) (=1-(4-chlorophenyl)-2,2,2-trifluoro-1-ethanone O-(1,3-dioxolan-2-ylmethyl)oxime, which is known as seed-dressing safener for *sorghum* and millet against metolachlor damage, and
"cyometrinil" or "-CGA-43089" ("The Pesticide Manual", 12th edition, 2000, No. 974, p. 983) (=(Z)-cyanomethoxyimino(phenyl)acetonitrile), which is known as seed-treatment safener for *sorghum* and millet against metolachlor damage;
l) active substances of the thiazolecarboxylic ester type, which are known as seed treatment products, such as, for example,
"flurazol" ("The Pesticide Manual", 12th edition, 2000, No. 376, pp. 450-451) (=benzyl 2-chloro-4-trifluoromethyl-1,3-thiazole-5-carboxylate), which is known as seed-treatment safener for *sorghum* and millet against alachlor and metolachlor damage;
m) active substances of the naphthalenedicarboxylic acid derivatives type, which are known as seed treatment products, such as, for example,
"naphthalic anhydride" ("The Pesticide Manual", 12th edition, 2000, No. 1249, pp. 1009-1010) (=1,8-naphthalenedicarboxylic anhydride), which is known as seed-treatment safener for corn against thiocarbamate herbicide damage;
n) active substances of the chromanacetic acid derivatives type, such as, for example,
"CL 304415" (CAS Reg. No. 31541-57-8) (=2-(4-carboxychroman-4-yl)acetic acid by American Cyanamid), which is known as safener for corn against damage by imidazolinones;

o) active substances which, in addition to a herbicidal action against harmful plants, also exhibit a safener action in connection with crop plants such as rice, such as, for example, "dimepiperate" or "MY-93" ("The Pesticide Manual", 12th edition, 2000, No. 251, pp. 302-303) (=S-1-methyl-1-phenylethyl piperidine-1-carbothioate), which is known as safener for rice against damage by the herbicide molinate, "daimuron" or "SK 23" ("The Pesticide Manual", 12th edition, 2000, No. 207, p. 247) (=1-(1-methyl-1-phenyl-ethyl)-3-p-tolylurea), which is known as safener for rice against damage by the herbicide imazosulfuron, "cumyluron"="JC-940" (=3-(2-chlorophenylmethyl)-1-(1-methyl-1-phenyl-ethyl)urea, see JP-A-60087254), which is known as safener for rice against damage by several herbicides, "methoxyphenone" or "NK 049" (=3,3'-dimethyl-4-methoxybenzophenone), which is known as safener for rice against damage by several herbicides, "CSB" (=1-bromo-4-(chloromethylsulfonyl)benzene) (CAS Reg. No. 54091-06-4, by Kumiai), which is known as safener in rice against damage by several herbicides;

p) N-acylsulfonamides of the formula (S3) and their salts

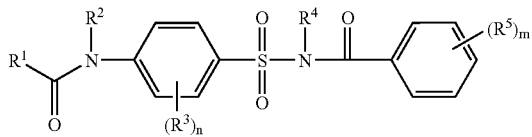

(S3)

as are described in WO-A-97/45016;

q) acylsulfamoylbenzamides of the formula (S4), if appropriate also in salt form,

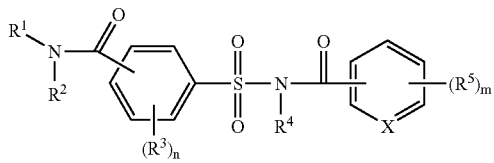

(S4)

as are described in International Application No. PCT/EP98/06097; and r) compounds of the formula (S5),

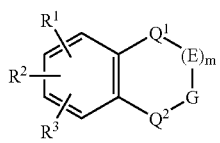

(S5)

as are described in WO-A 98/13361, including the stereoisomers and the salts conventionally used in agriculture.

Amongst the safeners mentioned, those which are of particular interest are (S1-1) and (S1-9) and (S2-1), in particular (S1-1) and (S1-9).

Some of the safeners are already known as herbicides and therefore simultaneously also display a protective action in connection with the crop plants in addition to the herbicidal action in connection with harmful plants.

The weight ratio of herbicide (mixture) to safener generally depends on the application rate of herbicide and the efficacy of the safener in question; it can vary within wide limits, for example in the range of from 200:1 to 1:200, preferably from 100:1 to 1:100, in particular 20:1 to 1:20. The safeners can be formulated with further herbicides/pesticides, analogously to the compounds (I) or their mixtures, and provided and used as readymix or tank mix together with the herbicides.

For use, the herbicide or herbicide safener formulations, which are present in a customary commercial form, are, if appropriate, diluted in the customary fashion, for example using water in the case of wettable powders, emulsifiable concentrates, dispersions and water-dispersible granules. Preparations in the form of dusts, soil granules, granules for spreading, and sprayable solutions, are usually not diluted further with other inert materials prior to use.

The application rate required of the compounds of the formula (I) varies with, inter alia, the external conditions such as temperature, humidity and the type of the herbicide used. It can vary within wide limits, for example between 0.001 and 10.0 kg/ha or more of active substance, but it is preferably between 0.005 and 5 kg/ha, in particular between 0.01 and 1 kg/ha of active substance.

A. CHEMICAL EXAMPLES

Example 1

2-Amino-4-(5,7-dimethyl-1,2,3,4-tetrahydronaphthalene-1-amino)-1,3,5-triazine a) 27.0 g (0.13 mol) of 1-amino-5,7-dimethyl-1,2,3,4-tetrahydronaphthalene hydrochloride and 11.5 g (0.13 mol) of cyanoguanidine are homogenized and taken up in 60 ml of 1,2-dichlorobenzene. This mixture is heated at 140-160° C. for 150 minutes which initially gives a homogeneous mixture; however, this mixture separates again over time. After cooling and addition of 100 ml of toluene, it is possible to obtain, by filtration with suction, 40.0 g (94% of theory of a purity greater than 90%) of 1-biguanidino-5,7-dimethyl-1,2,3,4-tetrahydronaphthalene hydrochloride of melting point 215-216° C.

b) 3.70 g (0.013 mol) of 1-biguanidino-5,7-dimethyl-1,2,3,4-tetrahydronaphthalene hydrochloride are added to a sodium methoxide solution of 1.01 g (0.044 mol) of sodium in 50 ml of methanol. 3.7 g (0.03 mol) of ethyl formate are then added, and the mixture is stirred at 25° C. for 15 hours. Water and methylene chloride are added to the reaction mixture, the organic phase is separated off and the aqueous phase is extracted two more times with methylene chloride. In each case, the organic phase is separated off, and the combined organic phases are dried with sodium sulfate. The drying agent is filtered off and the methylene chloride phase is concentrated. Separation by silica gel column chromatography using the mobile phase ethyl acetate gives 2.3 g (62% of theory of a purity of 90%) of N2-(5,7-dimethyl-1,2,3,4-tetrahydro-1-naphthalenyl)-1,3,5-triazine-2,4-diamine of melting point 178-180° C.

The compounds described in Tables 1 and 2 are obtained analogously to Example 1 above.

In the table:

| | |
|---|---|
| No. = | example or example number |
| m.p. = | melting point in ° C. |
| State = | state of aggregation or other information (consistency etc.), |
| Me = | methyl |
| Et = | ethyl |
| Pr = | propyl |
| i-Pr = | isopropyl |
| X-i-Pr = | sub.-isopropyl e.g. F-i-Pr = fluoroisopropyl, i.e. —CF(CH$_3$)$_2$ of the formula |

| | |
|---|---|
| c-Pr = | cyclopropyl |
| 1-Me-c-Pr = | 1-methyl-cyclopropyl = |

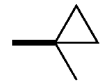

| | |
|---|---|
| t-Bu = | tert-butyl |
| Ph = | phenyl |
| Bz = | benzyl |
| Ac = | acetyl |
| numbers = | First number at a substituent on the bicycle indicates the position of the substituent radical X$^n$ having the same number n |
| Morpholino = | -morpholine = |

| | |
|---|---|
| Piperidino = | -piperidine = |

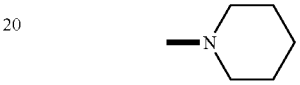

Note:
The bold line indicates in each case the point of attachment of the radicals.

TABLE 1

Compounds of the formula (I-A)

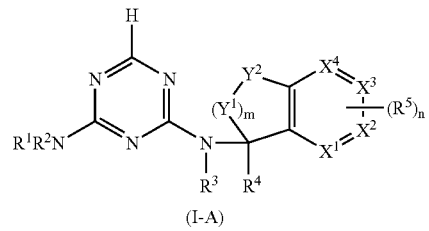

(I-A)

| No. | NR$^1$R$^2$ | R$^3$ | R$^4$ | —X$^1$=X$^2$—X$^3$=X$^4$— | (R$^5$)$_n$ | (Y$^1$)$_m$ | Y$^2$ | State/m.p. (° C.) |
|---|---|---|---|---|---|---|---|---|
| 1 | NH$_2$ | H | H | —C=C—C=C— | 2-Me, 4-Me | —CH$_2$—CH$_2$— | —CH$_2$— | 178–180 |
| 2 | NH$_2$ | H | H | —C=C—C=C— | 2-Me, 4-Me | —CMeH—CH$_2$— | —CH$_2$— | |
| 3 | NH$_2$ | H | H | —C=C—S— | 2-Me | —CH$_2$—CH$_2$— | —CH$_2$— | |
| 4 | NH$_2$ | H | H | —C=C—C=C— | 2-Me, 4-Me | —CH$_2$—CH$_2$— | —O— | 119-121 |
| 5 | NH$_2$ | H | H | —C=C—C=C— | 4-Me | —CH$_2$—CH$_2$— | —O— | 106-108 |
| 6 | NH$_2$ | H | H | —C=C—C=C— | 1-Me, 4-Me | —CH$_2$—CH$_2$— | —O— | |
| 7 | NH$_2$ | H | H | —C=C—C=C— | 2-Me, 4-Me | —CH$_2$—CH$_2$— | —NMe— | |
| 8 | NH$_2$ | H | H | —C=C—C=C— | 4-Me | —CH$_2$—CH$_2$— | —NMe— | |
| 9 | NHC(=O)—CH$_2$—CH$_2$—Cl | H | H | —C=C—C=C— | 2-Me, 4-Me | —CH$_2$—CH$_2$— | —NMe— | |
| 10 | NHC(=O)—CH$_2$—CH$_2$—Cl | H | H | —C=C—C=C— | 2-Me, 4-Me | —CH$_2$—CH$_2$— | —C(=O)— | |
| 11 | NH$_2$ | H | H | —C=C—C=C— | 2-Me, 4-Me | —CH$_2$—CH$_2$— | C(=O) | |
| 12 | NHC(=O)—CH$_2$—OCH$_3$ | H | H | —C=C—C=C— | 2-Me, 4-Me | —CH$_2$—CH$_2$— | C(=O) | |
| 13 | NHC(=O)—CH$_2$—OCH$_3$ | H | H | —C=C—C=C— | 2-Me, 4-Me | —CH$_2$—CH$_2$— | CHOH | |
| 14 | NH$_2$ | H | H | —C=C—C=C— | 2-Me, 4-Me | —CH$_2$—CH$_2$— | CHOH | |
| 15 | NHC(=O)—CH$_3$ | H | H | —C=C—C=C— | 2-Me, 4-Me | —CH$_2$—CH$_2$— | CHOH | |
| 16 | NH$_2$ | H | H | —C=C—C=C— | 1-Me, 2-Me, 4-Me | —CH$_2$—CH$_2$— | —CH$_2$— | |
| 17 | NHC(=O)—CH$_3$ | H | H | —C=C—C=C— | 1-Me, 2-Me, 4-Me | —CH$_2$—CH$_2$— | —CH$_2$— | |
| 18 | NH$_2$ | H | H | —C=C—C=C— | 1-Me, 3-Me, 4-Me | —CH$_2$—CH$_2$— | —CH$_2$— | |
| 19 | NH$_2$ | H | H | —C=C—C=C— | 3-Me, 4-Me | —CH$_2$—CH$_2$— | —CH$_2$— | 208-211 |
| 20 | NH$_2$ | H | H | —C=C—C=C— | 3-F, 4-Me | —CH$_2$—CH$_2$— | —CH$_2$— | |
| 21 | NH$_2$ | H | H | —C=C—C=C— | 3-Cl, 4-Me | —CH$_2$—CH$_2$— | —CH$_2$— | |
| 22 | NH$_2$ | H | H | —C=C—C=C— | 2-Et | —CH$_2$—CH$_2$— | —CH$_2$— | |

TABLE 1-continued

Compounds of the formula (I-A)

| No. | NR$^1$R$^2$ | R$^3$ | R$^4$ | —X$^1$=X$^2$—X$^3$=X$^4$— | (R$^5$)$_n$ | (Y$^1$)$_m$ | Y$^2$ | State/m.p. (° C.) |
|---|---|---|---|---|---|---|---|---|
| 23 | NH$_2$ | H | H | —C=C—C=C— | 2-Et, 4-Me | —CH$_2$—CH$_2$— | —CH$_2$— | |
| 24 | NH$_2$ | H | H | —C=C—C=C— | 2-(1'-fluoro)-Et, 4-Me | —CH$_2$—CH$_2$— | —CH$_2$— | |
| 25 | NHMe | H | H | —C=C—C=C— | 2-Me, 4-Me | —CH$_2$—CH$_2$— | —CH$_2$— | |
| 26 | NMe$_2$ | H | H | —C=C—C=C— | 2-Me, 4-Me | —CH$_2$—CH$_2$— | —CH$_2$— | |
| 27 | NMe(CO)Me | H | H | —C=C—C=C— | 2-Me, 4-Me | —CH$_2$—CH$_2$— | —CH$_2$— | |
| 28 | NH$_2$ | H | H | —C=C—C=C— | 2-F, 4-Me | —CMeH—CH$_2$— | —CH$_2$— | |
| 29 | NMeH | H | H | —C=C—C=C— | 2-Me, 4-Me | —CMeH—CH$_2$— | —CH$_2$— | |
| 30 | NH$_2$ | H | H | —C=C—C=C— | 2-Me, 4-Me | —CH$_2$—CH$_2$— | — | solid foam |
| 31 | NH$_2$ | H | H | —C=C—C=C— | 3-Me, 4-Me | —CH$_2$—CH$_2$— | — | |
| 32 | NH$_2$ | H | H | —C=C—C=C— | 2-Me, 3-Me | —CH$_2$—CH$_2$— | — | solid foam |
| 33 | NH$_2$ | H | H | —C=C—C=C— | 2-Me, 3-Me, 4-Me | —CH$_2$—CH$_2$— | — | solid foam |
| 34 | NH$_2$ | H | H | —C=C—C=C— | 1-Me, 4-Me | —CH$_2$—CH$_2$— | — | |
| 35 | NH$_2$ | H | H | —C=C—C=C— | 3-Me, 4-Me | —CH$_2$— | —O— | |
| 36 | NH$_2$ | H | H | —C=C—C=C— | 1-Me, 4-Me | —CH$_2$— | —O— | |
| 37 | NH$_2$ | H | H | —C=C—C=C— | 2-Me, 4-Me | —CH$_2$— | —O— | |
| 38 | NH$_2$ | H | H | —C=C—C=C— | 2-Me | —CH$_2$— | —O— | 184-190 |
| 39 | NH$_2$ | H | H | —C=C—C=C— | 2-Me | —CH$_2$— | —NMe— | |
| 40 | NH$_2$ | H | H | —C=C—C=C— | 2-Me, 4-Me | —CH$_2$— | —NMe— | |
| 41 | NH$_2$ | H | H | —C=C—C=C— | 1-Me, 2-Me | —CH$_2$— | —NMe— | |
| 42 | NH$_2$ | H | H | —C=C—C=C— | 2-Me, 3-OMe 4-Me | —CH$_2$—CH$_2$— | —NMe— | |
| 43 | NH$_2$ | H | H | —C=C—C=C— | 1-Me, 2-Me | —CH$_2$— | —CHMe— | |
| 44 | NH$_2$ | H | H | —C=C—C=C— | 2-Me | —CH$_2$— | —CHMe— | |
| 45 | NH$_2$ | H | H | —C=C—C=C— | 3-Me | —CH$_2$— | —CHMe— | |
| 46 | NH$_2$ | H | H | —C=C—C=C— | 3-Me, 4-Me | —CH$_2$— | —CHMe— | |
| 47 | NH$_2$ | H | H | —C=C—C=C— | 1-Me, 3-Me | —CH$_2$— | —CHMe— | |
| 48 | NH$_2$ | H | H | —C=C—C=C— | 2-Me | —CHMe— | —CHMe— | |
| 49 | NH$_2$ | H | H | —C=C—C=C— | 2-Me, 4-Me | —CHMe— | —CHMe— | |
| 50 | NH$_2$ | H | H | —C=C—C=C— | 1-Me, 4-Me | —CHMe— | —CHMe— | |
| 51 | NH$_2$ | H | H | —C=C—C=C— | 1-Et | —CHMe— | —CHMe— | |
| 52 | NH$_2$ | H | H | —C=C—C=C— | 2-Et | —CHMe— | —CHMe— | |
| 53 | NH$_2$ | H | H | —C=C—C=C— | 2-(1'-fluoro)-Et | —CHMe— | —CH$_2$— | |
| 54 | NH$_2$ | H | H | —C=C—C=C— | 3-(1'-fluoro)-Et | —CHMe— | —CH$_2$— | |
| 55 | NH$_2$ | H | H | —C=C—C=C— | 3-F | —CHMe— | —CH$_2$— | |
| 56 | NH$_2$ | H | H | —C=C—C=C— | 1-F | —CHMe— | —CH$_2$— | |
| 57 | NH$_2$ | H | H | —C=C—C=C— | 1-Cl | —CHMe— | —CH$_2$— | |
| 58 | NH$_2$ | H | H | —C=C—C=C— | 3-Cl | —CHMe— | —CH$_2$— | 177-179 |
| 59 | NMe$_2$ | H | H | —C=C—C=C— | 3-F | —CHMe— | —CH$_2$— | |
| 60 | NHC(=O)Me | H | H | —C=C—C=C— | 3-F | —CHMe— | —CH$_2$— | |
| 61 | NMeC(=O)Me | H | H | —C=C—C=C— | 3-F | —CHMe— | —CH$_2$— | |
| 62 | NHC(O)CH$_2$—OMe | H | H | —C=C—C=C— | 3-F | —CHMe— | —CH$_2$— | |
| 63 | NHC(=O)CF$_3$ | H | H | —C=C—C=C— | 3-F | —CHMe— | —CH$_2$— | |
| 64 | NHC(=O)CH$_2$—CH$_2$—Cl | H | H | —C=C—C=C— | 3-F | —CHMe— | —CH$_2$— | |
| 65 | NHC(=O)CH=CH$_2$ | H | H | —C=C—C=C— | 3-F | —CHMe— | —CH$_2$— | |
| 66 | NHC(=O)Ph | H | H | —C=C—C=C— | 3-F | —CHMe— | —CH$_2$— | |
| 67 | NHC(=O)Me | H | H | —C=C—C=C— | 3-F | —CH$_2$— | —CH$_2$— | |
| 68 | NMeC(=O)Me | H | H | —C=C—C=C— | 3-F | —CH$_2$— | —CH$_2$— | |
| 69 | NHC(=O)CH$_2$—OMe | H | H | —C=C—C=C— | 3-F | —CH$_2$— | —CH$_2$— | |
| 70 | NHC(=O)CF$_3$ | H | H | —C=C—C=C— | 3-F | —CH$_2$— | —CH$_2$— | |
| 71 | NHC(=O)CH$_2$—CH$_2$—Cl | H | H | —C=C—C=C— | 3-F | —CH$_2$— | —CH$_2$— | |
| 72 | NHC(=O)CH=CH$_2$ | H | H | —C=C—C=C— | 3-F | —CH$_2$— | —CH$_2$— | |
| 73 | NHC(=O)Ph | H | H | —C=C—C=C— | 3-F | —CH$_2$— | —CH$_2$— | |
| 74 | NMe$_2$ | H | H | —C=C—C=C— | 3-F | —CH$_2$— | —CH$_2$— | |

TABLE 1-continued

Compounds of the formula (I-A)

$$\text{(I-A)}$$

| No. | NR$^1$R$^2$ | R$^3$ | R$^4$ | —X$^1$=X$^2$—X$^3$=X$^4$— | (R$^5$)$_n$ | (Y$^1$)$_m$ | Y$^2$ | State/m.p. (° C.) |
|---|---|---|---|---|---|---|---|---|
| 75 | Morpholino | H | H | —C=C—C=C— | 3-F | —CH$_2$— | —CH$_2$— | |
| 76 | NHAc | H | H | —C=C—C=C— | 1-Me, 3-Me | —CH$_2$—CH$_2$— | —S— | |
| 77 | NHNH$_2$ | H | H | —C=C—C=C— | 1-Me, 3-Me | —CH$_2$—CH$_2$— | —S— | |
| 78 | NHpiperidino | H | H | —C=C—C=C— | 1-Me, 3-Me | —CH$_2$—CH$_2$— | —S— | |
| 79 | NH$_2$ | H | H | —C=C—C=C— | 2-Me, 4-Me | —CH$_2$—CH$_2$— | —S— | 114-116 |
| 80 | NH$_2$ | H | H | —C=C—C=C— | 1-Me, 2-Me, 3-Me | —CH$_2$—CH$_2$— | —S— | |
| 81 | NH$_2$ | H | H | —C=C—C=C— | 1Me, 3-Me | —CH$_2$—CHMe— | —S— | |
| 82 | NH$_2$ | H | H | —C=C—C=C— | 2-Me, 4-Me | —CH$_2$— | —S— | |
| 83 | NH$_2$ | H | H | —C=C—C=C— | 1-Me, 3-Me | —CMeH—CH$_2$— | —S— | |
| 84 | NH$_2$ | H | H | —C=C—C=C— | 4-Me | —CH$_2$—CHPh— | —S— | |
| 85 | NH$_2$ | H | H | —C=C—C=C— | 1-Me, 4-Me | —CH$_2$—CMe$_2$— | —S— | |
| 86 | NH$_2$ | H | H | —C=C—C=C— | 1-F, 3-F | —CH$_2$— | —S— | |
| 87 | NH$_2$ | H | H | —C=C—C=C— | 3-Me | —CH$_2$— | —S— | |
| 88 | NH$_2$ | H | H | —C=C—C=C— | 1-Me, 4-Me | —CH$_2$— | —S— | |
| 89 | NH$_2$ | H | H | —C=C—C=C— | 1-Me, 3-Cl | —CH$_2$— | —S— | |
| 90 | NMe$_2$ | H | H | —C=C—C=C— | 1-Me, 3-Me | —CH$_2$— | —S— | |
| 91 | Morpholino | H | H | —C=C—C=C— | 1-Me, 3-Me | —CH$_2$—CH$_2$— | —SO$_2$— | |
| 92 | NHAc | H | H | —C=C—C=C— | 1-Me, 3-Me | —CH$_2$— | —S— | |
| 93 | NHNH$_2$ | H | H | —C=C—C=C— | 1-Me, 3-Me | —CH$_2$— | —S— | |
| 94 | NHPiperidino | H | H | —C=C—C=C— | 1-Me, 3-Me | —CH$_2$— | —S— | |
| 95 | NH$_2$ | H | H | —C=C—C=C— | 2-Me, 4-Me | —CH$_2$— | —S— | |
| 96 | NH$_2$ | H | H | —C=C—C=C— | 1-Me, 3-F | —CH$_2$— | —S— | |
| 97 | NH$_2$ | H | H | —C=C—C=C— | 1Me, 3-OMe | —CH$_2$— | —S— | |
| 98 | NMe$_2$ | H | H | —C=C—C=C— | 2-Me, 4-Me | —CH$_2$— | —O— | |
| 99 | NH$_2$ | H | H | —C=C—C=C— | 1-Me, 3-Me | —CMeH—CH$_2$— | —O— | |
| 100 | NH$_2$ | H | H | —C=C—C=C— | 4-Me | —CH$_2$—CHPh— | —O— | |
| 101 | NH$_2$ | H | H | —C=C—C=C— | 1-Me, 4-Me | —CH$_2$—CMe$_2$— | —O— | |
| 102 | NH$_2$ | H | H | —C=C—C=C— | 1-F, 3-F | —CH$_2$— | —O— | |
| 103 | NH$_2$ | H | H | —C=C—C=C— | 1-Me, 3-Me | —CH$_2$— | —O— | |
| 104 | NH$_2$ | H | H | —C=C—C=C— | 1-Me, 4-Me | —CH$_2$— | —CO— | |
| 105 | NHMe | H | H | —C=C—C=C— | 1-Me, 3-Me | —CH$_2$— | —O— | |
| 106 | NMe$_2$ | H | H | —C=C—C=C— | 1-Me, 3-Me | —CH$_2$— | —O— | |
| 107 | Morpholino | H | H | —C=C—C=C— | 1-Me, 3-Me | —CH$_2$—CH$_2$— | —O— | |
| 108 | NHAc | H | H | —C=C—C=C— | 1-Me, 3-Me | —CH$_2$— | —O— | |
| 109 | NHNH$_2$ | H | H | —C=C—C=C— | 1-Me, 3-Me | —CH$_2$— | —O— | |
| 110 | NHPiperidino | H | H | —C=C—C=C— | 1-Me, 3-Me | —CH$_2$— | —O— | |
| 111 | NH$_2$ | H | H | —C=C—C=C— | 2-Me, 4-Me | —CMeH— | —O— | |
| 112 | NH$_2$ | Me | H | —C=C—C=C— | 1-Me, 3-Me | —CH$_2$— | —O— | |
| 113 | NH$_2$ | H | Me | —C=C—C=C— | 1Me, 3-Me | —CH$_2$— | —O— | |
| 114 | NH$_2$ | H | Me | —C=C—C=C— | 2-Me, 4-Me | —CH$_2$—CH$_2$— | —O— | |
| 115 | NH$_2$ | H | H | —C=C—C=C— | 1-Me, 2-OMe, 3-Me | —CH$_2$—CH$_2$— | —O— | |
| 116 | NHMe | H | H | —C=C—C=C— | 4-Me | —CH$_2$—CH$_2$— | —O— | |
| 117 | NH$_2$ | H | H | —C=C—C=C— | 1-Me, 2-OEt, 4-Me | —CH$_2$—CH$_2$— | —O— | |
| 118 | NH$_2$ | H | H | —C=C—C=C— | 1-F, 3-F | —CH$_2$—CH$_2$— | —O— | |
| 119 | NH$_2$ | H | —CH$_2$—OMe | —C=C—C=C— | 1-Me, 3-Me | —CH$_2$—CH$_2$— | —O— | |
| 120 | NH$_2$ | H | H | —C=C—C=C— | 2-OEt, 4-Me | —CH$_2$—CH$_2$— | —O— | |
| 121 | NH$_2$ | H | H | —C=C—C=C— | 1-Me, 3-Me | —CH$_2$—CH$_2$— | —O— | |
| 122 | NMe$_2$ | H | H | —C=C—C=C— | 1-Me, 3-Me | —CH$_2$—CH$_2$— | —O— | |
| 123 | Morpholino | Me | H | —C=C—C=C— | 1-Me, 3-Me | —CH$_2$—CH$_2$— | —O— | |
| 124 | NHAc | H | H | —C=C—C=C— | 1-Me, 3-Me | —CH$_2$—CH$_2$— | —O— | |
| 125 | NHNH$_2$ | H | H | —C=C—C=C— | 1-Me, 3-Me | —CH$_2$—CH$_2$— | —O— | |
| 126 | NHPiperidino | H | H | —C=C—C=C— | 1-Me, 3-Me | —CH$_2$—CH$_2$— | —O— | |
| 127 | NH$_2$ | H | H | —C=C—C=C— | 2-Me, 3-Me, 4-Me | —CH$_2$—CH$_2$— | —O— | |
| 128 | NH$_2$ | H | H | —C=C—C=C— | 2-Me, 3-Me | —CH$_2$—CH$_2$— | —O— | |
| 129 | NH$_2$ | H | H | —C=C—C=C— | 1Me, 3-Me | —CH$_2$—CHMe— | —O— | |
| 130 | NH$_2$ | H | H | —C=C—C=C— | 2-Me, 4-Me | —CH$_2$—CH$_2$— | —NH— | |
| 131 | NH$_2$ | H | H | —C=C—C=C— | 1-Me, 3-Me | —CH$_2$—CH$_2$— | —NMe— | |

TABLE 1-continued

Compounds of the formula (I-A)

| No. | NR$^1$R$^2$ | R$^3$ | R$^4$ | —X$^1$=X$^2$—X$^3$=X$^4$— | (R$^5$)$_n$ | (Y$^1$)$_m$ | Y$^2$ | State/m.p. (° C.) |
|---|---|---|---|---|---|---|---|---|
| 132 | NH$_2$ | H | H | —C=C—C=C— | 4-Me | —CH$_2$—CH$_2$— | —NH— | |
| 133 | NH$_2$ | H | H | —C=C—C=C— | 1-Me, 4-Me | —CH$_2$—CH$_2$— | —NAc— | |
| 134 | NH$_2$ | H | H | —C=C—C=C— | 1-F, 3-F | —CH$_2$—CH$_2$— | —NBz— | |
| 135 | NH$_2$ | H | H | —C=C—C=C— | 1-Me, 3-Me | —CH$_2$—CH$_2$— | —NH— | |
| 136 | NH$_2$ | H | H | —C=C—C=C— | 1-Me, 4-Me | —CH$_2$—CH$_2$— | —N(=O)— | |
| 137 | NH$_2$ | H | H | —C=N—C=N— | 1-Me, 3-Me | —CH$_2$—CH$_2$— | —NH— | |
| 138 | NMe$_2$ | H | H | —C=C—C=C— | 1-Me, 3-Me | —CH$_2$—CH$_2$— | —NPh— | |
| 139 | Morpholino | H | H | —C=C—C=C— | 1-Me, 3-Me | —CH$_2$—CH$_2$— | —NEt— | |
| 140 | NHAc | H | H | —C=C—C=C— | 1-Me, 3-Me | —CH$_2$—CH$_2$— | —N-i-Pr— | |
| 141 | NHNH$_2$ | H | H | —C=C—C=C— | 1-Me, 3-Me | —CH$_2$—CH$_2$— | —N-n-Pr— | |
| 142 | NHPiperidino | H | H | —C=C—C=C— | 1-Me, 3-Me | —CH$_2$—CH$_2$— | —NH— | |
| 143 | NH$_2$ | H | H | —S—C=C— | 4-Me | —CH$_2$—CH$_2$— | —NH— | |
| 144 | NH$_2$ | H | H | —C=C—S— | 1-Me, | —CH$_2$—CH$_2$— | —NH— | |
| 145 | NH$_2$ | H | H | —C=C—C=C— | 1Me, 3-Me | —CH$_2$—CHMe— | —NPh— | |
| 146 | NH$_2$ | H | H | —C=C—C=C— | 2-Me | —CH$_2$—CH$_2$— | — | solid foam |
| 146-R | NH$_2$ | H | H | —C=C—C=C— | 2-Me | —CH$_2$—CH$_2$— | — | 141-143; opt. rot.: 93.1°, c = 1, CHCl$_3$, 22° C.; EE: 95.7 % |
| 146-S | NH$_2$ | H | H | —C=C—C=C— | 2-Me | —CH$_2$—CH$_2$— | — | 141-143; opt. rot.: −94.4°, c = 1, CHCl$_3$, 22° C.; EE: 90.2% |
| 147 | NH$_2$ | H | H | —C=C—C=C— | 2-Et | —CH$_2$—CH$_2$— | — | |
| 148 | NH$_2$ | H | H | —C=C—C=C— | 2-i-Pr | —CH$_2$—CH$_2$— | — | |
| 149 | NH$_2$ | H | H | —C=C—C=C— | 2-OMe, 4-Me | —CH$_2$—CH$_2$— | — | |
| 150 | NH-Piperidino | H | H | —C=C—C=C— | 2-Me, 4-Me | —CH$_2$—CH$_2$— | — | |
| 151 | NH$_2$ | H | H | —C=C—C=C— | 2-Me, 4-Ph | —CH$_2$— | —O— | |
| 152 | NH$_2$ | H | H | —C=C—C=C— | 2-F, 4-Me | —CH$_2$—CH$_2$— | — | |
| 153 | NH$_2$ | H | H | —C=C—C=C— | 2-Me, 4-Ph | —CH$_2$—CH$_2$— | — | |
| 154 | NH$_2$ | H | H | —C=C—C=C— | 2-Me, 3-Cl, 4-Cl | —CH$_2$—CH$_2$— | — | |
| 155 | NH$_2$ | H | H | —C=C—C=C— | 2-Me, 4-OMe | —CH$_2$—CH$_2$— | — | |
| 156 | NH$_2$ | H | H | —C=C—C=C— | 2-Me, 4-F | —CH$_2$—CH$_2$— | — | |
| 157 | NH$_2$ | Me | Me | —C=C—C=C— | 2-Me, 4-Me | —CH$_2$—CH$_2$— | — | |
| 158 | NH$_2$ | H | H | —C=C—C=C— | 2-Et, 4-Me | —CH$_2$—CH$_2$— | — | |
| 159 | NH$_2$ | H | H | —C=C—C=C— | 2-i-Pr, 4-Me | —CH$_2$—CH$_2$— | — | |
| 160 | NH$_2$ | H | H | —C=C—C=C— | 2-Me, 4-Me | —CMeH—CH$_2$— | — | 127-129 |
| 161 | NH$_2$ | H | H | —C=C—C=C— | 1-Me, 4-Cl | —CH$_2$—CH$_2$— | — | |
| 162 | NHC(=O)—CH$_2$—CH$_2$—Cl | H | H | —C=C—C=C— | 1-Me, 4-Me | —CH$_2$—CH$_2$— | — | |
| 163 | NH$_2$ | Ac | H | —C=C—C=C— | 1-Me, 4-Me | —CH$_2$—CH$_2$— | — | |
| 164 | NH$_2$ | H | H | —C=C—C=C— | 2-Me, 3-F | —CH$_2$—CH$_2$— | — | 108-115 |
| 165 | NH$_2$ | H | H | —C=C—C=C— | 2-Cl, 3-Me | —CH$_2$—CH$_2$— | — | |
| 166 | NH$_2$ | H | H | —C=C—C=C— | 2-CH$_2$—CH$_2$—CH$_2$-3 | —CH$_2$—CH$_2$— | — | |
| 167 | NH$_2$ | H | H | —C=C—C=C— | 3-Et | —CH$_2$—CH$_2$— | — | |
| 168 | NH$_2$ | H | H | —O—C=C— | 3-Me | —CH$_2$—CH$_2$— | — | |
| 169 | NH$_2$ | H | H | —C=C—C=C— | 1-Me, 3-Et | —CH$_2$—CH$_2$— | — | |
| 170 | NH$_2$ | H | H | —C=C—C=C— | 1-Me, 3-Me | —CH$_2$—CH$_2$— | — | |
| 171 | NH$_2$ | H | H | —C=C—C=C— | 2-Me, 4-Me | —CH$_2$—CH$_2$— | — | |
| 172 | NH$_2$ | H | H | —C=C—C=C— | 1-Me, 3-Me, 4-Me | —CH$_2$—CH$_2$— | — | |
| 173 | NH$_2$ | H | H | —N=C—C=C— | 2-Me, 4-Me | —CH$_2$—CH$_2$— | — | |

TABLE 1-continued

Compounds of the formula (I-A)

| No. | NR$^1$R$^2$ | R$^3$ | R$^4$ | —X$^1$=X$^2$—X$^3$=X$^4$— | (R$^5$)$_n$ | (Y$^1$)$_m$ | Y$^2$ | State/m.p. (° C.) |
|---|---|---|---|---|---|---|---|---|
| 174 | NH$_2$ | H | H | —N=C—C=C— | 3-Me | —CH$_2$—CH$_2$— | — | |
| 175 | NH$_2$ | H | H | —C=C—C=N— | 1-Me, 3-Me | —CH$_2$—CH$_2$— | — | |
| 176 | NH$_2$ | Me | H | —C=C—C=C— | 2-Me | —CH$_2$—CH$_2$— | — | |
| 177 | NH$_2$ | H | H | —C=C—C=C— | 2-Et, 3-Me | —CH$_2$—CH$_2$— | — | |
| 178 | NH$_2$ | H | H | —C=C—C=C— | 3-COOMe | —CH$_2$—CH$_2$— | — | |
| 179 | NH$_2$ | H | H | —C=C—C=C— | 2-COOEt | —CH$_2$—CH$_2$— | — | |
| 180 | NH$_2$ | H | H | —C=C—C=C— | 2-CF$_3$ | —CH$_2$—CH$_2$— | — | |
| 181 | NH$_2$ | H | H | —C=C—C=C— | 2-c-propyl | —CH$_2$—CH$_2$— | — | |
| 182 | NH$_2$ | H | H | —C=C—C=C— | 2-CClF$_2$ | —CH$_2$—CH$_2$— | — | |
| 183 | NH$_2$ | H | H | —C=C—C=C— | 1-Me, 2-Me, 3-Me | —CH$_2$—CH$_2$— | — | |
| 184 | NH$_2$ | H | H | —C=C—C=C— | 2-CH$_2$—OMe | —CH$_2$—CH$_2$— | — | |
| 185 | NH$_2$ | H | H | —C=C—C=C— | H | —CH$_2$—CH$_2$— | — | 183-185 |
| 185-R | NH$_2$ | H | H | —C=C—C=C— | H | —CH$_2$—CH$_2$— | — | 149-151; opt. rot.: 93.3°, c = 1, CHCl$_3$, 21° C.; |
| 185-S | NH$_2$ | H | H | —C=C—C=C— | H | —CH$_2$—CH$_2$— | — | 149-151; opt. rot.: −84.6°, c = 1, CHCl$_3$, 21° C.; |
| 186 | NH$_2$ | H | H | —C=C—C=C— | 2-Ac | —CH$_2$—CH$_2$— | — | |
| 187 | NH$_2$ | H | H | —C=C—C=C— | 2-Ac, 4-Me | —CH$_2$—CH$_2$— | — | |
| 188 | NH$_2$ | H | H | —C=C—C=C— | 2-CN | —CH$_2$—CH$_2$— | — | |
| 189 | NH$_2$ | H | H | —C=C—C=C— | 2-Ph | —CH$_2$—CH$_2$— | — | |
| 190 | NH$_2$ | H | H | —C=C—C=C— | 2-(2-thienyl) | —CH$_2$—CH$_2$— | — | |
| 191 | NH$_2$ | H | H | —C=C—C=C— | 4-Ph | —CH$_2$—CH$_2$— | — | |
| 192 | NHPh | H | H | —C=C—C=C— | 2-Me | —CH$_2$—CH$_2$— | — | |
| 193 | NH$_2$ | Ph | H | —C=C—C=C— | 2-Me | —CH$_2$—CH$_2$— | — | |
| 194 | NH$_2$ | C(=O)—CH$_2$—OMe | H | —C=C—C=C— | 1-Me | —CH$_2$—CH$_2$— | — | |
| 195 | NHBz | H | H | —C=C—C=C— | 2-Me, 3-Me | —CH$_2$—CH$_2$— | — | |
| 196 | NH$_2$ | H | H | —C=C—C=C— | 1-Me, 2-F, 4-Me | —CH$_2$—CH$_2$— | — | |
| 197 | NH$_2$ | H | H | —C=C—C=C— | 3-F, 4-Me | —CH$_2$—CH$_2$— | — | 122-123 |
| 198 | NH$_2$ | H | H | —C=C—C=C— | H | —CHMe—CH$_2$— | — | 103-105 |
| 199 | NH$_2$ | CH$_2$—OMe | H | —C=C—C=C— | H | —CH$_2$—CH$_2$— | — | |
| 200 | NH$_2$ | CH$_2$—CH$_2$—OMe | H | —C=C—C=C— | H | —CH$_2$—CH$_2$— | — | |
| 201 | NH$_2$ | Ac | H | —C=C—C=C— | H | —CH$_2$—CH$_2$— | — | |
| 202 | NH$_2$ | H | H | —S—C=C— | H | —CH$_2$—CH$_2$— | — | |
| 203 | NH$_2$ | H | H | —C=C—C=C— | H | —CH$_2$— | —O— | 188-192 |
| 204 | NH$_2$ | H | H | —C=C—C=C— | 2-OH | —CH$_2$—CH$_2$— | — | |
| 205 | NH$_2$ | H | H | —C=C—C=C— | 3-CH=CH$_2$ | —CH$_2$—CH$_2$— | — | |
| 206 | NH$_2$ | Bz | H | —C=C—C=C— | H | —CH$_2$—CH$_2$— | — | |
| 207 | NH$_2$ | H | Me | —C=C—C=C— | H | —CH$_2$—CH$_2$— | — | |
| 208 | NH$_2$ | H | H | —C=C—C=C— | 3-C≡CH | —CH$_2$—CH$_2$— | — | |
| 209 | NH$_2$ | Ph | H | —C=C—C=C— | H | —CH$_2$—CH$_2$— | — | |
| 210 | NH$_2$ | H | H | —C=C—C=C— | 2-C≡CH | —CH$_2$—CH$_2$— | — | |
| 211 | NH$_2$ | Me | H | —C=C—C=C— | 2-CH=CH$_2$ | —CH$_2$—CH$_2$— | — | |
| 212 | NH$_2$ | H | H | —C=C—C=C— | 2-CH=CH$_2$ | —CMeH—CH$_2$— | — | |
| 213 | NH$_2$ | H | H | —C=C—C=C— | 2-I | —CH$_2$—CH$_2$— | — | |
| 214 | NH$_2$ | H | H | —C=C—C=C— | 3-I | —CH$_2$—CH$_2$— | — | |
| 215 | NH$_2$ | CHO | H | —C=C—C=C— | H | —CH$_2$—CH$_2$— | — | |
| 216 | NH$_2$ | H | H | —C=C—C=C— | 2-Br | —CH$_2$—CH$_2$— | — | |

TABLE 1-continued

Compounds of the formula (I-A)

(I-A)

| No. | NR¹R² | R³ | R⁴ | —X¹=X²—X³=X⁴— | (R⁵)ₙ | (Y¹)ₘ | Y² | State/m.p. (° C.) |
|---|---|---|---|---|---|---|---|---|
| 217 | NH₂ | H | H | —C=C—C=C— | 3-Br | —CH₂—CH₂— | — | |
| 218 | NH₂ | H | H | —C=C—C=C— | 2-NHCHO | —CH₂—CH₂— | — | |
| 219 | NH₂ | H | H | —C=C—C=C— | 2-NHAc | —CH₂—CH₂— | — | |
| 220 | NH₂ | H | H | —C=C—C=C— | 2-NHCO—Ph | —CH₂—CH₂— | — | |
| 221 | NH₂ | H | H | —C=C—C=C— | 2-NHPh | —CH₂—CH₂— | — | |
| 222 | NH₂ | H | H | —C=C—C=C— | 2-Ph, 4-Me | —CH₂—CH₂— | — | |
| 223 | NH₂ | H | H | —C=C—C=C— | 2-O—Ph | —CH₂—CH₂— | — | |
| 224 | NH₂ | H | H | —C=C—C=C— | 2-OMe | —CH₂—CH₂— | — | |
| 225 | NH₂ | H | H | —C=C—C=C— | 2-OEt | —CH₂—CH₂— | — | |
| 226 | NH₂ | H | H | —C=C—C=C— | 2-O-i-Pr | —CH₂—CH₂— | — | |
| 227 | NH₂ | H | H | —C=C—C=C— | 4-OMe | —CH₂—CH₂— | — | |
| 228 | NH₂ | H | H | —C=C—C=C— | 4-OEt | —CH₂—CH₂— | — | |
| 229 | NH₂ | H | H | —C=C—C=C— | 4-O-i-Pr | —CH₂—CH₂— | — | |
| 230 | NH₂ | H | H | —C=N—C=N— | H | —CH₂—CH₂— | — | |
| 231 | NH₂ | H | H | —N=C—C=N— | H | —CH₂—CH₂— | — | |
| 232 | NH₂ | H | H | —C=N—N=C— | H | —CH₂—CH₂— | — | |
| 233 | NH₂ | H | H | —N=C—C=N— | H | —CH₂—CH₂— | — | |
| 234 | NH₂ | H | H | —N=C—N=C— | 2-Me | —CH₂—CH₂— | — | |
| 235 | NH₂ | H | H | —N=C—N=C— | 2-CF₃ | —CH₂—CH₂— | — | |
| 236 | NH₂ | H | H | —N=C—N=C— | 2-(1-fluoro)-Et | —CH₂—CH₂— | — | |
| 237 | NH₂ | H | H | —N=C—N=C— | 2-(1-fluoro)-i-Pr | —CH₂—CH₂— | — | |
| 238 | NH₂ | H | H | —N=C—N=C— | 4-OMe | —CH₂—CH₂— | — | |
| 239 | NH₂ | H | H | —N=C—N=C— | 2-OMe | —CH₂—CH₂— | — | |
| 240 | NH₂ | H | H | —N=C—N=C— | 2Me, 4-OMe | —CH₂—CH₂— | — | |
| 241 | NH₂ | H | H | —N=C—N=C— | 2-OMe, 4-OMe | —CH₂—CH₂— | — | |
| 242 | NHAc | H | H | —N=C—N=C— | 2-OMe, 4-OMe | —CH₂—CH₂— | — | |
| 243 | NHAc | H | H | —N=C—C=C— | 2-OMe | —CH₂—CH₂— | — | |
| 244 | NH₂ | H | H | —N=C—C=C— | 2-OMe | —CH₂—CH₂— | — | |
| 245 | NH₂ | H | H | —N=C—C=C— | 4-OMe | —CH₂—CH₂— | — | |
| 246 | NH₂ | H | H | —C=C—C=N— | 2-OMe | —CH₂—CH₂— | — | |
| 247 | NH₂ | H | H | —C=C—C=N— | H | —CH₂—CH₂— | — | |
| 248 | NH₂ | CHO | H | —C=C—C=C— | H | —CH₂—CH₂— | — | |
| 249 | NH₂ | H | —CH₂—OMe | —C=C—C=C— | H | —CH₂—CH₂— | — | |
| 250 | NH₂ | H | Me | —C=C—C=C— | H | CH₂ | O | |
| 251 | NH₂ | H | H | —C=C—C=C— | H | CH₂ | NMe | |
| 252 | NH₂ | H | H | —C=C—C=C— | 1-Me, 4-Me | CH₂ | O | |
| 253 | NH₂ | H | H | —C=C—C=C— | 1-Me, 4-F | CHMeCH₂ | | |
| 254 | NH₂ | Me | COO—Me | —C=C—C=C— | 2-Me, 4-Cl | CH₂CPhH | O | |
| 255 | NH₂ | Me | CN | —C=C—C=C— | 2-Me, 4-Me | CH₂ | CH₂ | |
| 256 | NH₂ | Ac | Ac | —C=C—C=C— | 2-Me, 4-Me | CH₂ | CH₂ | |
| 257 | NH₂ | CHO | Me | —C=C—C=C— | 2-Me, 4-Me | CH₂ | CH₂ | |
| 258 | NMe₂ | H | H | —C=C—C=C— | 2-Me, 4-Me | CH₂ | CH₂ | |
| 259 | NHCHO | CH₂O—Me | H | —C=C—C=C— | 2-Me, 4-CF₃ | CH₂ | — | |
| 260 | Morpholino | Bz | Me | —C=C—C=C— | 1-Me, 4-OMe | CH₂—CHMe | NMe | |
| 261 | Piperidino | H | H | —C=C—C=C— | 3-OMe | CH₂—CH₂ | CHMe | |
| 262 | NHAc | H | H | —C=C—C=C— | 2-Me, 4-Me | CH₂—CHPh | — | |
| 263 | NHNH₂ | Me | H | —C=C—C=C— | 3-Me, 4-Me | CH₂—CHMe | S | |
| 264 | NEt₂ | H | H | —C=C—C=C— | 3-Me, 4-Et | CHMe—CH₂ | S | |
| 265 | NHPh | H | H | —C=C—C=C— | 2-Ac, 4-Me | CH₂—CH₂ | S | |
| 266 | NHBz | H | H | —C=C—C=C— | 3-OPh | CH₂—CH₂ | S | |
| 267 | NHCOPh | H | H | —C=C—C=C— | 3-OCOPh | CH₂—CH₂ | O | |
| 268 | NH₂ | 4-Cl—Bz | H | —C=C—C=C— | 2-Me, 4-Me | CH₂—CH₂ | O | |
| 269 | NH₂ | H | Me | —C=C—C=C— | 2-Me, 4-Me | CH₂—CH₂ | S | |
| 270 | NH₂ | H | Et | —C=C—C=C— | 2-Me, 4-OEt | CH₂—CH₂ | S | |

TABLE 1-continued

Compounds of the formula (I-A)

(I-A)

| No. | NR¹R² | R³ | R⁴ | —X¹=X²—X³=X⁴— | (R⁵)ₙ | (Y¹)ₘ | Y² | State/m.p. (° C.) |
|---|---|---|---|---|---|---|---|---|
| 271 | NH₂ | H | H | —C=C—C=N— | 2-Me | CH₂—CH₂ | S | |
| 272 | NH₂ | H | H | —C=C—C=N— | H | —CH₂—CH₂— | — | |
| 273 | NHMe | H | H | —N=C—N— | 3-Me | —CH₂—CH₂— | CH₂ | |
| 274 | NHMe | H | H | —N=C—N— | 2-Me, 3-Me | —CH₂—CH₂— | CH₂ | |
| 275 | NH₂ | H | H | —N=C—N— | 3-Me | —CH₂—CH₂— | CH₂ | |
| 276 | NH₂ | H | H | —N=C—N— | 2-Me, 3-Me | —CH₂—CH₂— | CH₂ | |
| 277 | NHMe | H | H | —N=C—N— | 3-Me | —CH₂—CH₂— | — | |
| 278 | NHMe | H | H | —N=C—N— | 2-Me, 3-Me | —CH₂—CH₂— | — | |
| 279 | NH₂ | H | H | —N=C—N— | 3-Me | —CH₂—CH₂— | — | |
| 280 | NH₂ | H | H | —N=C—N— | 2-Me, 3-Me | —CH₂—CH₂— | — | |
| 281 | NH₂ | H | H | —C=C—C=C— | 2-Me, | —CHMe—CH₂— | — | 198-200 |
| 282 | NH₂ | H | H | —C=C—C=C— | 2-F, | —CHMe—CH₂— | — | 95-97 |
| 283 | NHAc | H | H | —C=C—C=C— | 2-F, | —CHMe—CH₂— | — | 175-177 |
| 284 | NHC(=O)CCl₃ | H | H | —C=C—C=C— | 2-F, | —CHMe—CH₂— | — | |
| 285 | NHC(=O)CF₃ | H | H | —C=C—C=C— | 2-F, | —CHMe—CH₂— | — | waxlike |
| 286 | NHC(=O)CH₂Cl | H | H | —C=C—C=C— | 2-F, | —CHMe—CH₂— | — | waxlike |
| 287 | NHC(=O)C₂H₅ | H | H | —C=C—C=C— | 2-F, | —CHMe—CH₂— | — | |
| 288 | NH₂ | H | H | —C=C—C=C— | 2-F, 4-Me | —CH₂—CH₂— | O | 96-99 |
| 289 | NH₂ | H | H | —C=C—C=C— | 2-F, | —CH₂—CH₂— | O | 92-94 |
| 290 | NH₂ | H | H | —C=C—C=C— | 1-Me | —CHMe—CH₂— | — | solid foam |
| 291 | NH₂ | H | H | —C=C—C=C— | 2-Me | —CHEt—CH₂— | — | solid foam |
| 292 | NH₂ | H | H | —C=C—C=C— | 2-Me | —CMe₂—CH₂— | — | 186-188 |
| 293 | NH₂ | H | H | —C=C—C=C— | 2-Me, 3-Me | —CHMe—CH₂— | — | 155-160 |
| 294 | NH₂ | H | H | —C=C—C=C— | 4-Me | —CHMe—CH₂— | — | |
| 295 | NH₂ | H | H | —C=C—C=C— | H | CH₂CH₂CH₂ | O | |
| 296 | NH₂ | H | H | —C=C—C=C— | 1,2-Me, 4-F | —CH₂—CH₂— | — | 211-212 |
| 297 | NH₂ | H | H | —C=C—C=C— | 1,4-Cl | —CH₂—CH₂— | — | 210 |
| 297 | NH₂ | H | H | —C=C—C=C— | 1-Me | —CH₂—CH₂— | — | solid foam |
| 297 | NH₂ | H | H | —C=C—C=C— | 1,4-F | —CH₂—CH₂— | — | 158-161 |
| 197 | NH₂ | H | H | —C=C—C=C— | 1-F, 3-Me | —CH₂—CH₂— | — | 194-204 |
| 297 | NH₂ | H | H | —C=C—C=C— | 2,3-F | —CH₂—CH₂— | — | oil |
| 297 | NH₂ | H | H | —C=C—C=C— | 2,3,4-Me | —CHCH₃— | —CH₂— | solid foam |
| 298 | NH₂ | H | H | —C=C—C=C— | 4-OMe | —CH₂— | —O— | solid foam |
| 299 | NH₂ | H | H | —C=C—C=C— | 1,2-Me | —CH₂—CH₂— | — | oil |
| 300 | NH₂ | H | H | —C=C—C=C— | 3-Me, 4-Cl | —CH₂—CH₂— | — | 217-218 |
| 301 | NHC(=C)CH₃ | H | H | —C=C—C=C— | 2-Me | —CH₂—CH₂— | —O— | 186-188 |
| 302 | NH₂ | H | H | —C=C—C=C— | 2-Me | —CH₂—CH₂— | —O— | 102-104 |
| 303 | NH₂ | H | H | —C=C—C=C— | 4-Me | —CHCH₃— | —CH₂— | solid foam |

TABLE 2

Compounds of the formula (I-B)

(I-B)

| No. | NR¹R² | R³ | R⁴ | =X¹—X²=X³—X⁴= | (R⁵)ₙ | (Y¹)ₘ | Y² | State/ m.p. (° C.) |
|---|---|---|---|---|---|---|---|---|
| B-1 | NH₂ | H | H | =N—S—C= | H | —CH₂—CH₂— | — | |
| B-2 | NH₂ | H | H | =N—S—C= | 4-Me | —CH₂—CH₂— | — | |

TABLE 2-continued

Compounds of the formula (I-B)

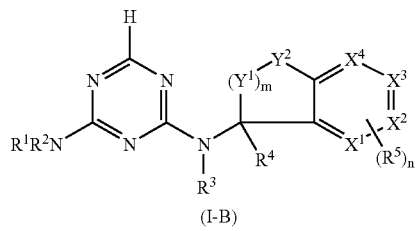

(I-B)

| No. | NR$^1$R$^2$ | R$^3$ | R$^4$ | =X$^1$—X$^2$=X$^3$—X$^4$= | (R$^5$)$_n$ | (Y$^1$)$_m$ | Y$^2$ | State/ m.p. (° C.) |
|---|---|---|---|---|---|---|---|---|
| B-3 | NH$_2$ | H | H | =N—S—C= | 4-OMe | —CH$_2$—CH$_2$— | — | |
| B-4 | NH$_2$ | H | H | =N—O—C= | H | —CH$_2$—CH$_2$— | — | |
| B-5 | NH$_2$ | H | H | =N—O—C= | 4-Me | —CH$_2$—CH$_2$— | — | |
| B-6 | NH$_2$ | H | H | —=N—O—C= | 4-OMe | —CH$_2$—CH$_2$— | — | |
| B-7 | NH$_2$ | H | H | =C—O—N= | H | —CH$_2$—CH$_2$— | — | |
| B-8 | NH$_2$ | H | H | =C—O—N= | 2-Me | —CH$_2$—CH$_2$— | — | |
| B-9 | NH$_2$ | H | H | =C—O—N= | 2-OMe | —CH$_2$—CH$_2$— | — | |
| B-10 | NH$_2$ | H | H | =N—O—N= | H | —CH$_2$—CH$_2$— | — | |
| B-11 | NH$_2$ | H | H | =N—S—N= | H | —CH$_2$—CH$_2$— | — | |
| B-12 | NHMe | H | H | =N—S—C= | H | —CH$_2$—CH$_2$— | — | |
| B-13 | NH$_2$ | H | H | =N—S—C= | H | —CH$_2$—CH$_2$— | CH$_2$ | |
| B-14 | NH$_2$ | H | H | =N—S—C= | 4-Me | —CH$_2$—CH$_2$— | CH$_2$ | |
| B-15 | NH$_2$ | H | H | =N—S—C= | 4-OMe | —CH$_2$—CH$_2$— | CH$_2$ | |
| B-16 | NH$_2$ | H | H | =N—O—C= | H | —CH$_2$—CH$_2$— | CH$_2$ | |
| B-17 | NH$_2$ | H | H | =N—O—C= | 4-Me | —CH$_2$—CH$_2$— | CH$_2$ | |
| B-18 | NH$_2$ | H | H | =N—O—C= | 4-OMe | —CH$_2$—CH$_2$— | CH$_2$ | |
| B-19 | NH$_2$ | H | H | =C—O—N= | H | —CH$_2$—CH$_2$— | CH$_2$ | |
| B-20 | NH$_2$ | H | H | =C—O—N= | 2-Me | —CH$_2$—CH$_2$— | CH$_2$ | |
| B-21 | NH$_2$ | H | H | =C—O—N= | 2-OMe | —CH$_2$—CH$_2$— | CH$_2$ | |
| B-22 | NH$_2$ | H | H | =N—O—N= | H | —CH$_2$—CH$_2$— | CH$_2$ | |
| B-23 | NH$_2$ | H | H | =N—S—N= | H | —CH$_2$—CH$_2$— | CH$_2$ | |
| B-24 | NHMe | H | H | =N—S—C= | H | —CH$_2$—CH$_2$— | CH$_2$ | |

B. FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert material, 10 parts by weight of potassium lignosulfonate and 1 part by weight of sodium oleoylmethyltaurate as wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether ®Triton X 207), 3 parts by weight of isotridecanol polyglycol ether (8 EO) and 71 parts by weight of paraffinic mineral oil (boiling range for example approx. 255 to over 277° C.) and grinding the mixture in a grinding-ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Water-dispersible granules are obtained by mixing

| | | |
|---|---|---|
| 75 parts by weight | of a compound of the formula (I), | |
| 10 " | of calcium lignosulfonate, | |
| 5 " | of sodium laurylsulfate, | |
| 3 " | of polyvinyl alcohol and | |
| 7 " | of kaolin, | | grinding the mixture on a pinned-disk mill and granulating the powder in a fluidized bed by spraying on water as granulation liquid.

f) Water-dispersible granules are also obtained by homogenizing and precomminuting

| | | |
|---|---|---|
| 25 parts by weight | of a compound of the formula (I), | |
| 5 " | of sodium 2,2'-dinaphthylmethane-6,6'-disulfonate, | |
| 2 " | of sodium oleoylmethyltaurate, | |
| 1 part by weight | of polyvinyl alcohol, | |
| 17 parts by weight | of calcium carbonate and | |
| 50 " | of water | | in a colloid mill, subsequently grinding the mixture in a bead mill and atomizing and drying the resulting suspension in a spray tower by means of a single-substance nozzle.

C. BIOLOGICAL EXAMPLES

1. Pre-emergence Herbicidal Action

Seeds or rhizome pieces of monocotyledonous and dicotyledonous weed plants are placed in sandy loam in plastic pots and covered with soil. The compounds according to the invention, which are formulated in the form of wettable powders or emulsion concentrates, are then applied to the surface of the soil cover as aqueous suspension or emulsion at various dosages with an application rate of 600 to 800 l of water/ha (converted).

After the treatment, the pots are placed into a greenhouse and kept under good growth conditions for the weeds. The plant or emergence damage is scored visually after the untreated controls have emerged. As shown by the test results, the compounds according to the invention have good herbicidal pre-emergence activity against a broad spectrum of weed grasses and broad-leaved weeds. In the test, for example, the Examples Nos 1, 4, 5, 19, 55, 58, 79, 146, 185, 198, 281, 282, 283, 285, 286, 288, 289, 290, 291, 292 and 293 (see Tables 1 and 2) show very good herbicidal action against harmful plants such as *Sinapis alba, Chrysanthemum segetum, Avena sativa, Stellaria media, Echinochloa crus-galli, Lolium multiflorum, Setaria* spp., *Abutilon theophrasti, Amaranthus retrofluxus* and *Panicum miliaceum* when used by the pre-emergence method at an application rate of 0.5 kg and less of active substance per hectare.

2. Post-emergence Herbicidal Action

Seeds or rhizome pieces of monocotyledonous and dicotyledonous weeds are placed in sandy loam in plastic pots, covered with soil and grown in the greenhouse under good growth conditions. Three weeks after sowing, the test plants are treated at the three-leaf stage. Various dosages of the compounds according to the invention, which are formulated as wettable powders or emulsion concentrates, are sprayed onto the green plant parts at an application rate of 600 to 800 l of water per ha (converted), and after the test plants have been left to stand in the greenhouse for approx. 3 to 4 weeks under optimum growth conditions, the effect of the preparations is scored visually by comparison with untreated controls. The compositions according to the invention also have good herbicidal post-emergence activity against a broad spectrum of economically important weed grasses and broad-leaved weeds. In the test, the Examples 1, 4, 5, 19, 55, 58, 79, 146, 185, 198, 281, 282, 283, 285, 286, 288, 289, 290, 291, 292 and 293 (see Tables 1 and 2), for example, have very good herbicidal action against harmful plants such as *Sinapis alba, Echinochloa crus-galli, Lolium multiflorum, Chrysanthemum segetum, Setaria* spp., *Abutilon theophrasti, Amaranthus retroflexus* and *Panicum miliaceum, Avena sativa* when used by the post-emergence method at an application rate of 0.5 kg or less of active substance per hectare.

3. Action Against Harmful Plants in Rice

Transplanted and seeded rice and typical rice weeds are grown in the greenhouse until they have reached the three-leaf stage (*Echinochloa* 1.5-leaves) under paddy rice conditions (flooding level of the water: 2-3 cm) in closed plastic pots. They are then treated with the compounds according to the invention. To this end, the formulated active substances are suspended, dissolved or emulsified in water and applied to the paddy water of the test plants at various dosages by application by pouring.

After the treatment has been carried out in this way, the test plants are placed into the greenhouse under optimum growth conditions and are kept in this way over the entire experimental period.

Approximately three weeks after the application, the experiments are evaluated by visually scoring the plant damage in comparison with untreated controls, where, for example, the compounds Nos 1, 4, 5, 19, 55, 58, 79, 146, 185, 198, 281, 282, 283, 285, 286, 288, 289, 290, 291, 292 and 293 (see Tables 1 and 2) show very good herbicidal action against harmful plants which are typical for rice crops, such as, for example, *Cyperus monti, Echinochloa crus-galli, Eleocharis acicularis* and *Sagittaria pygmaea*.

4. Crop Plant Tolerance

In further greenhouse experiments, seeds of a relatively large number of crop plants and weeds are placed in sandy loam and covered with soil. Some of the pots are treated immediately as described in Section 1, while the remaining pots are placed in the greenhouse until the plants have developed two to three real leaves, and they are then sprayed with various dosages of substances of the formula (I) according to invention as described in Section 2. Four to five weeks after the application and standing time in the greenhouse, it is found by means of visual scoring that the compounds according to the invention leave dicotyledonous crops such as, for example, soybeans, cotton, oilseed rape, sugar beet and potatoes unharmed when applied pre- and post-emergence, even at high rates of active compound. In addition, some substances also leave graminaceous crops such as, for example, barley, wheat, rye, *sorghum*, corn or rice, unharmed. Inter alia, the compounds Nos 1, 4, 5, 19, 55, 58, 79, 146, 185, 198, 281, 282, 283, 285, 286, 288, 289, 290, 291, 292 and 293 (see Tables 1 and 2) of the formula (I) show in some cases high selectivity and are therefore suitable for controlling unwanted vegetation in agricultural crops.

The invention claimed is:

1. A compound of the formula (I) or a salt thereof

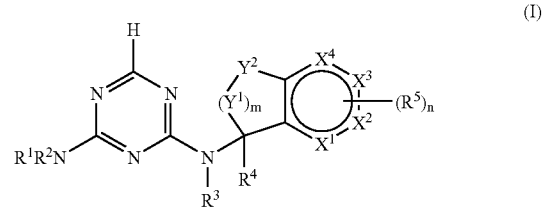

in which

R$^1$ and R$^2$ are each independently of one another hydrogen, a group of the formula NR'R", where R' and R" are each independently of one another H, (C$_1$-C$_6$)alkyl, (C$_2$-C$_6$) alkenyl, (C$_2$-C$_6$)alkynyl, (C$_3$-C$_6$)cycloalkyl or (C$_5$-C$_6$) cycloalkenyl, or an acyclic hydrocarbon radical or hydrocarbonoxy radical having in each case 1 to 10 carbon atoms or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted, or an acyl radical of an organic acid having 1 to 20 carbon atoms, or R$^1$ and R$^2$ together with the nitrogen atom of the group NR$^1$R$^2$ are a saturated or unsaturated, nonaromatic heterocyclic radical having 3 to 9 ring atoms and 1 to 4 hetero ring atoms, where the further hetero ring atoms optionally present in addition to the nitrogen atom are selected from the group consisting of N, O and S and the radical is unsubstituted or substituted, where each of the carbon-containing radicals $R^1$ and $R^2$ including substituents has 1 to 20 carbon atoms, $R^3$ is hydrogen, amino, $(C_1-C_4)$alkylamino, di$(C_1-C_4)$alkylamino, $(C_1-C_6)$alkyl, $(C_1-C_6)$alkoxy, $(C_2-C_6)$alkenyl, $(C_2-C_6)$alkynyl, $(C_3-C_6)$cycloalkyl, $(C_5-C_6)$cycloalkenyl, phenyl or heterocyclyl, where each of the 10 last-mentioned radicals independently of the others is unsubstituted or substituted and the radical in question including substituents has 1 to 12 carbon atoms, or an acyl radical of the formula -B*-A*, where A* is hydrogen or an acyclic or cyclic hydrocarbon radical having 1 to 10 carbon atoms which is unsubstituted or substituted, and B* is a divalent group of the formula —CO—, —CO—O—, —CO—NR'—, —S(O)$_p$— or —S(O)$_p$—O—, where p=0, 1 or 2 and R' is hydrogen, alkyl having 1 to 6 carbon atoms, phenyl, benzyl, cycloalkyl having 3 to 6 carbon atoms or alkanoyl having 1 to 6 carbon atoms, where -B*-A* including substituents has 1 to 12 carbon atoms, $R^4$ is a radical of the formula -$Z^1$-$R^6$, where $Z^1$ and $R^6$ are as defined below, $R^5$ are each independently of one another halogen, cyano, isocyanato, nitro, a radical of the formula -$Z^2$-$R^7$, where $Z^2$ and $R^7$ are as defined below, or two adjacent radicals $R^5$ together are a fused-on cycle having 4 to 6 ring atoms which is carbocyclic or contains 1 to 3 hetero ring atoms from the group consisting of O, S and N and which is unsubstituted or substituted by one or more radicals from the group consisting of halogen, $(C_1-C_4)$alkyl and oxo, $R^6$, $R^7$, $R^8$, $R^9$ are each independently of one another hydrogen, except that $R^7$ is not hydrogen if $Z^2$ is a direct bond, or an acyclic hydrocarbon radical having 1 to 20 carbon atoms or a cyclic hydrocarbon radical or a heterocyclic radical, where each of the three last-mentioned radicals is unsubstituted or substituted, or $R^8$ and $R^9$ together with the carbon atom of a group $CR^8R^9$ (for $Y^1$ $Y^2$) or two radicals $R^8$ or $R^9$ from two groups $Y^1$ and/or $Y^2$ together with the attached atoms of the groups $Y^1$ and/or $Y^2$ are in each case a carbocyclic radical having 3 to 8 carbon atoms or a heterocyclic radical, where each of the two last-mentioned radicals is unsubstituted or substituted, $X^1$, $X^2$, $X^3$, $X^4$ are each independently of one another a carbon atom which is substituted by a hydrogen atom or one of the substituents $R^5$ defined above, or a nitrogen atom, or two adjacent symbols $X^1$, $X^2$, $X^3$ and $X^4$ are in each case together a divalent group of the formula —O—, —S—, —NH— or —NR—, where R is as defined for $R^3$, provided the groups $X^1$, $X^2$, $X^3$, $X^4$ together with the attached $C_2$ unit of the fused-on ring form a carbocyclic or heterocyclic aromatic five- or six-membered ring, $(Y^1)_m$ are m divalent groups $Y^1$, where each group $Y^1$ independently of the other radicals $Y^1$ is a group of the formula —O—, —CO—, —C(=NR*)—, —S(O)$_q$—, —NR*— or —N(O)—, where q=0, 1 or 2 and R* is as defined for $R^3$, or a group of the formula $CR^8R^9$, where $R^8$ and $R^9$ are as defined above, and $Y^2$ is a group as defined for $Y^1$ or a direct bond, where two adjacent groups of the symbol pairs $Y^1$ and $Y^1$ or of the symbol pairs $Y^1$ and $Y^2$ are groups with no heteroatoms having the same meaning, and where the groups $(Y^1)_m$ and $Y^2$ together with the attached $C_2$ unit of the aromatic ring and the carbon atom attached to $R^4$ form a fused-on carbocyclic or heterocyclic nonaromatic four- to eight-membered ring, $Z^1$ and the groups $Z^2$ are each independently of one another a direct bond or a divalent group of the formula —O—, —S(O)$_p$—, —S(O)$_p$—O—, —O—S(O)$_p$—, —CO—, —O—CO—, —CO—O—, —NR'—, —O—NR'—, —NR'—O—, —NR'—CO—, —CO—NR'—, where p=0, 1 or 2 and R' is hydrogen, alkyl having 1 to 6 carbon atoms, phenyl, benzyl, $(C_3-C_6)$cycloalkyl or alkanoyl having 1 to 6 carbon atoms, m is 0, 1, 2, 3 or 4 and n is 0, 1, 2, 3 or 4.

2. A compound or a salt thereof as claimed in claim 1, wherein $R^1$ and $R^2$ are each independently of one another hydrogen, amino, alkylamino or dialkylamino having in each case 1 to 4 carbon atoms in the alkyl radical or $(C_3-C_6)$cycloalkylamino, $(C_5-C_6)$cycloalkenylamino, a hydrocarbon radical or hydrocarbonoxy radical having in each case 1 to 10 carbon atoms or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted by one or more radicals from the group consisting of halogen, hydroxyl, amino, nitro, formyl, aminocarbonyl, carboxyl, sulfonyl, cyano, thiocyanato, $(C_1-C_6)$alkoxy, $(C_2-C_6)$alkenyloxy, $(C_2-C_6)$alkynyloxy, $(C_1-C_6)$alkoxypoly(alkyleneoxy), hydroxy-poly(alkyleneoxy), $(C_1-C_6)$alkylthio, mono- and di[$(C_1-C_6)$alkyl]amino, [$(C_1-C_6)$alkyl]carbonyl, [$(C_2-C_6)$alkenyl]carbonyl, [$(C_2-C_6)$alkynyl]carbonyl, [$(C_1-C_6)$alkoxy]carbonyl, [$(C_2-C_6)$alkenyloxy]carbonyl, [$(C_2-C_6)$alkynyloxy]carbonyl, mono- and di[$(C_1-C_6)$alkyl]aminocarbonyl, phenyl, phenoxy, $(C_3-C_6)$cycloalkyl, phenylcarbonyl, phenoxycarbonyl, heterocyclyl, $(C_1-C_4)$alkylsulfonyl and, in the case of cyclic radicals, also $(C_1-C_4)$alkyl, where each of the 24 last-mentioned substituents is unsubstituted or substituted by one or more radicals from the group consisting of halogen, CN, SCN, NO$_2$, $(C_1-C_4)$alkoxy, $(C_1-C_4)$alkylthio, $(C_1-C_4)$haloalkoxy, formyl, $(C_1-C_4)$alkylcarbonyl, [$(C_1-C_4)$haloalkyl]carbonyl, [$(C_1-C_4)$alkoxy]carbonyl, [$(C_1-C_4)$haloalkoxy]carbonyl and, in the case of cyclic radicals, also $(C_1-C_4)$alkyl and $(C_1-C_4)$haloalkyl, or an acyl radical of an organic acid from the group consisting of formyl, aminocarbonyl, mono- and di[$(C_1-C_4)$alkyl]aminocarbonyl, [$(C_1-C_6)$alkyl]carbonyl, [$(C_2-C_6)$alkenyl]carbonyl, [$(C_2-C_6)$alkynyl]carbonyl, [$(C_1-C_6)$alkoxy]carbonyl, [$(C_2-C_6)$alkenyloxy]carbonyl, phenylcarbonyl, $(C_1-C_6)$alkylsulfonyl, where each of the 9 last-mentioned radicals is unsubstituted in the aliphatic moiety or in the phenyl ring or substituted by one or more radicals from the group consisting of halogen, CN, SCN, NO$_2$, $(C_1-C_4)$alkoxy, $(C_1-C_4)$haloalkoxy, optionally substituted and unsubstituted phenyl and, in the case of cyclic radicals, also $(C_1-C_6)$alkyl and $(C_1-C_6)$haloalkyl, or $R^1$ and $R^2$ together with the nitrogen atom of the group $NR^1R^2$ are a saturated or unsaturated, nonaromatic heterocyclic radical having 3 to 6 ring atoms and 1 to 4 hetero ring atoms, where the further hetero ring atoms optionally present in addition to the nitrogen atom are selected from the group consisting of N, O and S and the radical is unsubstituted or substituted by one or more radicals from the group consisting of halogen, CN, $(C_1$-

$C_4$)alkyl, $(C_1-C_4)$haloalkyl, $(C_1-C_4)$alkoxy, $(C_1-C_4)$haloalkoxy, $(C_1-C_4)$alkoxycarbonyl and oxo, $R^3$ is hydrogen, amino, $(C_1-C_6)$alkyl, $(C_1-C_6)$alkoxy, $(C_2-C_6)$alkenyl, $(C_2-C_6)$alkynyl, $(C_3-C_6)$cycloalkyl, $(C_5-C_6)$cycloalkenyl, phenyl or heterocyclyl, where each of the eight last-mentioned radicals is unsubstituted or substituted by one or more radicals from the group consisting of halogen, hydroxyl, amino, nitro, formyl, carboxyl, cyano, thiocyanato, $(C_1-C_4)$alkoxy, $(C_1-C_4)$alkoxy-$(C_1-C_4)$alkoxy, hydroxy-$(C_1-C_4)$alkoxy, $(C_1-C_4)$alkoxy-poly(alkyleneoxy), hydroxy-poly(alkyleneoxy), $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, $(C_3-C_6)$cycloalkyl, phenylcarbonyl, phenoxycarbonyl, heterocyclyl, where each of the 6 last-mentioned radicals is unsubstituted or substituted by one or more radicals from the group consisting of halogen, CN, SCN, $NO_2$, $(C_1-C_4)$alkyl, $(C_1-C_4)$haloalkyl, $(C_1-C_4)$alkoxy and $(C_1-C_4)$haloalkoxy, and $(C_1-C_4)$alkylsulfonyl and $(C_1-C_4)$haloalkylsulfonyl and, in the case of cyclic radicals, also $(C_1-C_4)$alkyl and $(C_1-C_4)$haloalkyl, or an acyl radical of the formula -B*-A*, where A* is hydrogen or $(C_1-C_6)$alkyl, $(C_2-C_6)$alkenyl, $(C_2-C_6)$alkynyl, $(C_3-C_6)$cycloalkyl, $(C_5-C_6)$cycloalkenyl or phenyl, where each of the six last-mentioned radicals is unsubstituted or substituted by one or more radicals from the group consisting of halogen, hydroxyl, amino, nitro, formyl, carboxyl, cyano, thiocyanato, $(C_1-C_4)$alkoxy, $(C_1-C_4)$haloalkoxy, $(C_1-C_4)$alkylthio, mono$(C_1-C_4)$alkylamino, di$(C_1-C_4)$alkylamino, phenyl and $(C_3-C_6)$cycloalkyl, where each of the 2 last-mentioned radicals is unsubstituted or substituted by one or more radicals from the group consisting of halogen, CN, SCN, $NO_2$, $(C_1-C_4)$alkyl, $(C_1-C_4)$haloalkyl, $(C_1-C_4)$alkoxy and $(C_1-C_4)$haloalkoxy, and, in the case of cyclic radicals, also $(C_1-C_4)$alkyl and $(C_1-C_4)$haloalkyl, and B* is a divalent group of the formula —CO—, —CO—O—, —CO—NR'—, —S(O)$_p$— or —S(O)$_p$—O—, where p=0, 1 or 2 and R' is hydrogen, alkyl having 1 to 6 carbon atoms, phenyl, benzyl, cycloalkyl having 3 to 6 carbon atoms or alkanoyl having 1 to 4 carbon atoms, where -B*-A* including substituents has 1 to 12 carbon atoms, $R^4$ is a radical of the formula -$Z^1$-$R^6$, where $Z^1$ and $R^6$ are as defined below, $R^5$ are each independently of one another halogen, CN, SCN, $NO_2$, a radical of the formula -$Z^2$-$R^7$, where $Z^2$ and $R^7$ are as defined below, or two adjacent radicals $R^5$ together are a fused-on cycle having 4 to 6 ring atoms which is carbocyclic or contains 1 to 3 hetero ring atoms from the group consisting of O, S and N and which is unsubstituted or substituted by one or more radicals from the group consisting of halogen, $(C_1-C_4)$alkyl and oxo, and $R^6$ and $R^7$, $R^8$, $R^9$ are each independently of one another hydrogen, except that $R^7$ is not hydrogen if $Z^2$ is a direct bond, or an acyclic hydrocarbon radical having 1 to 10 carbon atoms or a cyclic hydrocarbon radical having 3 to 6 carbon atoms or a heterocyclic radical, where each of the 3 last-mentioned carbon-containing radicals is unsubstituted or substituted by one or more radicals from the group consisting of halogen, hydroxyl, amino, nitro, formyl, aminocarbonyl, carboxyl, sulfonyl, cyano, thiocyanato, $(C_1-C_6)$alkoxy, $(C_2-C_6)$alkenyloxy, $(C_2-C_6)$alkynyloxy, $(C_1-C_6)$alkoxy-poly(alkyleneoxy), hydroxy-poly(alkyleneoxy), $(C_1-C_6)$alkylthio, mono- and di[$(C_1-C_6)$alkyl]amino, [$(C_1-C_6)$alkyl]carbonyl, [$(C_2-C_6)$alkenyl]carbonyl, [$(C_2-C_6)$alkynyl]carbonyl, [$(C_1-C_6)$alkoxy]carbonyl, [$(C_2-C_6)$alkenyloxy]carbonyl, [$(C_2-C_6)$alkynyloxy]carbonyl, mono- and di[$(C_1-C_6)$alkyl]aminocarbonyl, phenyl, phenoxy, $(C_3-C_6)$cycloalkyl, phenylcarbonyl, phenoxycarbonyl, heterocyclyl, $(C_1-C_4)$alkylsulfonyl and, in the case of cyclic radicals, also $(C_1-C_4)$alkyl, where each of the 24 last-mentioned substituents is unsubstituted or substituted by one or more radicals from the group consisting of halogen, CN, SCN, $NO_2$, $(C_1-C_4)$alkoxy, $(C_1-C_4)$alkylthio, $(C_1-C_4)$haloalkoxy, formyl, $(C_1-C_4)$alkylcarbonyl, [$(C_1-C_4)$haloalkyl]carbonyl, [$(C_1-C_4)$alkoxy]carbonyl, [$(C_1-C_4)$haloalkoxy]carbonyl and, in the case of cyclic radicals, also $(C_1-C_4)$alkyl and $(C_1-C_4)$haloalkyl, $X^1$, $X^2$, $X^3$, $X^4$ are each independently of one another a carbon atom which is substituted by a hydrogen atom or one of the substituents $R^5$ defined above, or a nitrogen atom, or two adjacent symbols $X^1$, $X^2$, $X^3$ and $X^4$ are in each case together a divalent group of the formula —O—, —S—, —NH— or —NR—, where R is as defined for $R^3$, provided the groups $X^1$, $X^2$, $X^3$, $X^4$ together with the attached $C_2$ unit of the fused-on ring form a carbocyclic or heterocyclic aromatic five- or six-membered ring, $(Y^1)_m$ are m divalent groups $Y^1$, where each group $Y^1$ independently of the other radicals $Y^1$ is a group of the formula —O—, —CO—, —C(=NR*)—, —S(O)$_q$—, —NR*— or —N(O)—, where q=0, 1 or 2 and R* is as defined for $R^3$, or a group of the formula $CR^8R^9$, $Y^2$ is a group as defined for $Y^1$ or a direct bond, where two adjacent groups of the symbol pairs $Y^1$ and $Y^1$ or of the symbol pairs $Y^1$ and $Y^2$ are groups with no heteroatoms having the same meaning, and where the groups $(Y^1)_m$ and $Y^2$ together with the attached $C_2$ unit of the aromatic ring and the carbon atom attached to $R^4$ form a fused-on carbocyclic or heterocyclic nonaromatic four- to eight-membered ring, and $Z^1$ and the groups $Z^2$ are each independently of one another a direct bond or a divalent group of the formula —O—, —S(O)$_p$—, —S(O)$_p$—O—, —O—S(O)$_p$—, —CO—, —O—CO—, —CO—O—, —NR'—, —O—NR'—, —NR'—O—, —NR'—CO—, —CO—NR'—, where p=0, 1 or 2 and R' is hydrogen, alkyl having 1 to 6 carbon atoms, phenyl, benzyl, cycloalkyl having 3 to 6 carbon atoms or alkanoyl having 1 to 6 carbon atoms, where heterocyclyl, unless defined otherwise, and including in fused radicals, has in each case 3 to 9 ring atoms and 1 to 3 hetero ring atoms from the group consisting of N, O and S.

3. A compound or a salt thereof as claimed in claim 1, wherein $R^1$ and $R^2$ are each independently of one another hydrogen, amino, mono- or di[$(C_1-C_4)$alkyl]amino or $(C_3-C_6)$cycloalkylamino, $(C_5-C_6)$cycloalkenylamino, a hydrocarbon radical or hydrocarbonoxy radical having in each case 1 to 10 carbon atoms or a heterocyclyl radical, heterocyclyloxy radical, heterocyclylthio radical or heterocyclylamino radical having in each case 3 to 9 ring atoms and 1 to 3 hetero ring atoms from the group consisting of N, O and S, where each of the six last-mentioned radicals is unsubstituted or substituted by one or more radicals from the group consisting of halogen, hydroxyl, amino, nitro, formyl, aminocarbonyl, carboxyl, sulfonyl, cyano, thiocyanato, $(C_1-C_4)$alkoxy, $(C_2-C_4)$alkenyloxy, $(C_2-C_4)$alkynyloxy, $(C_1-C_4)$alkoxy-poly(alkyleneoxy), hydroxy-poly(alkyleneoxy), $(C_1-C_4)$alkylthio, mono- and di[$(C_1-C_4)$alkyl]amino, [$(C_1-C_4)$alkyl]carbonyl, [$(C_2-C_4)$alkenyl]carbonyl, [$(C_2-C_4)$alkynyl]carbonyl, [$(C_2-C_4)$alkoxy]carbonyl, [$(C_2-C_4)$alkenyloxy]carbonyl, [$(C_2-C_4)$alkynyloxy]carbonyl, mono- and di[$(C_1-C_4)$alkyl]aminocarbonyl, phenyl, phenoxy, $(C_3-C_6)$cycloalkyl, phenylcarbonyl, phenoxycarbonyl, heterocyclyl, $(C_1-C_4)$alkylsulfonyl and, in the case of cyclic radicals, also $(C_1-C_4)$alkyl, where each of the 24 last-mentioned substituents is unsubstituted or substituted by one or more radicals from the group consisting of halogen, CN, SCN, NO$_2$, $(C_1-C_4)$alkoxy, $(C_1-C_4)$haloalkoxy, formyl, $(C_1-C_4)$alkylcarbonyl, [$(C_1-C_4)$haloalkyl]carbonyl, [$(C_1-C_4)$alkoxy]carbonyl, [$(C_1-C_4)$haloalkoxy]carbonyl and, in the case of cyclic radicals, also $(C_1-C_4)$alkyl and $(C_1-C_4)$haloalkyl, or an acyl radical of an organic acid from the group consisting of formyl, aminocarbonyl, mono-or di[$(C_1-C_4)$alkyl]aminocarbonyl, [$(C_1-C_4)$alkyl]carbonyl, [$(C_2-C_4)$alkenyl]carbonyl, [$(C_2-C_4)$alkynyl]carbonyl, [$(C_1-C_4)$alkoxy]carbonyl, [$(C_2-C_4)$alkenyloxy]carbonyl, phenylcarbonyl, $(C_1-C_4)$alkylsulfonyl, where each of the 9 last-mentioned radicals is unsubstituted in the aliphatic moiety or in the phenyl ring or substituted by one or more radicals from the group consisting of halogen, CN, SCN, NO$_2$, $(C_1-C_4)$alkoxy, $(C_1-C_4)$haloalkoxy, optionally substituted and unsubstituted phenyl and, in the case of cyclic radicals, also $(C_1-C_4)$alkyl and $(C_1-C_4)$haloalkyl, or $R^1$ and $R^2$ together with the nitrogen atom of the group NR$^1$R$^2$ are a saturated or unsaturated, nonaromatic heterocyclic radical having 3 to 6 ring atoms and 1 to 4 hetero ring atoms, where the further hetero ring atoms optionally present in addition to the nitrogen atom are selected from the group consisting of N, O and S and the radical is unsubstituted or substituted by one or more radicals from the group consisting of halogen, CN, $(C_1-C_4)$alkyl, $(C_1-C_4)$haloalkyl, $(C_1-C_4)$alkoxy, $(C_1-C_4)$haloalkoxy, $(C_1-C_4)$alkoxycarbonyl and oxo, $R^3$ is hydrogen, amino, formyl, $(C_1-C_4)$alkyl, cyano-$(C_1-C_4)$alkyl, $(C_1-C_4)$haloalkyl, mono-, di- or polyhydroxy-$(C_1-C_4)$alkyl, hydroxy-poly[$(C_2-C_4)$alkyleneoxy]-$(C_1-C_4)$alkyl, mono-, di- or poly$(C_1-C_4)$alkoxy-$(C_1-C_4)$alkyl, $(C_1-C_4)$alkoxy-poly[$(C_2-C_4)$alkyleneoxy]-$(C_1-C_4)$alkyl, $(C_1-C_4)$haloalkoxy-$(C_1-C_4)$alkyl, $(C_2-C_6)$alkenyl, $(C_2-C_6)$haloalkenyl, $(C_2-C_6)$alkynyl, $(C_2-C_6)$haloalkynyl or aminocarbonyl or $(C_1-C_4)$alkylamino-$(C_1-C_4)$alkyl, di[$(C_1-C_4)$alkyl]amino-$(C_1-C_4)$alkyl, $(C_1-C_4)$alkylaminocarbonyl, di$(C_1-C_4)$alkylaminocarbonyl, $(C_1-C_5)$alkanoyl, [$(C_2-C_4)$alkenyl]carbonyl, [$(C_1-C_4)$alkoxy]carbonyl, $(C_2-C_4)$alkenyloxycarbonyl, aminocarbonyl-$(C_1-C_4)$alkyl, $(C_1-C_4)$alkylaminocarbonyl-$(C_1-C_4)$alkyl, di[$(C_1-C_4)$alkyl]aminocarbonyl-$(C_1-C_4)$alkyl, $(C_1-C_4)$alkoxycarbonyl-$(C_1-C_4)$alkyl, $(C_1-C_5)$alkanoyl-$(C_1-C_4)$alkyl, [$(C_2-C_4)$alkenyl]carbonyl-$(C_1-C_4)$alkyl, [$(C_1-C_4)$alkoxy]carbonyl-$(C_1-C_4)$alkyl or $(C_2-C_4)$alkenyloxycarbonyl-$(C_1-C_4)$alkyl, where each of the 16 last-mentioned radicals is unsubstituted or substituted by one or more radicals from the group consisting of halogen, CN, $(C_1-C_4)$alkoxy and $(C_1-C_4)$haloalkoxy, or $(C_3-C_6)$cycloalkyl, $(C_3-C_6)$cycloalkylamino-$(C_1-C_4)$alkyl, phenyl, phenylcarbonyl, phenoxycarbonyl, phenylcarbonyl-$(C_1-C_4)$alkyl, phenoxy-$(C_1-C_4)$alkyl, phenyl-$(C_1-C_4)$alkyl, heterocyclyl, heterocyclyl-$(C_1-C_4)$alkyl or one of the 10 last-mentioned radicals which is substituted in the acylic moiety or in the cyclic moiety by one or more radicals from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl and $(C_1-C_4)$alkoxy, $R^4$ is hydrogen, formyl, carboxyl, cyano, thiocyanato, aminocarbonyl, $(C_1-C_4)$alkyl, cyano-$(C_1-C_4)$alkyl, $(C_1-C_4)$alkoxy, $(C_1-C_4)$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 6 ring members where the cyclic groups in the 3 last-mentioned radicals are unsubstituted or substituted by one or more radicals from the group consisting of $(C_1-C_4)$alkyl, halogen and cyano, or phenyl, phenoxy, phenylcarbonyl, phenylcarbonyl-$(C_1-C_4)$alkyl, phenoxycarbonyl, $(C_1-C_4)$alkylcarbonyl, $(C_1-C_4)$alkoxycarbonyl, $(C_1-C_4)$alkylaminocarbonyl, $(C_1-C_4)$alkoxycarbonyl-$(C_1-C_4)$alkyl, $(C_1-C_4)$alkylaminocarbonyl-$(C_1-C_4)$alkyl, phenoxy-$(C_1-C_4)$alkyl, phenyl-$(C_1-C_4)$alkyl, heterocyclyl, heterocyclylamino, heterocyclyloxy, heterocyclylthio, $(C_1-C_5)$alkanoylamino, N-[$(C_1-C_5)$alkanoyl]-N-[$(C_1-C_4)$alkyl]amino, [$(C_2-C_4)$alkenyl]carbonylamino, [$(C_2-C_4)$alkynyl]carbonylamino, [$(C_1-C_4)$alkoxy]carbonylamino, [$(C_2-C_4)$alkenyloxy]carbonylamino, [$(C_2-C_4)$alkynyloxy]carbonylamino, phenylcarbonylamino, phenoxycarbonylamino, $(C_1-C_4)$alkylsulfonyl, $(C_2-C_4)$alkenylsulfonyl or one of the 27 last-mentioned radicals which is substituted in the acyclic moiety or in the cyclic moiety by one or more radicals from the group consisting of halogen, nitro, cyano, $(C_1-C_4)$alkoxy, $(C_1-C_4)$alkylthio, $(C_1-C_4)$haloalkoxy, formyl, $(C_1-C_4)$alkylcarbonyl, $(C_1-C_4)$alkoxycarbonyl, $(C_1-C_4)$alkoxy and, in the case of cyclic moieties, also $(C_1-C_4)$alkyl and $(C_1-C_4)$haloalkyl, $R^5$, if n=1, and the radicals $R^5$ in each case independently of one another, if n is greater than 1, is/are halogen, hydroxyl, amino, nitro, formyl, carboxyl, cyano, thiocyanato, aminocarbonyl, $(C_1-C_4)$alkyl, cyano-$(C_1-C_4)$alkyl, $(C_1-C_4)$alkoxy, $(C_1-C_4$alkylamino, di[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo-$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di[$(C_1-C_4)$alkyl]amino-$(C_1-C_4)$alkyl, $(C_3-C_9)$cycloalkylamino-$(C_1-C_4)$alkyl, $(C_3-C_9)$cycloalkyl, heterocyclyl-$(C_1-C_4)$alkyl having 3 to 6 ring members, where the cyclic groups in the 3 last-mentioned radicals are unsubstituted or substituted by one or more radicals from the group consisting of $(C_1-C_4)$alkyl, halogen and cyano, or phenyl, phenoxy, phenylcarbonyl, phenylcarbonyloxy, phenylcarbonyl-$(C_1-C_4)$alkyl, phenoxycarbonyl, $(C_1-C_4)$alkylcarbonyl, $(C_1-C_4)$alkoxycarbonyl, $(C_1-C_4)$alkylaminocarbonyl, $(C_1-C_4)$alkoxycarbonyl-$(C_1-C_4)$alkyl, $(C_1-C_4)$alkylaminocarbonyl-$(C_1-C_4)$alkyl, phenoxy-$(C_1-C_4)$alkyl, phenyl-$(C_1-C_4)$alkyl, heterocyclyl, heterocyclylamino, heterocyclyloxy, heterocyclylthio, $(C_1-C_5)$alkanoylamino, N-[$(C_1-C_5)$alkanoyl]-N- [$(C_1-C_4)$alkyl]amino, [$(C_2-C_4)$alkenyl]carbonylamino, [$(C_2-C_4)$alkynyl]carbonylamino, [$(C_1-C_4)$ alkoxy]carbonylamino, [(C$_2$-C$_4$)alkenyloxy]carbonylamino, [(C$_2$-C$_4$)alkynyloxy]carbonylamino, phenylcarbonylamino, phenoxycarbonylamino, (C$_1$-C$_4$)alkylsulfonyl, (C$_2$-C$_4$)alkenylsulfonyl or one of the 28 last-mentioned radicals which is substituted in the acyclic moiety or in the cyclic moiety by one or more radicals from the group consisting of halogen, nitro, cyano, (C$_1$-C$_4$)alkoxy, (C$_1$-C$_4$)alkylthio, (C$_1$-C$_4$)haloalkoxy, formyl, (C$_1$-C$_4$)alkylcarbonyl, (C$_1$-C$_4$)alkoxycarbonyl, (C$_1$-C$_4$)alkoxy and, in the case of cyclic moieties, also (C$_1$-C$_4$)alkyl and (C$_1$-C$_4$)haloalkyl, where heterocyclyl in the radicals contains in each case 3 to 9 ring atoms and 1 to 3 hetero ring atoms from the group consisting of N, O and S, or two adjacent radicals R$^5$ together are a fused-on cycle having 4 to 6 ring atoms which is carbocyclic or contains hetero ring atoms from the group consisting of O, S and N and which is unsubstituted or substituted by one or more radicals from the group consisting of halogen, (C$_1$-C$_4$)alkyl and oxo, R$^8$ and R$^9$ are each independently of one another hydrogen, formyl, carboxyl, cyano, thiocyanato, aminocarbonyl, (C$_1$-C$_4$)alkyl, cyano-(C$_1$-C$_4$)alkyl, (C$_1$-C$_4$)alkoxy, (C$_1$-C$_4$)alkylamino, di[(C$_1$-C$_4$)alkyl]amino, halo-(C$_1$-C$_4$)alkyl, hydroxy-(C$_1$-C$_4$)alkyl, (C$_1$-C$_4$)alkoxy-(C$_1$-C$_4$)alkyl, halo-(C$_1$-C$_4$)alkoxy-(C$_1$-C$_4$)alkyl, (C$_1$-C$_4$)alkylthio, halo-(C$_1$-C$_4$)alkylthio, (C$_2$-C$_6$)alkenyl, halo-(C$_2$-C$_6$)alkenyl, (C$_2$-C$_6$)alkynyl, halo-(C$_2$-C$_6$)alkynyl, (C$_1$-C$_4$)alkylamino-(C$_1$-C$_4$)alkyl, di[(C$_1$-C$_4$)alkyl]amino-(C$_1$-C$_4$)alkyl, (C$_3$-C$_9$)cycloalkylamino-(C$_1$-C$_4$)alkyl, (C$_3$-C$_9$)cycloalkyl, heterocyclyl-(C$_1$-C$_4$)alkyl having 3 to 6 ring members, where the cyclic groups in the 3 last-mentioned radicals are unsubstituted or substituted by one or more radicals from the group consisting of (C$_1$-C$_4$)alkyl, halogen and cyano, or phenyl, phenoxy, phenylcarbonyl, phenylcarbonyl-(C$_1$-C$_4$)alkyl, phenoxycarbonyl, (C$_1$-C$_4$)alkylcarbonyl, (C$_1$-C$_4$)alkoxycarbonyl, (C$_1$-C$_4$)alkylaminocarbonyl, (C$_1$-C$_4$)alkoxycarbonyl-(C$_1$-C$_4$)alkyl, (C$_1$-C$_4$)alkylaminocarbonyl-(C$_1$-C$_4$)alkyl, phenoxy-(C$_1$-C$_4$)alkyl, phenyl-(C$_1$-C$_4$)alkyl, heterocyclyl, heterocyclylamino, heterocyclyloxy, heterocyclylthio, (C$_1$-C$_5$)alkanoylamino, N-[(C$_1$-C$_5$)alkanoyl]-N-[(C$_1$-C$_4$)alkyl]amino, [(C$_2$-C$_4$)alkenyl]carbonylamino, [(C$_2$-C$_4$)alkynyl]carbonylamino, [(C$_1$-C$_4$)alkoxyl]carbonylamino, [(C$_2$-C$_4$)alkenyloxy]carbonylamino, [(C$_2$-C$_4$)alkynyloxy]carbonylamino, phenylcarbonylamino, phenoxycarbonylamino, (C$_1$-C$_4$)alkylsulfonyl, (C$_2$-C$_4$)alkenylsulfonyl or one of the 27 last-mentioned radicals which is substituted in the acyclic moiety or in the cyclic moiety by one or more radicals from the group consisting of halogen, nitro, cyano, (C$_1$-C$_4$)alkoxy, (C$_1$-C$_4$)alkylthio, (C$_1$-C$_4$)haloalkoxy, formyl, (C$_1$-C$_4$)alkylcarbonyl, (C$_1$-C$_4$)alkoxycarbonyl, (C$_1$-C$_4$)alkoxy and, in the case of cyclic moieties, also (C$_1$-C$_4$)alkyl and (C$_1$-C$_4$)haloalkyl, X$^1$, X$^2$, X$^3$, X$^4$ are each independently of one another a carbon atom which is substituted by a hydrogen atom or one of the substituents R$^5$ defined above, or a nitrogen atom, or two adjacent symbols X$^1$, X$^2$, X$^3$ and X$^4$ are in each case together a divalent group of the formula —O—, —S—, —NH— or —NR—, where R is as defined for R$^3$, with the proviso that the groups X$^1$, X$^2$, X$^3$, X$^4$ together with the attached C$_2$ unit of the fused-on ring form a carbocyclic or heterocyclic aromatic, five- or six-membered ring, (Y$^1$)$_m$ are m divalent groups Y$^1$, where each group Y$^1$ independently of the other radicals Y$^1$ is a group of the formula —O—, —CO—, —C(=NR*)—, —S(O)$_q$—, —NR*— or —N(O)—, where q=0, 1 or 2 and R* is as defined for R$^3$, or a group of the formula CR$^8$R$^9$, Y$^2$ is a group as defined for Y$^1$ or a direct bond, where two adjacent groups of the symbol pairs Y$^1$ and Y$^1$ or of the symbol pairs Y$^1$ and Y$^2$ are groups with no heteroatoms having the same meaning, and where the groups (Y$^1$)$_m$ and Y$^2$ together with the attached C$_2$ unit of the aromatic ring and the carbon atom attached to R$^4$ form a fused-on carbocyclic or heterocyclic nonaromatic four- to eight-membered ring, where heterocyclyl, unless defined otherwise, and including in fused radicals, has in each case 3 to 9 ring atoms and 1 to 3 hetero ring atoms from the group consisting of N, O and S.

4. A compound or a salt thereof as claimed in claim 1, wherein

R$^1$, R$^2$ independently of one another are hydrogen, amino, formyl, (C$_1$-C$_4$alkyl, (C$_1$-C$_4$)alkylamino, di[(C$_1$-C$_4$)alkyl]amino, hydroxy-(C$_1$-C$_4$)alkyl, (C$_1$-C$_4$)alkoxy-(C$_1$-C$_4$)alkyl, halo-(C$_1$-C$_4$)alkoxy-(C$_1$-C$_4$)alkyl, (C$_2$-C$_6$)alkenyl, (C$_2$-C$_6$)alkynyl, halo-(C$_2$-C$_6$)alkynyl, (C$_1$-C$_4$)alkylamino-(C$_1$-C$_4$)alkyl or phenoxy, phenylcarbonyl, phenylcarbonyl-(C$_1$-C$_4$)alkyl, (C$_1$-C$_4$)alkoxycarbonyl-(C$_1$-C$_4$)alkyl, (C$_1$-C$_4$)alkylaminocarbonyl-(C$_1$-C$_4$)alkyl, (C$_1$-C$_4$)alkylcarbonyl, (C$_1$-C$_4$)alkoxycarbonyl, aminocarbonyl, (C$_1$-C$_4$)alkylaminocarbonyl or one of the 9 last-mentioned radicals which is substituted in the acyclic moiety or in the cyclic moiety by one or more radicals from the group consisting of halogen, nitro, cyano, (C$_1$-C$_4$)alkyl, (C$_1$-C$_4$)alkoxy, (C$_1$-C$_4$)alkylthio, (C$_1$-C$_4$)haloalkyl, formyl, (C$_1$-C$_4$)allcylcarbonyl, (C$_1$-C$_4$)alkoxycarbonyl, (C$_1$-C$_4$) alkoxy, R$^3$ is hydrogen, amino, formyl, (C$_1$-C$_4$)alkyl, cyano-(C$_1$-C$_4$)alkyl, (C$_1$-C$_4$)alkoxy-(C$_1$-C$_4$)alkyl, (C$_2$-C$_6$)alkenyl, halo-(C$_2$-C$_6$)alkenyl, (C$_2$-C$_6$)alkynyl or phenyl, (C$_1$-C$_4$)alkylcarbonyl, (C$_1$-C$_4$)alkoxycarbonyl, aminocarbonyl, phenoxy-(C$_1$-C$_4$)alkyl, phenyl-(C$_1$-C$_4$)alkyl or one of the 6 last-mentioned radicals which is substituted in the acyclic moiety or in the cyclic moiety by one or more radicals from the group consisting of halogen, (C$_1$-C$_4$)alkyl and (C$_1$-C$_4$)alkoxy, R$^4$ is hydrogen, (C$_1$-C$_4$)alkyl, cyano-(C$_1$-C$_4$)alkyl, halo-(C$_1$-C$_4$)alkyl, hydroxy-(C$_1$-C$_4$)alkyl, (C$_1$-C$_4$)alkoxy-(C$_1$-C$_4$)alkyl, halo-(C$_1$-C$_4$)alkoxy-(C$_1$-C$_4$)alkyl, (C$_2$-C$_6$)alkenyl, halo-(C$_2$-C$_6$)alkenyl, (C$_2$-C$_6$)alkynyl, (C$_1$-C$_4$)alkylamino-(C$_1$-C$_4$)alkyl, (C$_3$-C$_9$)cycloalkylamino-(C$_1$-C$_4$)alkyl, (C$_3$-C$_9$)cycloalkyl, heterocyclyl-(C$_1$-C$_4$)alkyl having 3 to 9 ring members, where the cyclic groups in the 3 last-mentioned radicals are unsubstituted or substituted by one or more radicals from the group consisting of (C$_1$-C$_4$)alkyl, halogen and cyano, or phenyl, phenoxy-(C$_1$-C$_4$)alkyl, phenyl-(C$_1$-C$_4$)alkyl, heterocyclyl, or one of the 4 last-mentioned radicals which is substituted in the acyclic moiety or in the cyclic moiety by one or more radicals from the group consisting of halogen, nitro, cyano, (C$_1$-C$_4$)alkoxy, (C$_1$-C$_4$)alkylthio, (C$_1$-C$_4$)haloalkoxy, (C$_1$-C$_4$)alkylcarbonyl, (C$_1$-C$_4$)alkoxycarbonyl, (C$_1$-C$_4$)alkoxy and, in the case of cyclic moieties, also (C$_1$-C$_4$)alkyl and (C$_1$-C$_4$)haloalkyl, R$^5$, if n=1, and the radicals R$^5$ in each case independently of one another, if n is greater than 1, is/are halogen, hydroxyl, amino, nitro, formyl, cyano, aminocarbonyl, (C$_1$-C$_4$)monoalkylaminocarbonyl, (C$_1$-C$_4$)dialkylaminocarbonyl, (C$_1$-C$_4$)alkyl, cyano-(C$_1$-C$_4$)alkyl, (C$_1$-C$_4$) alkoxy, (C$_1$-C$_4$)alkylamino, halo-(C$_1$-C$_4$)alkyl, hydroxy-($C_1$-$C_4$)alkyl, ($C_1$-$C_4$)alkoxy-($C_1$-$C_4$)alkyl, ($C_2$-$C_4$)alkenyl, ($C_2$-$C_4$)alkynyl, ($C_1$-$C_4$)alkylamino-($C_1$-$C_4$)atkyl, di[($C_1$-$C_4$)alkyl]amino-($C_1$-$C_4$)alkyl, or [($C_1$-$C_4$)alkyl]carbonyl, [($C_1$-$C_4$)haloalkyl]carbonyl, [($C_1$-$C_4$)alkoxy-($C_1$-$C_4$)alkyl]carbonyl, formylamino, [($C_1$-$C_4$)alkyl]carbonylamino, [($C_1$-$C_4$)haloalkyl]carbonylamino, phenyl, phenoxy, phenylcarbonyl, phenylcarbonylamino, heterocyclyl or one of the 5 last-mentioned radicals which is substituted by one or more radicals from the group consisting of halogen, ($C_1$-$C_4$)alkyl, ($C_1$-$C_4$)haloalkyl, ($C_1$-$C_4$)alkoxy, ($C_1$-$C_4$)haloalkoxy and ($C_1$-$C_4$)alkylthio, $R^8$ and $R^9$ are each independently of one another hydrogen, ($C_1$-$C_4$)alkyl, cyano-($C_1$-$C_4$)alkyl, halo-($C_1$-$C_4$)alkyl, hydroxy-($C_1$-$C_4$)alkyl, ($C_1$-$C_4$)alkoxy-($C_1$-$C_4$)alkyl, halo-($C_1$-$C_4$)alkoxy-($C_1$-$C_4$)alkyl, ($C_2$-$C_6$)alkenyl, halo-($C_2$-$C_6$)alkenyl, ($C_2$-$C_6$)alkynyl, ($C_1$-$C_4$)alkylamino-($C_1$-$C_4$)alkyl, ($C_3$-$C_9$)cycloalkylamino-($C_1$-$C_4$)alkyl, ($C_3$-$C_9$)cycloalkyl, heterocyclyl-($C_1$-$C_4$)alkyl having 3 to 9 ring members, where the cyclic groups in the 3 last-mentioned radicals are unsubstituted or substituted by one or more radicals from the group consisting of ($C_1$-$C_4$)alkyl, halogen and cyano, or phenyl, phenoxy-($C_1$-$C_4$)alkyl, phenyl-($C_1$-$C_4$)alkyl, heterocyclyl, or one of the 4 last-mentioned radicals which is substituted in the acyclic moiety or in the cyclic moiety by one or more radicals from the group consisting of halogen, nitro, cyano, ($C_1$-$C_4$)alkoxy, ($C_1$-$C_4$)alkylthio, ($C_1$-$C_4$)haloalkoxy, ($C_1$-$C_4$)alkylcarbonyl, ($C_1$-$C_4$)alkoxycarbonyl, ($C_1$-$C_4$)alkoxy and, in the case of cyclic moieties, also ($C_1$-$C_4$)alkyl and ($C_1$-$C_4$)haloalkyl.

5. A compound or a salt thereof as claimed in claim 1, wherein $X^1$, $X^2$, $X^3$, $X^4$ are each independently of one another a carbon atom which is substituted by a hydrogen atom or one of the substituents $R^5$ defined above, or a nitrogen atom or two adjacent symbols $X^1$, $X^2$, $X^3$ and $X^4$ are in each case together a divalent group of the formula —O—, —S—, —NH— or —NR—, where R is hydrogen or ($C_1$-$C_4$)alkyl, with the proviso that the groups $X^1$, $X^2$, $X^3$, $X^4$ together with the attached $C_2$ unit of the fused-on ring form a carbocyclic or heterocyclic aromatic, five- or six-membered ring, ($Y^1$)$_m$ are m divalent groups $Y^1$, where each group $Y^1$ independently of the other radicals $Y^1$ is a group of the formula $CH_2$, $CH(CH_3)$, $CH(C_2H_5)$, $CH(CH_3)_2$ or $CH(C_6H_5)$ and m = 0, 1, 2 or 3 and $Y^2$ is a direct bond or a group of the formula —O—, —S—, $CH_2$, $CH(CH_3)$ or ($C_1$-$C_4$)alkylamino, where two adjacent groups of the symbol pairs $Y^1$ and $Y^1$ or of the symbol pairs $Y^1$ and $Y^2$ are groups without heteroatoms and the same meaning, and where the groups ($Y^1$)$_m$ and $Y^2$ together with the attached $C_2$ unit of the aromatic ring and with the carbon atom attached to $R^4$ form a fused-on carbocyclic or heterocyclic nonaromatic, four- to eight-membered ring.

6. A process for preparing the compound of the formula (I) or salt thereof as defined in claim 1, which comprises a) reacting a compound of the formula (II),

H—$R^{13}$ (II)

in which $R^{13}$ is a functional group of a compound selected from the group consisting of carboxylic esters, carboxylic orthoesters, carbonyl chlorides, carboxamides and carboxylic anhydrides with a biguanide of the formula (III) or an acid addition salt thereof

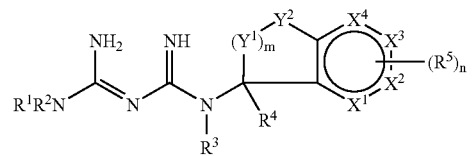

b) reacting a compound of the formula (IV),

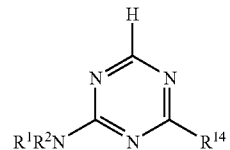

where $R^{14}$ is an exchangeable radical or a leaving group with an amine of the formula (V) or an acid addition salt thereof

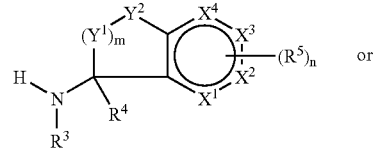

c) reacting a diamino-1,3,5-triazine of the formula (VI) with an isocyanate of the formula (VII)

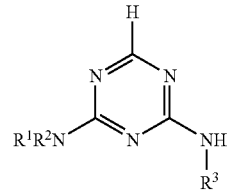

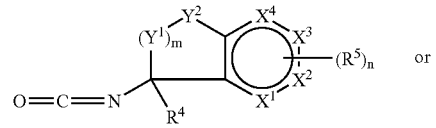

d) removing, in a triazine of the structure (VIII), the radical $R^{15}$ which is a leaving group or a radical that can be removed

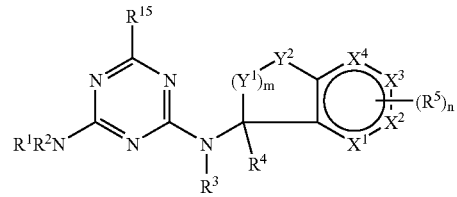

where in the formulae (II), (III), (IV), (V), (VI), (VII) and (VIII) the radicals $R^1$, $R^2$, $R^3$, $R^4$, $R^5$, $X^1$, $X^2$, $X^3$, $X^4$, $Y^1$ and $Y^2$ and the symbols m and n are as defined in formula (I).

7. A herbicidal or plant-growth-regulating composition, which comprises one or more compounds of the formula (I) or salts thereof as claimed in claim 1 and formulation auxiliaries used in crop protection.

8. A method for controlling harmful plants or for regulating the growth of plants, which comprises applying an effective amount of one or more compounds of the formula (I) or salts thereof as claimed in claim 1 onto the plants, plant seeds or the area under cultivation.

9. A method as claimed in claim 8, wherein the compound of the formula (I) or salt thereof are used for controlling harmful plants or for regulating growth in crops of useful or ornamental plants.

10. The compound of claim 1, wherein:
$R^1$ and $R^2$ are independently selected from the group consisting of hydrogen, $(C_1-C_4)$alkyl, $(C_1-C_4)$alkyl]carbonyl and a halogen substituted $(C_1-C_4)$alkyl]carbonyl;
$R^3$ is hydrogen, amino, formyl, $(C_1-C_4)$alkyl, $(C_1-C_4)$alkyl substituted with $(C_1-C_4)$ alkoxy, phenyl, phenyl substituted with halogen, $(C_1-C_4)$alkylcarbonyl, $(C_1-C_4)$alkylcarbonyl substituted with $(C_1-C_4)$ alkoxy,
$R^4$ is hydrogen, $(C_1-C_4)$alkyl, $(C_1-C_4)$alkyl substituted with $(C_1-C_4)$ alkoxy, cyano, $(C_1-C_4)$aikylcarbonyl; $(C_1-C_4)$carbonyl substituted with $(C_1-C_4)$ alkoxy
$X^1$, $X^2$, $X^3$, $X^4$ are each independently of one another a carbon atom which is substituted by a hydrogen atom or one of the substituents $R^5$, wherein
  $R^5$ is halogen, or $-Z^2-R^7$, wherein
    $Z^2$ is a direct bond; and
    $R^7$ is an acyclic hydrocarbon radical having 1 to 20 carbon atoms or an acyclic hydrocarbon radical having 1 to 20 carbon atoms substituted with halogen;
n is 0, 1,2 or 3;
$(Y^1)_m$ are m divalent groups $Y^1$, where each group $Y^1$ independently of the other radicals $Y^1$ is a group of the formula $CR^8R^9$, wherein,
  $R^8$ and $R^9$ are independently of one another hydrogen or an acyclic hydrocarbon radical having 1 to 20 carbon atoms;
m is 1 or 2; and
$Y^2$ is a direct bond, $-N(C_1-C_4$ alkyl$)-$, $-N(Ph)-$, $-N(C_1-C_4$ alkylcarbonyl$)$, $-C(=O)-$, $-CH(OH)-$, $-CH(CH_3)-$, $-O-$, $-S-$, $-SO_2-$, or $-CH_2-$.

11. The compound of claim 10, wherein:
$R^1$ and $R^2$ are independently selected from the group consisting of hydrogen, unsubstituted $(C_1-C_6)$alkyl]carbonyl and a halogen substituted $(C_1-C_6)$alkyl]carbonyl; $R^3$ $R^4$ are hydrogen;
$X^1$, $X^2$, $X^3$, $X^4$ are each independently of one another a carbon atom which is substituted by a hydrogen atom or one of the substituents $R^5$, wherein
  $R^5$ is halogen, or $-Z^2-R^7$, wherein
    $Z^2$ is a direct bond; and
    $R^7$ is an acyclic hydrocarbon radical having 1 to 20 carbon atoms;

n is 0, 1 or 2;
$(Y^1)_m$ are m divalent groups $Y^1$, where each group $Y^1$ independently of the other radicals $Y^1$ is a group of the formula $CR^8R^9$, wherein,
  $R^8$ and $R^9$ are independently of one another hydrogen or an acyclic hydrocarbon radical having 1 to 20 carbon atoms;
m is 1 or 2; and
$Y^2$ is a direct bond, $-O-$, $-S-$ or $-CH_2-$.

12. The compound of claim 11, wherein:
$R^5$ is fluoro, chloro or $-Z^2-R^7$, wherein
  $Z^2$ is a direct bond; and
  $R^7$ is methyl;
$R^8$ and $R^9$ are independently of one another hydrogen, methyl or ethyl; and
m is 1 or 2.

13. The compound of claim 12, wherein:
n is 1 or 2.

14. The compound of claim 13, wherein:
$Y^2$ is a direct bond or $-CH_2-$.

15. A herbicidal or plant-growth-regulating composition, which comprises one or more compounds of the formula (I) or salts thereof as claimed in claim 11 and formulation auxiliaries used in crop protection.

16. A method for controlling harmful plants or for regulating the growth of plants, which comprises applying an effective amount of one or more compounds of the formula (I) or salts thereof as claimed in claim 11 onto the plants, plant seeds or the area under cultivation.

17. A herbicidal or plant-growth-regulating composition, which comprises one or more compounds of the formula (I) or salts thereof as claimed in claim 12 and formulation auxiliaries used in crop protection.

18. A method for controlling harmful plants or for regulating the growth of plants, which comprises applying an effective amount of one or more compounds of the formula (I) or salts thereof as claimed in claim 12 onto the plants, plant seeds or the area under cultivation.

19. A method for controlling harmful plants or for regulating the growth of plants, which comprises applying an effective amount of one or more compounds of the formula (I) or salts thereof:

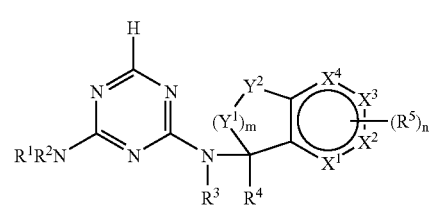

wherein
$R^1$ is an unsubstituted phenyl and $R^2$, $R^3$, $R^4$, $R^5$, $X^1$, $X^2$, $X^3$, $X^4$, $Y^1$, $Y^2$, m, and n are defined as in claim 1; or
$R^1$ and $R^2$ is an unsubstituted phenyl and $R^3$, $R^4$, $R^5$, $X^1$, $X^2$, $X^3$, $X^4$, $Y^1$, $Y^2$, m, and n are defined as in claim 1;
onto the plants, plant seeds or the area under cultivation.

* * * * *